United States Patent
Lerner et al.

(10) Patent No.: US 10,745,456 B2
(45) Date of Patent: Aug. 18, 2020

(54) METHODS AND COMPOSITIONS RELATED TO GPCR AGONIST POLYPEPTIDES

(71) Applicant: THE SCRIPPS RESEARCH INSTITUTE, La Jolla, CA (US)

(72) Inventors: Richard A. Lerner, La Jolla, CA (US); Hongkai Zhang, San Diego, CA (US); Patricia McDonald, Jupiter, FL (US); Jia Xie, San Diego, CA (US); Emmanuel Sturchler, Jupiter, FL (US); Philip Dawson, San Diego, CA (US)

(73) Assignee: The Scripps Research Institute, La Jolla, CA (US)

(*) Notice: Subject to any disclaimer, the term of this patent is extended or adjusted under 35 U.S.C. 154(b) by 0 days.

(21) Appl. No.: 15/563,399

(22) PCT Filed: Apr. 1, 2016

(86) PCT No.: PCT/US2016/025490
§ 371 (c)(1),
(2) Date: Sep. 29, 2017

(87) PCT Pub. No.: WO2016/161244
PCT Pub. Date: Oct. 6, 2016

(65) Prior Publication Data

US 2019/0016774 A1    Jan. 17, 2019

Related U.S. Application Data

(60) Provisional application No. 62/141,598, filed on Apr. 1, 2015.

(51) Int. Cl.
| | |
|---|---|
| *A61K 38/00* | (2006.01) |
| *A61P 3/04* | (2006.01) |
| *A61P 3/10* | (2006.01) |
| *C07K 14/605* | (2006.01) |
| *C12N 15/85* | (2006.01) |
| *A61K 38/17* | (2006.01) |
| *A61K 38/26* | (2006.01) |

(52) U.S. Cl.
CPC .......... *C07K 14/605* (2013.01); *A61P 3/10* (2018.01); *C12N 15/85* (2013.01); *A61K 38/00* (2013.01); *A61K 38/177* (2013.01); *A61K 38/26* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | | | |
|---|---|---|---|---|
| 2004/0053370 A1* | 3/2004 | Glaesner | ............... | C07H 21/04 435/69.7 |
| 2012/0015876 A1* | 1/2012 | Castaigne | ........ | C07K 14/57563 514/4.9 |

OTHER PUBLICATIONS

Patterson et al., "A hydrophobic site on the GLP-1 receptor extracellular domain orients the peptide ligand for signal transduction," Mol. Metab. 2:86-91 (2013) (Year: 2013).*

* cited by examiner

*Primary Examiner* — Julie Ha
*Assistant Examiner* — Kristina M Hellman
(74) *Attorney, Agent, or Firm* — Hugh Wang; Thomas Fitting

(57) ABSTRACT

The invention provides combinatorial peptide or polypeptide libraries that can become membrane tethered once expressed in cells. The invention additionally provides methods for selecting peptide modulators (e.g., agonists) of GPCRs from the combinatorial libraries of the invention. The invention also provides novel GPCR polypeptide modulators, e.g., biased polypeptide agonists of the glucagon-like peptide 1 receptor (GLP-1R). The invention further provides methods of promoting insulin sensitivity, lowering blood glucose, and reducing body weight as well as methods for treating various diseases such as diabetes and obesity.

6 Claims, 21 Drawing Sheets
Specification includes a Sequence Listing.

a b c

METHODS AND COMPOSITIONS RELATED TO GPCR AGONIST POLYPEPTIDES

CROSS-REFERENCE TO RELATED APPLICATIONS

The subject patent application claims the benefit of priority to U.S. Provisional Patent Application No. 62/141,598 (filed Apr. 1, 2015). The full disclosure of the priority application is incorporated herein by reference in its entirety and for all purposes.

BACKGROUND OF THE INVENTION

G-protein-coupled receptors constitute the largest family of cell surface receptor proteins. Upon activation, GPCRs couple to GTP-binding proteins that can be divided into four subclasses, G$\alpha$s-, G$\alpha$i/o-, G$\alpha$q and G$\alpha_{12/13}$. Gs and Gi/o regulate adenylate cyclases leading to an increase (G$\alpha$s) or a decrease (G$\alpha$i/o) in cAMP production, or to an increase in intracellular calcium concentration (G$\alpha$q). G$\alpha$(12/13) activates Rho GEFs, which in turn activate Rho. GPCRs can also engage β-arrestins. Historically, β-arrestin-1 and β-arrestin-2 were believed to serve an exclusive role in GPCR desensitization. However, it has been shown that β-arrestins can also function to activate signaling cascades. Many human diseases are associated with the dysfunction of GPCRs. Thus, GPCRs represent some of the most attractive therapeutic or molecular targets in the pharmaceutical industry.

Insulin regulates the concentration of blood sugar and blood lipid levels through the promotion of glucose and lipid uptake into cells. Type 2 Diabetes Mellitus (T2DM or T2D) is a complex metabolic disorder characterized by hyperglycemia arising from a combination of insufficient insulin secretion together with the development of insulin resistance. T2D and obesity are closely linked, with obesity accounting for 80-85% of the risk of developing T2D. Incretin-based therapies represent a promising class of agents for the treatment of T2D. Incretins including the glucagon-like peptide-1 (GLP-1) and the glucose-dependent insulinotropic polypeptide (GIP) are endogenous peptide hormones secreted from the intestine in response to food intake. GLP-1 and GIP exert their action through G-protein coupled receptor, the GLP-1 and the GIP receptors, respectively. GLP-1R is expressed in pancreatic β-cells as well as various tissues including liver, smooth muscle, heart, kidney, gastrointestinal tract, lungs, pituitary, white adipose tissues, and the central nervous system. GLP-1 lowers postprandial glucose excursion by potentiating glucose-stimulated insulin secretion from pancreatic β-cells and has recently been shown to promote β-cell survival in rodents. In addition, GLP-1 exerts extrapancreatic actions such as promoting gastric emptying, weight loss, intestinal growth and increasing insulin sensitivity in peripheral tissues.

A need exists in the art for better and more robust means for identifying agonists or activators displaying novel pharmacology of various GPCRs. There is also need in the art for new compounds and methods for treating diseases associated with insulin deficiency and high blood glucose. The instant invention addresses these and other currently unmet needs in the art.

SUMMARY OF THE INVENTION

In one aspect, the invention provides isolated or recombinant polypeptides that contain a first randomized peptide fused at its C-terminus to a second peptide capable of binding to the extracellular domain of glucagon-like peptide 1 receptor (GLP-1R). In these polypeptides, the randomized peptide typically has an amino acid sequence of XXXXXXX (SEQ ID NO: 1), CXXXXXCXX (SEQ ID NO:2) or CXXXXCXXX (SEQ ID NO:3), wherein X is any amino acid residue. In various embodiments, these polypeptides can activate glucagon-like peptide 1 receptor (GLP-1R). In some embodiments, the randomized peptide contains an amino acid sequence that is substantially identical to a sequence selected from SEQ ID NOs:4-16 and 22-31, or an active variant or fragment thereof. In some embodiments, the randomized peptide contains an amino acid sequence that is identical to a sequence selected from SEQ ID NOs: 4-16 and 22-31, except for conservative substitution at one or more residues. In some embodiments, the randomized peptide contains an amino acid sequence shown in SEQ ID NO:4 (ACCIDSVCVI), SEQ ID NO:5 (VCPDCQV), SEQ ID NO:6 (ACSYMIDCVL), SEQ ID NO:8 (ELVDNAV), SEQ ID NO:22 (CCIDSVCVI), or SEQ ID NO:23 (CSYMIDCVL).

In some polypeptides of the invention, the second peptide capable of binding to glucagon-like peptide 1 receptor contains an amino acid sequence that is substantially identical to at least 8 contiguous amino acid residues of Ex4 (9-39) (SEQ ID NO: 17), Ex4 (9-30) (SEQ ID NO:38), or human GLP-1 (7-37) peptide (SEQ ID NO:18). In some embodiments, the second peptide capable of binding to GLP-1R contains a sequence that is substantially identical to SEQ ID NO: 17 or SEQ ID NO: 18. In some embodiments, the second peptide capable of binding to GLP-1R contains a sequence shown in SEQ ID NO: 17 or SEQ ID NO: 18, except for conservative substitution at one or more residues. In some embodiments, the second peptide capable of binding to glucagon-like peptide 1 receptor contains a sequence shown in GGDLS KQMEE EAVRL FIEWL KNGGP SSGAP PPS (SEQ ID NO:21). Some of the polypeptides of the invention are G protein biased. Some polypeptides of the invention contain a sequence that is substantially identical to a sequence selected from the group consisting of SEQ ID NOs:32-37. In some of these embodiments, the polypeptide has an amino acid sequence selected from the group consisting of SEQ ID NOs:32-37. In some embodiments, the GLP-1R agonist polypeptides of the invention further contain an Fc-domain fused at its N-terminus or C-terminus. Some of these polypeptides contain an Fc-domain that is fused at the C-terminus of SEQ ID NO:36, e.g., the polypeptide shown in SEQ ID NO:45. Some of these polypeptides can additionally include a signal peptide at the N-terminus.

In another aspect, the invention provides methods for identifying an agonist of a G protein-coupled receptor (GPCR). These methods entail (1) introducing a vector expressing a reporter gene under the control a cAMP response element (cAMP) into a population of host cells expressing the GPCR, (2) expressing in the host cells a combinatorial library of membrane tethered candidate polypeptides to produce a population of host cells co-expressing a candidate polypeptide and the GPCR, (3) identifying a host cell that has increased expression level of the reporter gene relative to a control cell not expressing any candidate polypeptide, and (4) determining the identity of the candidate polypeptide expressed in the identified host cell; thereby identifying an agonist of the G protein-coupled receptor. In some methods, each candidate polypeptide is fused at its C-terminus to a linker and a transmembrane protein domain. In some methods, the employed transmembrane protein domain is the PDGFR transmembrane domain. In some methods, the GPCR is expressed from an expression vector in the host cells. For example, the vector can be a lentiviral vector.

Some of the methods of the invention employ a reporter gene that encodes a GFP protein. In these methods, the reporter gene can be introduced into the host cell via a lentiviral vector. In some embodiments, the employed host cell is the HEK 293T cell. In some embodiments, the employed GPCR is human GLP-1R. In some methods of the invention, each candidate polypeptide contains a first randomized peptide that is fused at its C-terminus to a second peptide capable of binding to the extracellular domain of glucagon-like peptide 1 receptor (GLP-1R), and the randomized peptide contains an amino acid sequence of XXXXXXX (SEQ ID NO:1), CXXXXXCXX (SEQ ID NO:2) or CXXXXCXXX (SEQ ID NO:3), wherein X is any amino acid residue. In some of these methods, the second peptide contains an amino acid sequence that is substantially identical to Ex4 (9-39) (SEQ ID NO:17), Ex4 (9-30) (SEQ ID NO:38), human GLP-1 (7-37) peptide (SEQ ID NO: 18), or an active variant thereof. In some methods, the transmembrane protein domain and the second peptide are connected via a linker peptide. For example, a linker peptide containing two or more tandem repeats of GGGGS (SEQ ID NO:43) can be employed in the methods.

In some methods of the invention, each candidate polypeptide further contains a signal peptide at the N-terminus. For example, the methods can employ a signal peptide containing the IL-2 signal sequence. In some of these methods, the signal peptide can contain an amino acid sequence of MYRMQLLSCIALSLALVTNS (SEQ ID NO:44).

In another aspect, the invention provides methods for activating a signaling pathway mediated by the glucagon-like peptide 1 receptor (GLP-1R) in a cell. These methods involve contacting the cell with an effective amount of a polypeptide containing a first randomized peptide that is fused at its C-terminus to a second peptide capable of binding to the extracellular domain of glucagon-like peptide 1 receptor (GLP-1R). In these methods, the randomized peptide contains an amino acid sequence of XXXXXXX (SEQ ID NO:1), CXXXXXCXX (SEQ ID NO:2) or CXXXXCXXX (SEQ ID NO:3), wherein X is any amino acid residue. In some methods, the second peptide contains a sequence that is substantially identical to Ex4 (9-39) (SEQ ID NO:17), Ex4 (9-30) (SEQ ID NO:38), human GLP-1 (7-37) peptide (SEQ ID NO: 18), or an active variant thereof. In some embodiments, the randomized peptide contains an amino acid sequence as shown in SEQ ID NO:22, SEQ ID NO:5, or SEQ ID NO:8. In some methods, the employed polypeptide contains an amino acid sequence as shown in SEQ ID NO:36, SEQ ID NO:34, or SEQ ID NO:32.

In some methods, the signaling pathway to be activated results in insulin biosynthesis and release. In some embodiments, the activated cell is a pancreatic beta cell. For example, the methods can be directed to activating insulin biosynthesis and release in pancreatic beta cells present in a subject. In some of these embodiments, the subject has or is at risk of developing a metabolic disorder characterized by high blood glucose and low insulin levels, e.g., type 2 diabetes, obesity, non-alcoholic fatty liver disease (NAFLD), non-alcoholic steatohepatitis (NASH) and atherosclerosis.

In still another aspect, the invention provides methods for increasing insulin level, insulin sensitivity, and decreasing blood glucose level, or for treating a disorder characterized by high blood glucose and low insulin levels in a subject. These methods entail administering to the subject an effective amount of a polypeptide containing a first randomized peptide that is fused at its C-terminus to a second peptide capable of binding to the extracellular domain of glucagon-like peptide 1 receptor (GLP-1R). In various embodiments, the randomized peptide in the employed polypeptide contains an amino acid sequence of XXXXXXX (SEQ ID NO: 1), CXXXXXCXX (SEQ ID NO:2) or CXXXXCXXX (SEQ ID NO:3), wherein X is any amino acid residue. In some of these methods, the second peptide contains an amino acid sequence that is substantially identical to Ex4 (9-39) (SEQ ID NO:17), Ex4 (9-30) (SEQ ID NO:38), human GLP-1 (7-37) peptide (SEQ ID NO: 18), or an active variant thereof. In some methods, the randomized peptide contains an amino acid sequence as shown in SEQ ID NO:22, SEQ ID NO:5, or SEQ ID NO:8. In some methods, the employed polypeptide contains an amino acid sequence as shown in SEQ ID NO:36, SEQ ID NO:34, or SEQ ID NO:32. Some of these methods are directed to increasing insulin level and decreasing blood glucose in a subject who has or is at risk of developing diabetes, obesity, non-alcoholic fatty liver disease (NAFLD), non-alcoholic steatohepatitis (NASH), atherosclerosis, Parkinson's disease, Alzheimer's Disease or drug addiction.

The invention also provides the use of a polypeptide containing a first randomized peptide fused at its C-terminus to a second peptide capable of binding to the extracellular domain of glucagon-like peptide 1 receptor (GLP-1R) in the preparation of a pharmaceutical composition for treating diabetes or other disorders characterized by high blood glucose and low insulin levels. The randomized peptide typically contains an amino acid sequence of XXXXXXX (SEQ ID NO:1), CXXXXXCXX (SEQ ID NO:2) or CXXXXCXXX (SEQ ID NO:3), wherein X is any amino acid residue. In some embodiments, the second peptide contains an amino acid sequence that is substantially identical to Ex4 (9-39) (SEQ ID NO:17), Ex4 (9-30) (SEQ ID NO:38), human GLP-1 (7-37) peptide (SEQ ID NO:18), or an active variant thereof. In some embodiments, the randomized peptide contains an amino acid sequence as shown in SEQ ID NO:22, SEQ ID NO:5, or SEQ ID NO:8. In some embodiments, the employed polypeptide contains an amino acid sequence as shown in SEQ ID NO:36, SEQ ID NO:34, or SEQ ID NO:32.

In a related aspect, the invention provides isolated or recombinant polynucleotides that encode a polypeptide containing a randomized peptide fused at its C-terminus to a second peptide capable of binding to the extracellular domain of glucagon-like peptide 1 receptor (GLP-1R). The randomized peptide in the encoded polypeptide typically contains an amino acid sequence of XXXXXXX (SEQ ID NO: 1), CXXXXXCXX (SEQ ID NO:2) or CXXXXCXXX (SEQ ID NO:3), wherein X is any amino acid residue. In some embodiments, the second peptide contains a sequence that is substantially identical to Ex4 (9-39) (SEQ ID NO: 17), Ex4 (9-30) (SEQ ID NO:38), human GLP-1 (7-37) peptide (SEQ ID NO: 18), or an active variant thereof. In some embodiments, the randomized peptide contains an amino acid sequence as shown in SEQ ID NO:22, SEQ ID NO:5, or SEQ ID NO:8. Some polynucleotides of the invention encode a polypeptide containing an amino acid sequence as shown in SEQ ID NO:36, SEQ ID NO:34, or SEQ ID NO:32.

In some embodiments, the polypeptide encoded by the polynucleotide further contains a transmembrane protein domain at the C-terminus of the second peptide. For example, the encoded polypeptide can contain the PDGFR transmembrane domain. In some embodiments, the transmembrane protein and the second peptide in the encoded polypeptide are connected via a linker peptide. For example, a linker peptide containing two or more tandem repeats of GGGGS (SEQ ID NO:43) can be employed. In some embodiments, the encoded polypeptide can further contain a signal peptide at the N-terminus. For example, the IL-2 signal sequence can be used. In some specific embodiments, the employed signal peptide contains a sequence of MYRMQLLSCIALSLALVTNS (SEQ ID NO:44).

In some related aspects, the invention additionally provides fusion polypeptides encoded by the isolated or recombinant polynucleotides, as well as expression vectors harboring the isolated or recombinant polynucleotide of the invention.

A further understanding of the nature and advantages of the present invention may be realized by reference to the remaining portions of the specification and claims.

DETAILED DESCRIPTION OF THE INVENTION

I. Overview

Figure 1:
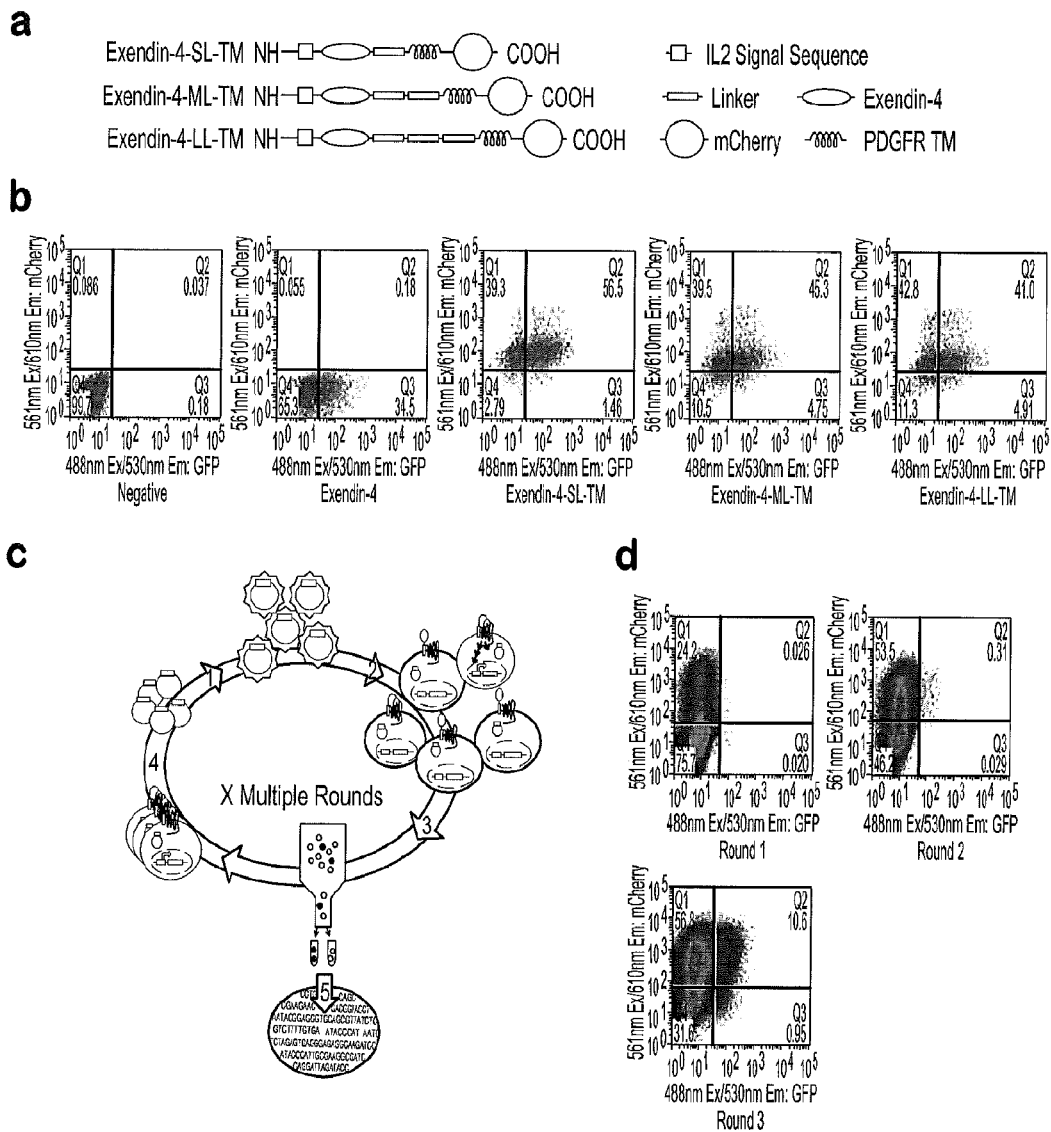
FIG. 1 shows autocrine-based system for selection of agonists from large combinatorial peptide libraries. a, Schematic representation of membrane tethered exendin-4. b, FACS analysis of mCherry and GFP expression 2 of days after transduction of HEK293-GLP-1R-GFP cells with the membrane tethered exendin-4 displaying different linker size. c, Schematic representation of the autocrine based selection of combinatorial peptide library. The lentivirus peptide library is prepared from lentiviral plasmids (step 1). The CRE-responsive GLP-1R reporter cell line is transduced with lentiviral library (step 2). GFP expressing cells are sorted (step 3) and peptide encoding genes are amplified from genomic DNA of sorted cells to make the library for the next selection round(step 4). After iterative rounds of selection, enriched peptide sequences are analyzed by deep sequencing (step 5). d, Enrichment of GFP positive cells during three rounds of FACS selection.

The invention is predicated in part on the development by the present inventors of an autocrine-based system for selection of agonists from large intracellular combinatorial peptide libraries. As detailed herein, this system allows one out of about $10^8$ different peptides and a receptor to be co-localized in the plasma membrane of cells. When the co-localized peptide activates the neighboring receptor a fluorescent signal is generated such that each cell becomes a reporter unto itself. The system was validated by selection of highly potent agonists for the GLP-1 GPCR receptor that activated signaling pathways and induced insulin secretion and lowering of blood glucose in mice. Unlike the balanced agonists, endogenous GLP-1 or the synthetic peptide Exendin4 that activate both Gα-protein and β-arrestin signaling pathways, the selected molecules were biased in that they activated both Gαs and Gαq but not the β-arrestin mediated signal transduction pathways. Such studies open the way to select new agonists for GPCRs and other receptors. Agonists selected by these methods are useful for de-convolution of signal transduction pathways and discovery of new mechanisms of action.

As exemplified herein, the inventors examined the glucagon-like peptide-1 (GLP-1) system. GLP-1 carboxamide is an important incretin hormone that activates the GPCR GLP-1 receptor (GLP-1-R) resulting in a lowering of blood glucose levels in a glucose-dependent manner. When the endogenous GLP-1 binds to the receptor, a complex network of downstream signaling pathways are activated that include, amongst others, G-proteins, β-arrestin and a variety of kinases. Specifically, the inventors constructed combinatorial peptide libraries and expressed them in reporter cells such that each cell expresses the GLP-1R and a different peptide that are co-localized on the plasma membrane. In one library, a sequence of 7 randomized seven amino acids was coupled to the Exentin-4 C-terminus (amino acids 9-39) as an anchor sequence. Exendin-4 from the Gila monster lizard *Heloderma suspectum* was chosen as the anchor sequence so as not to be confused by the agonist activity of the C-terminal GLP-1 domain. When the amino terminus of exendin-4 is truncated by the first eight amino acid residues (Ex9-39), it acts as an antagonist of the GLP-1R. This autocrine selection system is linked to a fluorescent signal such that receptor activation can be monitored and selected in the cell sorter.

Some of the GLP-1R agonists identified by the inventors are G-protein biased (e.g., peptide P5). It is known that GLP-1R coupling to G-protein upon activation can lead to an increase in intracellular 3',5' cyclic AMP (cAMP) and elevation of intracellular $Ca^{2+}$ concentration, which are critical events in promoting glucose-dependent insulin secretion in the pancreatic β-cells. GLP-1R mediated physiological consequences also include engagement of β-arrestins which regulates insulin secretion. Current treatments with GLP-1R agonists have demonstrated anti-diabetic effects, but also shown various adverse side effects and concerns. Optimization of these GLP-1R agonist therapies often focuses on increasing the half-life of GLP-1 and GLP-1 mimetics which signal via both G-protein and β-arrestin coupling.

Figure 2:
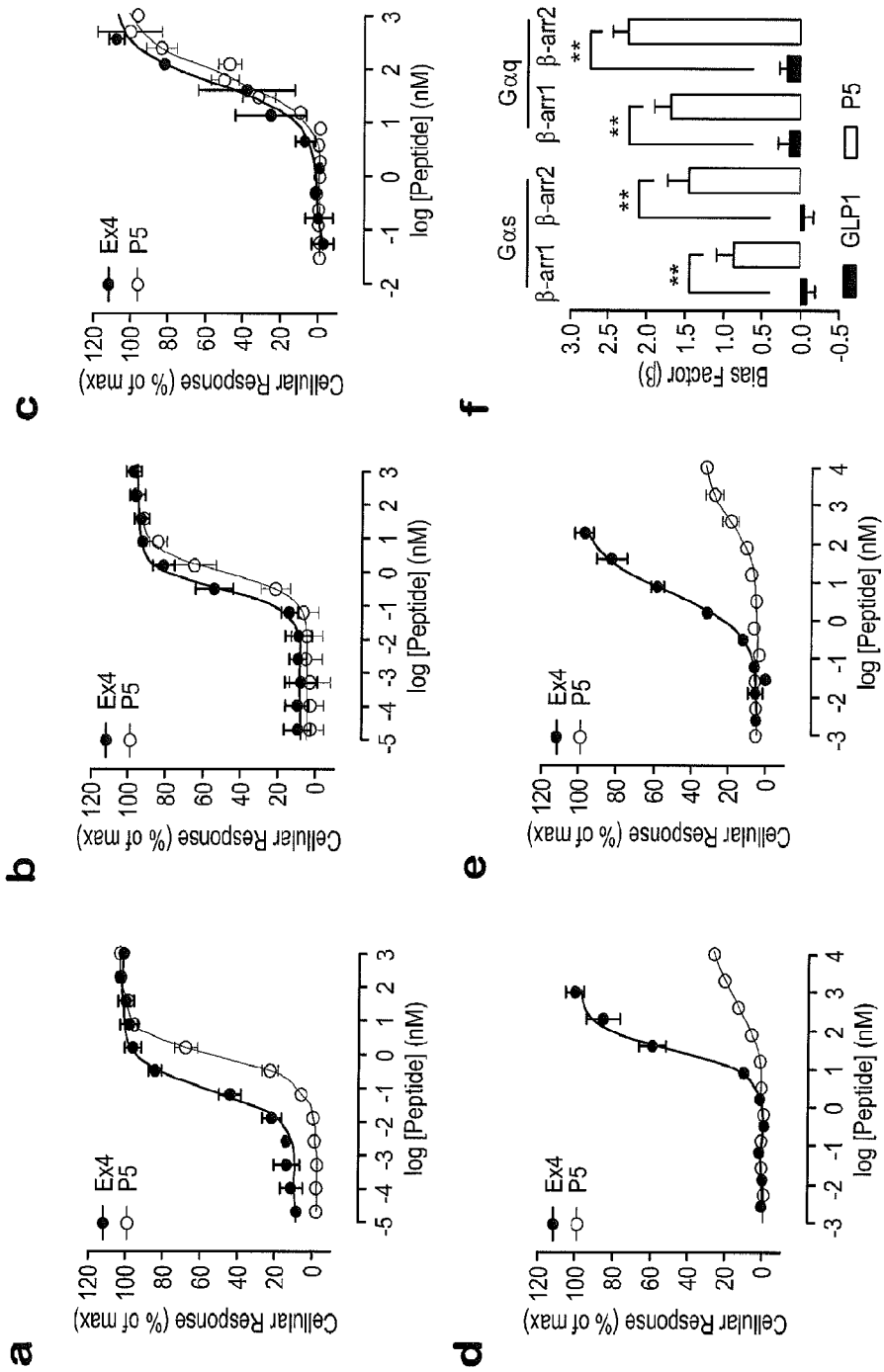
FIG. 2 shows in vitro pharmacological characterization of agonist peptide P5. a-b, Concentration response curves for P5- and Ex4-induced increase in cAMP production in CHO cells expressing the human GLP-1R (a) or in HEK293 expressing the mouse GLP-1R (b). c, Concentration response curves for P5- and Exe4-induced calcium mobilization in CHO cells expressing the human GLP-1R. d-e, Concentration response curves for P5- and Exe4-induced β-arrestin-1 (d) and β-arrestin-2 (e) recruitment in CHO cells expressing the human GLP-1R. f, Biased factors (β) from an equiactive comparison indicate bias for P5. The data are mean±SEM of typical experiment that was performed three times.
Figure 11:
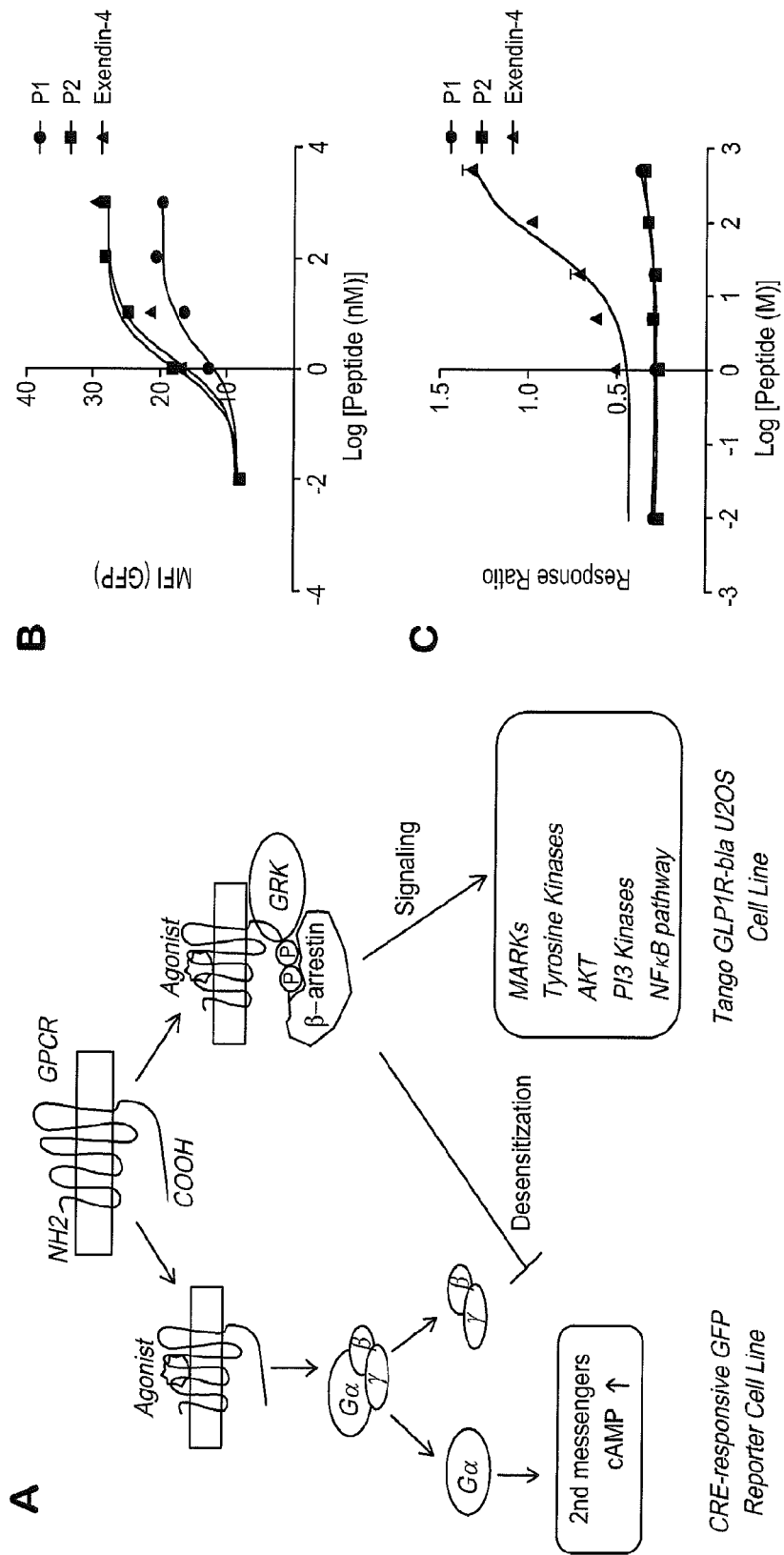
FIG. 11 shows G-protein bias of other agonist peptides in activating GLP-1R signaling. (A) Classical paradigm of signal transduction by GPCR. The agonist binding to the receptor stimulates heterotrimeric G proteins and is rapidly phosphorylated by G protein-coupled receptor kinases (GRKs that recruit β-arrestin to desensitize the receptor; CRE-responsive GLP-1R reporter cell line (B) and Tango GLP-1R-Bla U2OS cell line (C) are used to monitor the cAMP increase and β-arrestin recruitment after GPCR activation.

G-protein bias of some peptides of the invention refers to the ability of the peptides to preferentially signal via G-protein-coupled pathways relative to β-arrestin mediated pathways (as illustrated in FIG. 11a). As exemplified herein (FIG. 2), such a bias can be measured with a bias factor (β), which quantifies the relative engagement of one signaling state over another and is calculated using the equation described herein. With the intracellular combinatorial libraries described herein, the inventors were able to identify biased agonists that selectively activate only some of these pathways. For example, to de-convolute the function of the selected agonists, two reporter systems were constructed to measure either activation of the adenyl cyclase or β-arrestin mediated pathways. It was found that the selected peptide sequences are biased agonists for the GLP-1R receptor that, unlike the natural GLP-1 ligand, activate G-protein signaling but do not signal through β-arrestin (see, e.g., Example 3). Relative to the GLP-1 analogue exendin-4, some of the biased GLP-1R agonists of the invention (e.g., Peptide 5 exemplified herein) demonstrated better or comparable activities in lowering blood glucose. However, these biased peptides (e.g., P5) potentiated the insulin secretory response to a lesser extent than Ex4. For example, in mice fed the high fat diet, the increase in plasma insulin level was significantly lower in response to P5 when compared to the same dose of Ex4. Further, it was found that GLP-1R agonists of the invention (e.g., P5-Fc) could significantly reduce body weight, decrease food intake, and promote intestinal growth in an animal model of obesity (see, e.g., Example 6). Moreover, the G protein biased GLP-1R agonist P5 of the invention was found to be effective in improving hepatic steatosis which underscores many fatty liver diseases such as non-alcoholic steatohepatitis (see, e.g., Example 7). The G-protein biased GLP-1R agonists of the invention offer unappreciated advantages in the context of chronic treatment such as improving glycemic control while preserving pancreatic 1 cell function by minimizing the insulin secretory burden.

A further understanding of the nature and advantages of the present invention may be realized by reference to the remaining portions of the specification and the claims.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press (1st ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons ($3^{rd}$ ed., 2002); *Dictionary of Chemistry*, Hunt (Ed.), Routledge ($1^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology (Oxford Paperback Reference)*, Martin and Hine (Eds.), Oxford University Press ($4^{th}$ ed., 2000). In addition, the following definitions are provided to assist the reader in the practice of the invention.

Unless defined otherwise, all technical and scientific terms used herein have the same meaning as commonly understood by those of ordinary skill in the art to which this invention pertains. The following references provide one of skill with a general definition of many of the terms used in this invention: Oxford Dictionary of Biochemistry and Molecular Biology, Smith et al. (eds.), Oxford University Press (revised ed., 2000); Dictionary of Microbiology and Molecular Biology, Singleton et al. (Eds.), John Wiley & Sons (3PrdP ed., 2002); and A Dictionary of Biology (Oxford Paperback Reference), Martin and Hine (Eds.), Oxford University Press (4PthP ed., 2000). In addition, the following definitions are provided to assist the reader in the practice of the invention.

The singular terms "a," "an," and "the" include plural referents unless the context clearly indicates otherwise. Similarly, the word "or" is intended to include "and" unless the context clearly indicates otherwise.

As used herein, the term "amino acid" of a peptide refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, y-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. The GLP-1R agonist peptides or fusions thereof of the invention encompass derivative or analogs which have been modified with non-naturally coding amino acids.

β-arrestins are well known regulators of GPCR-mediated signaling. Upon GPCR activation, β-arrestins translocate to the cell membrane and bind to the agonist-occupied receptors. This uncouples these receptors from G proteins and promotes their internalization, thus causing desensitization. β-arrestins also play important roles in receptor trafficking and signaling, e.g., serving as scaffolds and adapters in receptor endocytosis and signal transduction, and recruiting endocytic proteins and a variety of signaling molecules to the receptors, thus connecting GPCRs to various pathways, such as MAPK cascades. These latter activities of β-arrestins are referred to as β-arrestin signaling or signaling pathways.

The term "contacting" has its normal meaning and refers to combining two or more agents (e.g., polypeptides or polynucleotides), combining agents and cells, or combining two populations of different cells. Contacting can occur in vitro, e.g., mixing two polypeptides or mixing a population of antibodies with a population of cells in a test tube or growth medium. Contacting can also occur in a cell or in situ, e.g., contacting two polypeptides in a cell by coexpression in the cell of recombinant polynucleotides encoding the two polypeptides, or in a cell lysate.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" refer to a variant which has conservative amino acid substitutions, amino acid residues replaced with other amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As used herein, a "derivative" of a reference molecule (e.g., a GLP-1R agonist peptide disclosed herein) is a molecule that is chemically modified relative to the reference molecule while substantially retaining the biological activity. The modification can be, e.g., oligomerization or polymerization, modifications of amino acid residues or peptide backbone, cross-linking, cyclization, conjugation, fusion to additional heterologous amino acid sequences, or other modifications that substantially alter the stability, solubility, or other properties of the peptide.

The term "engineered cell" or "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

Exendin-4 is a 39 amino acid agonist of the glucagon-like peptide 1 (GLP-1) receptor. Exendin-4 is present in the saliva of the Gila monster, *Heloderma suspectum*. Exendin-4 has a significantly longer half-life than GLP-1.

The term "fragment" refers to any peptide or polypeptide having an amino acid residue sequence shorter than that of a full-length polypeptide whose amino acid residue sequence is described herein. An isolated peptide of exendin-4 is shortened or truncated compared to its parent full-length exendin-4 peptide. Relative to a full length exendin-4 sequence, exendin-4 fragments for fusion with the GLP-1R agonist peptides of the invention typically have the first 4, 5, 6, 7, 8, 9, 10, 12, 15, 20 or more residues at the N-terminus deleted. Other exendin-4 fragments can alternatively or additionally contain C-terminus truncations (e.g., truncations of up to 5, 10, 20 or more C-terminal residues) and/or also internal deletions.

A "fusion" protein or polypeptide refers to a polypeptide comprised of at least two polypeptides and a linking sequence or a linkage to operatively link the two polypeptides into one continuous polypeptide. The two polypeptides linked in a fusion polypeptide are typically derived from two independent sources, and therefore a fusion polypeptide comprises two linked polypeptides not normally found linked in nature.

"Linkage" refers to means of operably or functionally connecting two biomolecules (e.g., polypeptides or polynucleotides encoding two polypeptides), including, without limitation, recombinant fusion, covalent bonding, disulfide bonding, ionic bonding, hydrogen bonding, and electrostatic bonding. "Fused" refers to linkage by covalent bonding. A "linker" or "spacer" refers to a molecule or group of molecules that connects two biomolecules, and serves to place the two molecules in a preferred configuration with minimal steric hindrance.

Glucagon-like peptide-1 (GLP-1) is an incretin derived from the transcription product of the proglucagon gene. The major source of GLP-1 in the body is the intestinal L cell that secretes GLP-1 as a gut hormone. The biologically active forms of GLP-1 are: GLP-1-(7-37) and GLP-1-(7-36)-NH2. Those peptides result from selective cleavage of the proglucagon molecule. GLP-1 is a potent antihyperglycemic hormone enhancing glucose-dependent stimulation of insulin secretion while suppressing glucagon secretion. Such glucose-dependent action is particularly attractive because, when the plasma glucose concentration is within the normal range, GLP-1 no longer stimulates insulin secretion. Therefore, GLP-1R agonists do not cause hypoglycemia. GLP-1 has been shown to inhibit pancreatic β-cell apoptosis and stimulate the proliferation and differentiation of insulin-secreting β-cells. In addition, GLP-1 inhibits gastric emptying and motility. This delays and protracts carbohydrate absorption and contributes to a satiating effect.

GLP-1R is a member of the glucagon receptor family of G protein-coupled receptors. GLP-1R binds specifically the glucagon-like peptide-1 (GLP-1) and has much lower affinity for related peptides such as the gastric inhibitory polypeptide and glucagon. GLP-1R is known to be expressed in pancreatic 1 cells as well as in extrapancreatic tissues including the central nervous system, the peripheral nervous system, adipose tissues, the stomach, the intestine and the heart. Activated GLP-1R stimulates the adenylyl cyclase pathway which results in increased insulin synthesis and release of insulin. Consequently, GLP-1R has been suggested as a potential target for the treatment of diabetes.

The term "isolated" means a molecule is removed from its natural surroundings. However, some of the components found with it may continue to be with an "isolated" protein. Thus, an "isolated polypeptide" is not as it appears in nature but may be substantially less than 100% pure protein.

The terms "identical" or percent "identity," in the context of two or more nucleic acids or polypeptide sequences, refer to two or more sequences or subsequences that are the same.

Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

Methods of alignment of sequences for comparison are well known in the art. Optimal alignment of sequences for comparison can be conducted, e.g., by the local homology algorithm of Smith and Waterman, Adv. Appl. Math. 2:482c, 1970; by the homology alignment algorithm of Needleman and Wunsch, J. Mol. Biol. 48:443, 1970; by the search for similarity method of Pearson and Lipman, Proc. Nat'l. Acad. Sci. USA 85:2444, 1988; by computerized implementations of these algorithms (GAP, BESTFIT, FASTA, and TFASTA in the Wisconsin Genetics Software Package, Genetics Computer Group, Madison, Wis.); or by manual alignment and visual inspection (see, e.g., Brent et al., Current Protocols in Molecular Biology, John Wiley & Sons, Inc. (ringbou ed., 2003)). Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

Nonalcoholic steatohepatitis (NASH) is a common, often "silent" liver disease. It resembles alcoholic liver disease, but occurs in people who drink little or no alcohol. The major feature in NASH is fat in the liver, along with inflammation and damage. Most people with NASH feel well and are not aware that they have a liver problem. Nevertheless, NASH can be severe and can lead to cirrhosis, in which the liver is permanently damaged and scarred and no longer able to work properly.

Non-alcoholic fatty liver disease (NAFLD) is one of the causes of fatty liver, occurring when fat is deposited (steatosis) in the liver due to causes other than excessive alcohol use. Although having fat in the liver is not normal, by itself it probably causes little harm or permanent damage. If fat is suspected based on blood test results or scans of the liver, this problem is called nonalcoholic fatty liver disease (NAFLD). If a liver biopsy is performed in this case, it will show that some people have NASH while others have simple fatty liver. Thus, NASH is also considered an extreme form of NAFLD.

Unless otherwise specified, the terms "polypeptide" and "peptide" are used interchangeably herein to refer to a polymer of amino acid residues. They encompass both short oligopeptides (e.g., peptides with less than about 25 residues) and longer polypeptide molecules (e.g., polymers of more than about 25 or 30 amino acid residues). Typically, the GLP-1R agonist peptides or fusions thereof of the invention can comprise from about 4 amino acid residues to about 350 or more amino acid residues in length. In some embodiments, the peptides or polypeptides comprise from about 6 amino acid residues to about 60 amino acid residues in length. In some other embodiments, the agonists can comprise from about 8 amino acid residues to about 40 amino acid residues in length. The GLP-1R agonist peptides or fusions thereof of the invention include naturally occurring amino acid polymers and non-naturally occurring amino acid polymer, as well as amino acid polymers in which one or more amino acid residue is an artificial chemical mimetic of a corresponding naturally occurring amino acid. Unless otherwise indicated, a particular polypeptide sequence also implicitly encompasses conservatively modified variants thereof.

As used herein, the term "peptide mimetic" or "peptidomimetic" refers to a derivative compound of a reference peptide (e.g., a GLP-1R agonist peptide disclosed herein) that biologically mimics the peptide's functions. Typically, the peptidomimetic derivative of a GLP-1R agonist peptide or fusion thereof has at least 50%, at least 75% or at least 90% of the GLP-1R-activating activities (e.g., lowering blood glucose) of the reference polypeptide.

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

Unless otherwise noted, the term "receptor" broadly refers to a molecule that has an affinity for a given ligand. Receptors may-be naturally-occurring or manmade molecules. Also, they can be employed in their unaltered state or as aggregates with other species. Receptors may be attached, covalently or noncovalently, to a binding member, either directly or via a specific binding substance. A typical example of receptors which can be employed in the practice of the invention is cell surface signaling receptor such as GPCRs. The term "target receptor" refers to a receptor molecule of interest that is to be analyzed or studied with methods of the invention.

The phrase "signal transduction pathway" or "signaling activities" (e.g., the GLP-1R mediated signaling) refers to at least one biochemical reaction, but more commonly a series of biochemical reactions, which result from interaction of a cell with a stimulatory compound or agent. Thus, the interaction of a stimulatory compound (e.g., a GLP-1R agonist polypeptide) with a cell generates a "signal" that is transmitted through the signal transduction pathway, ultimately resulting in a cellular response.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

A cell has been "transformed" by exogenous or heterologous polynucleotide when such polynucleotide has been introduced inside the cell. The transforming DNA may or may not be integrated (covalently linked) into the genome of the cell. In prokaryotes, yeast, and mammalian cells for example, the transforming polynucleotide may be maintained on an episomal element such as a plasmid. With respect to eukaryotic cells, a stably transformed cell is one in which the transforming polynucleotide has become integrated into a chromosome so that it is inherited by daughter cells through chromosome replication. This stability is demonstrated by the ability of the eukaryotic cell to establish cell lines or clones comprised of a population of daughter cells containing the transforming polynucleotide. A "clone" is a population of cells derived from a single cell or common ancestor by mitosis. A "cell line" is a clone of a primary cell that is capable of stable growth in vitro for many generations.

As used herein, the term "treat" or treatment" refers to administration of compounds or agents to prevent or delay the onset of the symptoms, complications, or biochemical indicia of a disease or condition, alleviating the symptoms or arresting or inhibiting further development of the disease or condition, or disorder. Treatment may be prophylactic (to prevent or delay the onset of the condition, or to prevent the manifestation of clinical or subclinical symptoms thereof) or therapeutic suppression or alleviation of symptoms after the manifestation of the condition.

As used herein, the term "variant" refers to a molecule (e.g., a peptide or polypeptide) that contains a sequence that is substantially identical to the sequence of a reference molecule. For example, the reference molecule can be GLP-1R agonist Peptide 5 or 2 disclosed herein or a fusion thereof. The reference molecule can also be a polynucleotide encoding the GLP-1R agonist Peptide 5 or 2 disclosed herein or a fusion thereof. In some embodiments, the variant can share at least 50%, at least 70%, at least 80%, at least 90, at least 95% or more sequence identity with the reference molecule. In some other embodiments, the variant differs from the reference molecule by having one or more conservative amino acid substitutions. In some other embodiments, a variant of a reference molecule (e.g., a GLP-1R agonist peptide or fusion thereof) has altered amino acid sequences (e.g., with one or more conservative amino acid substitutions) but substantially retains the biological activity of the reference molecule (e.g., promoting insulin synthesis and release). Conservative amino acid substitutions are well known to one skilled in the art.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

III. Membrane Tethered Polypeptide Libraries and Selection for Receptor Agonists The invention provides combinatorial libraries of polypeptides or peptides which can become membrane tethered upon being expressed in cells, and methods of using such combinatorial libraries to select agonists of cell surface receptors (e.g., a GPCR such as GLP-1R). The libraries can each contain at least $1 \times 10^4$, $1 \times 10^5$, $1 \times 10^6$, $1 \times 10^7$, $1 \times 10^8$, $1 \times 10^9$, $1 \times 10^{10}$ or more different polypeptide or peptide sequences. Typically, each member of the library contains a specific or randomized peptide which is operably linked to a transmembrane domain. The transmembrane domain, e.g., a PDGFR transmembrane region as exemplified herein, allows the expressed peptides to be tethered to cell membrane. Other than PDGFR, many other transmembrane domains well known in the art can also be employed in the construction of the peptide libraries of the invention. See, e.g., Remm et al., Genome Res. 10: 1679-1689, 2000; and Hubert et al., Cell Adh. Migr. 4: 313-324, 2010. In some embodiments, the peptide or polypeptide sequence is connected with the transmembrane domain via a linker peptide or linker sequence. For example, a linker peptide comprising tandem repeats of GGGGS (SEQ ID NO:43) can be used in constructing the polypeptide libraries of the invention. In various embodiments, the linker can contain 2, 3, 4, 5, 6, 7, 8, 9, 10 or more tandem repeats of the GGGGS (SEQ ID NO:43) sequence.

Members of the combinatorial libraries of the invention can contain at least 4, 5, 6, 8, 10, 15, 20, 25, 30, 40, 50, 75, 100 or more amino acid residues in length. Any polypeptides or peptides can be employed in the construction of the combinatorial polypeptide libraries of the invention. In some embodiments, members of the library are naturally occurring polypeptides or their fragments. These can be obtained from a natural source, e.g., a cell or tissue lysate. Libraries of polypeptide agents can also be prepared, e.g., from a cDNA library commercially available or generated with routine methods. In some embodiments, members of the library are derived from a known sequence, e.g., analogs or variants of a known agonist of a receptor. In some other embodiments, the members of the library are short peptides, e.g., peptides of from about 5 to about 30 amino acids. The peptides can be digests of naturally occurring proteins, random peptides, or "biased" random peptides. In some embodiments, randomized amino acid sequences can be fused to a known anchor sequence, e.g., as exemplified herein for selecting agonists of GLP-1R. In some embodiments, members of the combinatorial libraries of peptides or polypeptides are fully randomized, with no sequence preferences or constants at any position. In some other embodiments, the library can be biased, i.e., some positions within the sequence are either held constant, or are selected from a limited number of possibilities. For example, in some cases, the amino acid residues are randomized within a defined class, for example, of hydrophobic amino acids, hydrophilic residues, satirically biased (either small or large) residues, towards the creation of cysteines, for cross-linking, prolines for SH-3 domains, serines, threonines, tyrosines or histidines for phosphorylation sites, or to purines.

Combinatorial polypeptide or peptide libraries of the invention can be synthesized in a step-by-step fashion. Large combinatorial libraries of compounds can be constructed by the encoded synthetic libraries (ESL) method described in WO 95/12608, WO 93/06121, WO 94/08051, WO 95/35503 and WO 95/30642. Peptide libraries can also be generated by phage display methods (see, e.g., Devlin, WO 91/18980). Nevertheless, as exemplified herein for GLP-1R agonist polypeptides, conventional genetic engineering techniques are typically employed in the present invention for expression of the library of polypeptides. To produce a recombinant polypeptide library of the invention, the polynucleotides encoding the polypeptide are inserted into a suitable expression system. The invention accordingly also provides polynucleotide sequences encoding the members of the combinatorial libraries of peptides or polypeptides described herein. In some embodiments, the polynucleotides comprise a sequence encoding a signal peptide, a candidate polypeptide sequence, a linker peptide, and a transmembrane domain. The candidate polypeptide sequence can be a member of any of the combinatorial peptide or polypeptide libraries described herein. In an exemplified embodiment, the polynucleotide can be placed under the control of an appropriate promoter in an expression vector, e.g., EF1a promoter in a lentiviral vector as exemplified herein. In some embodiments, the polynucleotides encode a signal peptide at the N-terminus. For example, a sequence encoding the IL-2 signal peptide can be used in the polynucleotides and expression vectors of the invention. In some embodiments, the signal peptide comprises a sequence of MYRMQLLSCIALSLALVTNS (SEQ ID NO:44).

Construction of the polynucleotides and expression vectors of the invention can be readily carried out in accordance with routinely practiced methods of molecular biology. Some specific protocols for performing the required steps of the invention are also exemplified herein. Expression of the polypeptides can employ numerous types of appropriate expression vectors are known in the art, including, e.g., vectors containing bacterial, viral, yeast, fungal, insect or mammalian expression systems. As exemplified herein, a preferred expression system for producing the peptide libraries of the invention is lentiviral based. Methods for obtaining and using such expression vectors are well-known. For guidance in this and other molecular biology techniques used for compositions or methods of the invention, see, e.g., Sambrook et al, Molecular Cloning, A Laboratory Manual, current edition, Cold Spring Harbor Laboratory, New York; Miller et al, Genetic Engineering, 8:277-298 (Plenum Press, current edition), Wu et al, Methods in Gene Biotechnology (CRC Press, New York, N.Y., current edition), Recombinant Gene Expression Protocols, in Methods in Molecular Biology, Vol. 62, (Tuan, ed., Humana Press, Totowa, N.J., current edition), and Current Protocols in Molecular Biology, (Ausabel et al, Eds.,) John Wiley & Sons, NY (current edition), and references cited therein.

For selecting GLP-1R agonists, members of the combinatorial library can contain at least 4, 5, 6, 7, 8, 10, 15, 20 or more amino acid residues in length. In some embodiments, the randomized peptides comprise a sequence of XXXXXXX (SEQ ID NO: 1), CXXXXXCXX (SEQ ID NO:2) or CXXXXCXXX (SEQ ID NO:3). To facilitate cleavage of the secretory signal peptide sequence upon expression, the randomized sequences can contain an Ala residue at the N-terminal, e.g., ACXXXXXCXX (SEQ ID NO:41) or ACXXXXCXXX (SEQ ID NO:42). In these sequences, X can be any amino acid residue, e.g., any one of the 20 natural amino acid residues.

The invention provides autocrine-based methods for selection of modulators (e.g., agonists) of cell surface receptors (e.g., GPCRs) from large intracellular combinatorial polypeptide libraries. With the methods, a library of candidate polypeptides or peptides expressed inside a population of host cells or producer cells co-expressing a target receptor. Each different candidate polypeptide from the library and the target receptor are co-localized in the plasma membrane of a population of the host cells. The cells are examined for ability to cause a change in a signaling pathway mediated by the receptor or a specific phenotype of the cells. To facilitate monitoring of receptor activation, the host cells also harbor a detectable reporter molecule (e.g., a reporter gene) which can be detected when the cell surface receptor is activated. When the co-localized polypeptide activates the neighboring receptor, a detectable signal from the reporter molecule (e.g., a fluorescent signal) is generated. Thus, each cell becomes a reporter unto itself.

Typically, the specific phenotype to be altered is an activity, a signaling pathway or cellular process mediated by the co-expressed GPCR in the population of cells. Polypeptides that can cause an alteration in the phenotype of interest are identified as modulators (e.g., agonists) of the GPCR. Depending on the specific target receptor, the phenotype or signaling pathway to be monitored in the methods can be any cellular activity or physiological function mediated by the receptor. However, in some preferred embodiments, the phenotype or signaling pathway to be monitored in the selection methods is response of a reporter molecule (e.g., expression of a reporter gene) introduced into the host cells. For example, for selecting GPCR agonists, the exogenous reporter molecule can be a GFP gene under the control of a transcription regulatory element that is responsive to activation of a GPCR, e.g., the cAMP response element (CRE) or the multiple-response element (MRE). As exemplified herein for selecting GLP-1R agonists, when the receptor on the surface of the host cell is bound by a nearby co-localized agonist polypeptide, the cAMP signaling pathway is activated. As a result, the GFP reporter gene expression under the control of CRE is up-regulated, which can be easily detected via monitoring the corresponding fluorescence signal.

In some embodiments, the library of candidate polypeptides is expressed from a viral vector, e.g., a lentiviral vector. In these methods, a library of vectors (e.g., lentiviral vectors) encoding the combinatorial library of polypeptides can first be introduced into a virus production cell line (e.g., HEK293T) to provide a library of polypeptide-encoding viruses. The virus production cell line can be the same as (e.g., the HEK293T cell as exemplified herein) or different from the host cell for selection of receptor agonists. Vectors expressing the target receptor (e.g., GLP-1R) and a detectable reporter (e.g., GFP gene under the control of a regulatory sequence that is responsive to activation of the target receptor) can be introduced into the host cell. Upon transfecting the viruses into the host cell expressing the target receptor, the library of peptides will be expressed and become co-localized to the membrane with the receptor. This allows for autocrine selection from the polypeptide library of modulators (e.g., agonists) of the membrane bound GPCR. Once a candidate polypeptide is identified that activates the target receptor, the corresponding polynucleotide sequence encoding the candidate polypeptide can be isolated, amplified and re-cloned into the expression vector to provide enriched libraries of candidate polypeptides. Such enriched candidate library can be employed in the next rounds of agonist selection, as exemplified herein for selection of GLP-1R agonists.

In some embodiments for selecting GLP-1R agonists, the candidate polypeptide library can comprise fusion polypeptides which contain a first randomized peptide sequence that is fused to a second peptide or polypeptide capable of binding to the GLP-1 receptor ectodomain. In some embodiments, the peptide or polypeptide capable of binding the GLP-1 receptor ectodomain is derived from an Ex4 sequence or GLP-1 sequence discussed herein. For example, the peptide can be an N-terminal truncated exendin-4 sequence. The exendin-4 sequence can have a deletion of at least 4, 6, 8, 10, 15, 20 or more residues truncated at its N-terminus. In some embodiments, the N-terminal truncated exendin-4 has its 8 N-terminal residues replaced by the randomized peptide. The exendin-4 sequence can alternatively or additionally have deletion of at least 1 or more residues at the C-terminus (e.g., deletions of 9 residues). In some embodiments, the N-terminal truncated exendin-4 consists of a sequence corresponding to residues 9-30 of Ex4 (Ex4 (9-30)). Other N-terminal and/or C-terminal truncated exendin-4 sequences can also be used in the construction of the fusion peptides. In addition to exendin-4 sequences, the randomized sequences can also be appended to other peptides or polypeptides (e.g., GLP-1 sequences) in constructing the peptide libraries of the invention.

Suitable host cells or cell lines for expressing the polypeptide library and the target receptor include the HEK293T cell exemplified herein and many other cell lines well known in the art, e.g., HEK293, CHO, AtT20, BV2, and N18 cell lines. In some embodiments, the chosen host cell for the selection does not endogenously express the target GPCR receptor. For example, the HEK293T cell line exemplified herein for selecting GLP-1R agonists is not known to have endogenous GLP-1R expression. Further guidance on choosing appropriate host cells for examining GPCR signaling activities are provided in the art, e.g., Saito and Civelli, Int. Rev. Neurobiol. 2005; 65:179-209; and Chung et al., Br. J. Pharmacol. 2008; 153(Suppl 1): S339-S346. Construction of reporter cell line expressing a target receptor, expression of the peptide library in the cell line, and selection from the library of modulators (e.g., agonists) of the target receptor can be performed with standard procedures well known in the art or the specific exemplifications described herein.

IV. Polypeptide Agonists of the Glucagon-Like Peptide 1 Receptor (GLP-1R)

The invention provides novel polypeptide or peptide agonists of the glucagon-like peptide 1 receptor (GLP-1R). These polypeptides are identified or derived from randomized polypeptide sequences described herein, and are capable of specifically activating one or more signaling pathways mediated by GLP-1R, e.g., insulin biosynthesis and release. Typically, the randomized polypeptides of the invention contain a randomized peptide that is fused at its C-terminus to a second peptide that is capable of binding to the ectodomain of GLP-1R. The randomized peptide usually has an amino acid sequence that falls under a sequence formula of XXXXXXX (SEQ ID NO: 1), CXXXXXCXX (SEQ ID NO:2) or CXXXXCXXX (SEQ ID NO:3). As detailed in the Examples herein, the randomized polypeptides comprising the randomized sequence of CXXXXX-CXX (SEQ ID NO:2) or CXXXXCXXX (SEQ ID NO:3) can become cyclic due to the existence of the two cysteine residues. Identified from combinatorial libraries of such randomized polypeptides, GLP-1R agonists of the invention are all capable of activating GLP-1R mediated signaling activities.

Specific examples of the randomized peptides exemplified herein include, e.g., ACCIDSVCVI (SEQ ID NO:4), CCIDSVCVI (SEQ ID NO:22), VCPDCQV (SEQ ID NO:5), ACSYMIDCVL (SEQ ID NO:6), CSYMIDCVL (SEQ ID NO:23), ACYVKFPCDI (SEQ ID NO:7), CYVK-FPCDI (SEQ ID NO:24), ELVDNAV (SEQ ID NO:8), ACALEVDCAI (SEQ ID NO:9), CALEVDCAI (SEQ ID NO:25), ACSHSGFCVL (SEQ ID NO:10), CSHSGFCVL (SEQ ID NO:26), ACHDRVDCLV (SEQ ID NO:11), CHDRVDCLV (SEQ ID NO:27), ACSCYGYCAT (SEQ ID NO: 12), CSCYGYCAT (SEQ ID NO:28), ACGW-CGECTV (SEQ ID NO:13), CGWCGECTV (SEQ ID NO:29), VMIDQRL (SEQ ID NO:14), ACRVDQRCFW (SEQ ID NO:15), CRVDQRCFW (SEQ ID NO:30), ACCVCFTCVF (SEQ ID NO:16), and CCVCFTCVF (SEQ ID NO:31). In addition to these specific peptide sequences, conservatively modified variants or substantially identical sequences can also be used in the GLP-1R agonist polypeptides of the invention.

The second peptide can be any peptide or polypeptide that is capable of binding to the ectodomain of the GLP-1 receptor. The GLP-1R domain structure and its binding to GLP-1 or Ex4 have been well characterized in the art. See, e.g., Underwood et al., J. Biol. Chem. 2010, 285:723-730; Donnelly, Br. J. Pharmacol. 2012, 166:27-41; and Patterson et al., Mol. Metab. 2013, 2, 86-91. Peptides or proteins (including antibodies) that bind to the ectodomain of GLP-1R can be readily engineered and selected via standard protocols well known in the art. For example, they can be identified by selection of phage displayed- or yeast displayed combinatorial libraries of peptides or antibodies. In addition, many peptides or polypeptides that can bind to the extracellular domain of the receptor are also known, e.g., peptides derived from GLP-1, exendin-4, glucagon or oxyntomodulin. See, e.g., Garber, A. J. Expert Opin. Investig. Drugs 2012, 21, 45-57; Madsbad et al., Diabetes Obes. Metab. 2011, 13, 394-407; Patterson et al., Mol. Metab. 2013, 2, 86-91; Ghatei et al., J. Clin. Endocrinol. Metab. 57:488-495, 1983; and Drucker et al., Nat. Clin. Pract. Endocrinol. Metab. 1:22-31, 2005.

Any of these GLP-1R binding peptides or polypeptides can be employed in the present invention. In some embodiments, the second peptide is derived from an Ex4 sequence. Exendin-4 is a 39 amino acid peptide agonist of the glucagon-like peptide 1 (GLP-1) receptor, HGEGT FTSDL SKQME EEAVR LFIEW LKNGG PSSGA PPPS (SEQ ID NO:40) (Eng et al., J. Biol. Chem. 267:7402-5, 1992). In some embodiments, the second peptide can be derived from human oxyntomodulin sequence. Oxyntomodulin is a naturally occurring 37-amino acid peptide hormone found in the colon. Oxyntomodulin is known to bind both the GLP-1 receptor and the glucagon receptor.

Some embodiments of the invention utilizes an N-terminal truncated Ex4 sequence, e.g., with 4, 5, 6, 7, 8, 9, or more residues deleted at the N-terminus. A specific example of such Ex4 peptides is Ex4 (9-39), which has a sequence of DLS KQMEE EAVRL FIEWL KNGGP SSGAP PPS (SEQ ID NO: 17). The Ex4 derived peptides can additionally contain deletions at its C-terminus, e.g., with truncation of up to 9 C-terminal residues (the C-terminal Trp cage). An example of such Ex4 derived peptides with truncations at both the N- and C-termini is the Ex4 (9-30) peptide, which has a sequence of DLS KQMEE EAVRL FIEWL KNGG)

(SEQ ID NO:38). In some other embodiments, the second peptide is derived from GLP-1 sequence, e.g., an N-terminal truncated human GLP-1 sequence DVSSY LEGQA AKEFI AWLVK GR (SEQ ID NO:18) or DVSSY LEGQA AKEFI AWLVK GRG (SEQ ID NO:39).

In various embodiments, the N-terminal randomized or diversified first peptide can be fused to the C-terminal GPL-1R binding second peptide via a linker sequence in order enhance flexibility of the fusion polypeptide. For example, as exemplified in SEQ ID NOs:32-37, the two portions of the GLP-1R agonist peptides of the invention can be linked via two Gly residues.

As detailed in the Examples below, the N-terminal sequence (the "first peptide") of the specific GLP-1R agonist polypeptides exemplified herein (e.g., SEQ ID NOs:4-16 and 22-31) were selected from random sequences based on the activity to activate GLP-1R signaling pathways. The N-terminal sequence (the "first peptide") of the GLP-1R agonists of the invention can include or consist of a sequence that is identical or substantially identical to any of these specifically exemplified sequences. It can also include or consist of a sequence that is identical to any of these exemplified sequences except for conservative substitutions at one or more amino acid residues. In some other embodiments, the N-terminal sequence (the "first peptide") of the GLP-1R agonists of the invention can contain or consists of at least 4, 5, 6, 7, 8, or more contiguous amino acid residues shown in any one of SEQ ID NOs:4-16 and 22-31. Similarly, the C-terminal and GLP-1R binding portion (the "second peptide") of the GLP-1R agonists of the invention can include or consist of a sequence that is identical or substantially identical to any of the Ex4- or GLP-1-derived peptides sequences exemplified herein (e.g., SEQ ID NOs:17, 18, 38 and 39) or other GLP-1R binding peptides or polypeptides known in the art. It can also contain or consist of an active variant or functional derivative of the exemplified or known GLP-1R binding peptides. In some embodiments, the C-terminal portion (the "second peptide") of the GLP-1R agonists of the invention can include or consist of a sequence that is identical to one of the exemplified or known GLP-1R binding peptides except for conservative substitutions at one or more residues.

GLP-1R agonists identified from the fusion polypeptides containing the N-terminal diversified or randomized sequence and the C-terminal anchor or binding sequence are all capable of activating the GLP-1R. Typically, the fusion GLP-1R agonists of the invention contain at least 15, 20, 25, 30, 35, 40, 45, 50, 75, 100, 200, 300 or more amino acid residues in length. Some of the peptides or polypeptides contain from about 30 amino acid residues to about 100 amino acid residues. Some specific examples of the GLP-1R agonist polypeptides of the invention include Peptide 2 which has a sequence of VCPDCQV-GGDLS KQMEE EAVRL FIEWL KNGGP SSGAP PPS (SEQ ID NO:32); GLP-1 tailed Peptide 2 which has the Ex4 (9-39) sequence replaced by the GLP-1 C terminal sequence VCPDCQV-GGDVS SYLEG QAAK EFIAW LVKGR G (SEQ ID NO:33); Peptide 1 which has a sequence of ACCID SVCVI GGDLS KQMEE EAVRL FIEWL KNGGP SSGAP PPS (SEQ ID NO:34); Peptide 3 which has a sequence of ACSYMIDCVL-GGDLS KQMEE EAVRL FIEWL KNGGP SSGAP PPS (SEQ ID NO:35); Peptide 5 which has a sequence of ELVDNAV-GGDLS KQMEE EAVRL FIEWL KNGGP SSGAP PPS (SEQ ID NO:36); and Peptide 10 which has a sequence of ACGWCGECTV-GGDLS KQMEE EAVRL FIEWL KNGGP SSGAP PPS (SEQ ID NO:37). Other than these specific GLP-1R agonist polypeptides, conservatively modified variants, molecules with substantially identical sequences, and functional derivatives or analogs of these polypeptides are also encompassed by the invention.

Some of the agonist polypeptides of the invention are biased GLP-1R agonists. Unlike the endogenous or nature ligand GLP-1 or exendin-4 which can mediate a number of downstream signaling pathways through GLP-1R, the biased agonists selectively activate only some of these pathways. For example, some of the GLP-1R agonist polypeptides of the invention can trigger G-protein activation, but do not signal through other cellular pathways such as β-arrestin upon GLP-1R activation. Also, as demonstrated herein (e.g., with Peptide 5), the biased GLP-1R agonist polypeptides of the invention can display equal or greater glucose lowering effects in mouse models of T2D while displaying weak insulin secretagogue activity when compared to the agonist exendin-4.

GLP-1R agonist polypeptides or their N-terminal sequences of the invention also include other analogs, peptidomimetic, derivatives or variants that can be generated from one of the exemplified peptides and retain the activity in activating GLP-1R mediated signaling pathways. Unless otherwise noted, these peptides, which are derived from the exemplified GLP-1R agonist polypeptides or their N-terminal sequences and have similar or improved activity in activating GLP-1R signaling, are collectively termed "active variants" of the exemplified GLP-1R agonist polypeptides. Derivative compounds generated from one of the exemplified peptides can be subject to the assays described herein to identify such "active variants". In some embodiments, the derivative compounds are modified versions of the exemplified peptides which are generated by conservative amino acid substitutions. In some other embodiments, the derivative compounds are variants produced by non-conservative substitutions to the extent that that they substantially retain the activities of those peptides. Modification to a GLP-1R agonist polypeptide or its N-terminal sequence of the invention can be performed with standard techniques routinely practiced in the art (e.g., U.S. Patent Applications 20080090760 and 20060286636).

In some embodiments, the analogs or derivative compounds of an exemplified GLP-1R agonist polypeptide or its N-terminal sequence (e.g., SEQ ID NOs:32 and 36, or SEQ ID NOs:5 and 8) can contain one or more naturally occurring amino acid derivatives of the twenty standard amino acids, for example, 4-hydroxyproline, 5-hydroxylysine, 3-methylhistidine, homoserine, ornithine or carboxyglutamate, and can include amino acids that are not linked by polypeptide bonds. Similarly, they can also be cyclic polypeptides and other conformationally constrained structures. Methods for modifying a polypeptide to generate analogs and derivatives are well known in the art, e.g., Roberts and Vellaccio, *The Peptides: Analysis, Synthesis, Biology*, Eds. Gross and Meinhofer, Vol. 5, p. 341, Academic Press, Inc., New York, N.Y. (1983); and *Burger's Medicinal Chemistry and Drug Discovery*, Ed. Manfred E. Wolff, Ch. 15, pp. 619-620, John Wiley & Sons Inc., New York, N.Y. (1995).

Some other derivative compounds of the exemplified GLP-1R agonist polypeptides or their N-terminal sequences are peptidomimetics. Peptidomimetics based on a GLP-1R agonist polypeptide or polypeptide (e.g., SEQ ID NOs:32 and 36, or SEQ ID NOs:5 and 8) substantially retain the activities of the reference polypeptide. They include chemically modified polypeptides, polypeptide-like molecules containing non-naturally occurring amino acids, peptoids and the like, have a structure substantially the same as the reference polypeptides upon which the peptidomimetic is derived (see, for example, Burger's Medicinal Chemistry and Drug Discovery, 1995, supra). For example, the peptidomimetics can have one or more residues chemically derivatized by reaction of a functional side group. In addition to side group derivatizations, a chemical derivative can have one or more backbone modifications including alpha-amino substitutions such as N-methyl, N-ethyl, N-propyl and the like, and alpha-carbonyl substitutions such as thioester, thioamide, guanidino and the like. Typically, a peptidomimetic shows a considerable degree of structural identity when compared to the reference polypeptide and exhibits characteristics which are recognizable or known as being derived from or related to the reference polypeptide. Peptidomimetics include, for example, organic structures which exhibit similar properties such as charge and charge spacing characteristics of the reference polypeptide. Peptidomimetics also can include constrained structures so as to maintain optimal spacing and charge interactions of the amino acid functional groups.

In some embodiments, derivative compounds of the exemplified GLP-1R agonist polypeptides (e.g., Peptide 2 or Peptide 5) or their N-terminal sequences can contain modifications within the sequence, such as, modification by terminal-NH2 acylation, e.g., acetylation, or thioglycolic acid amidation, by terminal-carboxylamidation, e.g., with ammonia, methylamine, and the like terminal modifications. One can also modify the amino and/or carboxy termini of the polypeptides described herein. Terminal modifications are useful to reduce susceptibility by proteinase digestion and renal clearance, and therefore can serve to prolong half-life of the polypeptides in solution, particularly in biological fluids where proteases may be present. Amino terminus modifications include methylation (e.g., —NHCH$_3$ or —N(CH$_3$)$_2$), acetylation (e.g., with acetic acid or a halogenated derivative thereof such as a-chloroacetic acid, a-bromoacetic acid, or a-iodoacetic acid), adding a benzyloxycarbonyl (Cbz) group, or blocking the amino terminus with any blocking group containing a carboxylate functionality defined by RCOO— or sulfonyl functionality defined by R—SO$_2$—, where R is selected from the group consisting of alkyl, aryl, heteroaryl, alkyl aryl, and the like, and similar groups. One can also incorporate a desamino acid at the N-terminus (so that there is no N-terminal amino group) to decrease susceptibility to proteases or to restrict the conformation of the peptide compound. In some embodiments, the N-terminus is acetylated with acetic acid or acetic anhydride. In some embodiments, the exemplified GLP-1R agonist polypeptides can be modified by PEGylation with polyethylene glycol (PEG) polymer.

Carboxy terminus modifications include replacing the free acid with a carboxamide group or forming a cyclic lactam at the carboxy terminus to introduce structural constraints. One can also cyclize the peptides described herein, or incorporate a desamino or descarboxy residue at the termini of the peptide, so that there is no terminal amino or carboxyl group, to decrease susceptibility to proteases or to restrict the conformation of the peptide. Methods of circular peptide synthesis are known in the art, for example, in U.S. Patent Application No. 20090035814; and Muralidharan and Muir, Nat. Methods, 3:429-38, 2006. C-terminal functional groups of the peptides described herein include amide, amide lower alkyl, amide di(lower alkyl), lower alkoxy, hydroxy, and carboxy, and the lower ester derivatives thereof, and the pharmaceutically acceptable salts thereof.

Some other embodiments of the invention are directed to fusion molecules that are composed of an exemplified GLP-1R agonist polypeptide and a fusion partner. The fusion partner can be any molecule or moiety that can improve or enhance the biological, pharmacokinetics, or pharmacodynamics properties of the GLP-1R agonist polypeptide. In some of these embodiments, the GLP-1R agonist polypeptide can be fused to the Fc domain of an IgG. Fusion with an Fc-domain provides a number of beneficial biological and pharmacological properties. For example, the presence of the Fc domain can markedly increase the plasma half-life of the hybrid molecule, which prolongs therapeutic activity, owing to its interaction with the salvage neonatal Fc-receptor, as well as to the slower renal clearance for larger sized molecules. The attached Fc domain also enables the molecules to interact with Fc-receptors (FcRs) found on immune cells, a feature that is particularly important for their use in oncological therapies and vaccines. As the Fc domain folds independently, it can improve the solubility and stability of the fused GLP-1R agonist polypeptide both in vitro and in vivo. Further, the Fc region allows for easy cost-effective purification by protein-G/A affinity chromatography during manufacture. The GLP-1R agonist polypeptide can be fused with an Fc domain at either its N-terminus or C-terminus.

Hybrid or fusion molecules containing a GLP-1R agonist polypeptide of the invention and a fusion partner such as Fc domain can be readily generated in accordance with standard recombination techniques, routinely practiced protein synthesis methods or the protocols described herein. As exemplification, a fusion polypeptide derived from Peptide 5 fused to an Fc domain at the C-terminus (P5-Fc fusion) is disclosed herein. This fusion polypeptide has a sequence of ELVDNAVGGDLSKQMEEEAVRLFIEWLKNGGPSS-GAPPPS-ASEPKSCDKTHTCPPCPAPELLGGPSVFLFP-PKPKDTLMISRTPEVTCVVVDVSHEDP EVKFN-WYVDGVEVHNAKTKPREEQYNSTYRVVSVLTVL HQDWLNGKEYKCKVSN KALPAPIEKTISKAK-GQPREPQVYTLPPSRDELTKNQVSLTCLVKGFYPS-DIAVEWES NGQPENNYKTTPPVLDSDGSFFLYSKLT-VDKSRWQQGNVFSCSVMHEALHNHYTQ KSLSLSPGK (SEQ ID NO:45). In some embodiments, a polynucleotide for expression the Fc-containing fusion polypeptide can additionally contain a sequence encoding a signal peptide to facilitate translocation and secretion. For example, the IL-2 signal peptide (SEQ ID NO:44) can be present at the N-terminus of the Fc-containing fusion polypeptide. As demonstrated herein (see, e.g., Example 6), the Fc-containing fusion GLP-1R agonist polypeptide displayed enhanced pharmacodynamics in lowering blood glucose levels, significantly decreased food intake and body weight, and restored insulin sensitivity in diabetic mice.

The GLP-1R agonist polypeptides (e.g., Peptide 5 or Peptide 2) or their N-terminal sequences described herein also serve as structural models for non-peptidic compounds with similar biological activity. There are a variety of techniques available for constructing compounds with the same or similar desired biological activity as the GLP-1R agonist polypeptides, but with more favorable activity with respect to solubility, stability, and susceptibility to hydrolysis and proteolysis. See, e.g., Morgan and Gainor, Ann. Rep. Med. Chem. 24:243-252, 1989. These techniques include, but are not limited to, replacing the peptide backbone with a backbone composed of phosphonates, amidates, carbamates, sulfonamides, secondary amines, and N-methylamino acids.

The GLP-1R agonist polypeptides or polypeptides described herein, including variants and derivatives thereof, can be chemically synthesized and purified by standard chemical or biochemical methods that are well known in the art. Some of the methods for generating analog or derivative compounds of the GLP-1R agonist polypeptides are described herein. Other methods that may be employed for producing the GLP-1R agonist peptides or polypeptides of the invention and their derivative compounds, e.g., solid phase peptide synthesis. Commercial peptide synthesizing machines are available for solid phase peptide synthesis. For example, the Advanced Chemtech Model 396 Multiple Peptide Synthesizer and an Applied Biosystems Model 432A Peptide synthesizer are suitable. There are commercial companies that make custom synthetic peptides to order, e.g., Abbiotec, Abgent, AnaSpec Global Peptide Services, LLC., Invitrogen, and rPeptide, LLC.

In some embodiments, the GLP-1R agonist peptides or polypeptides (e.g., SEQ ID NOs:34 and 36, or SEQ ID NOs:4 and 8) and derivatives thereof are synthesized and purified by molecular methods that are well known in the art. Recombinant production of the agonist polypeptides can be performed in a variety of protein expression systems using host cells selected from the group consisting of mammalian cell lines, insect cell lines, yeast, bacteria, and plant cells. In these methods, polynucleotide sequences encoding the GLP-1R agonist peptides or polypeptides (e.g., peptide shown in SEQ ID NOs:4 and 8, or polypeptide sequences shown in SEQ ID NOs:32 and 36) are usually linked to an appropriate promoter in protein expression vectors or viral vectors. The expression constructs can further comprise a secretory sequence to assist purification of the peptide from the cell culture medium. The host cells to which the vectors are introduced can be any of a variety of expression host cells well known in the art, e.g., bacteria (e.g., *E. coli*), yeast cell, or mammalian cells. In some embodiments, recombinant vector carrying the polynucleotide encoding a GLP-1R agonist polypeptide can also be used for further molecular modifications such as site-directed mutagenesis for a GLP-1R agonist polypeptide and/or to reduce the immunogenic properties of the peptide or improve protein expression in heterologous expression systems. In some related embodiments, the invention provides isolated or substantially purified polynucleotides (DNA or RNA) which encode the GLP-1R agonist peptides or polypeptides described herein (e.g., Peptide 5 or Peptide 2). Expression vectors and engineered host cells harboring the vectors for expressing polynucleotides encoding the polypeptides are also provided in the invention.

V. Therapeutic Applications by Enhancing Insulin and Glucose Homeostasis

The GLP-1R agonists of the invention exhibit G protein biased signaling properties. As demonstrated herein with animal models of T2D, administration of such a GLP-1R agonist (e.g., P5 or P5-Fc) lead to improved glucose homeostasis and enhanced insulin sensitivity. Treatment with P5 or P5-Fc also significantly decreased glycated HbA1c levels in the diabetic mice. In experimental models of T2D/obesity, alteration in the intestinal barrier leads to increased intestinal permeability, facilitating the infiltration of microbiome-derived lipopolysaccharide to the bloodstream a phenomenon also referred to as metabolic endotoxemia (ME). ME can trigger inflammation resulting in organ damage. The size of the small and large bowel were increased in the P5-Fc treated obese mice (FIG. 20), indicating that P5-Fc displays intestinotrophic activity and restores the 'gut barrier' function that is compromised in T2D/obesity. Additionally, as described herein, chronic treatment with the GLP-1R agonists of the invention (e.g., P5-Fc) significantly decreased food intake and body weight of the treated mice, indicating their utility in treating not only diabetes but also obesity.

The invention accordingly provides methods for enhancing insulin sensitivity, reducing blood glucose level, and/or promoting insulin secretion in a subject. Some of these methods are directed to treating or correcting pathophysiology associated with T2D in a subject. Some of the methods are directed to treating obesity by chronic administration of a GLP-1R agonist of the invention to decrease food intake and body weight in a subject. In some related embodiments, the invention provides methods for activating a signaling pathway mediated by GLP-1R in a cell. Examples of the signaling pathways include insulin biosynthesis and release. The cell can be, e.g., a pancreatic β-cell. Typically, the methods are used for in vivo, e.g., to activate the signaling pathway in a cell that is present inside a subject. Thus, some methods of the invention are directed to treating subjects suffering from or at risk of developing diabetes or other metabolic disorders that are associated with or mediated by abnormal insulin synthesis and blood glucose levels. In all of these therapeutic applications of the invention, the subject can be one who is afflicted with or at risk of developing a disease or disorder that is characterized by high blood glucose and low insulin levels. For example, the subject can be one who has developed or is predisposed to develop diabetes (esp. type 2 diabetes), obesity, non-alcoholic fatty liver disease (NAFLD), non-alcoholic steatohepatitis (NASH) or atherosclerosis. In some embodiments, the subject to be treated can be one who is afflicted with a disorder in the central nervous system, e.g., stroke, Alzheimer disease, Parkinson disease, substance addiction, and etc.

Diseases or disorders associated with or mediated by high blood glucose and low insulin levels can be any conditions that are caused by or manifested with abnormal insulin release and biosynthesis. Insulin release and biosynthesis is an important biological pathway that can be activated by GLP-1R. In general, carbohydrate metabolism is regulated through the antagonistic action of two polypeptide hormones: glucagon and insulin. The former stimulates the breakdown of glycogen, particularly in the liver, resulting in elevated glucose levels in the blood, whereas insulin has the opposite effect by increasing the conversion of glucose into glycogen in liver and muscle. A number of external signals can release insulin, including an increase in plasma glucose. In response to an elevation in glucose, there is a biphasic release of insulin. There is an initial rapid phase due to the release of preformed granules, which is then followed by a smaller but more prolonged release. This latter phase results from a glucose-dependent increase in the induction and synthesis of insulin. Therefore glucose regulates both the release and the biosynthesis of insulin.

By lowering blood glucose, increasing insulin levels and insulin sensitivity, the GLP-1R agonist peptides or polypeptides of the invention find various therapeutic applications. A great number of diseases and conditions characterized by high blood glucose, decreased insulin sensitivity, and/or low insulin levels are amenable to treatment or prevention with methods and compositions of the present invention. Such diseases include, but are not limited to diabetes, hyperglycemia, genetic and diet-induced obesity, glycogen storage disease, and cardiovascular diseases. For example, the peptides can be employed to treat insulin deficiency in subjects with diabetes mellitus, including both Type I and Type II diabetes. In Type I diabetes, the body produces little or no insulin. It is characterized by a sudden onset of symptoms. It is called insulin-dependent diabetes because people who develop this type need to have daily injections of insulin. Brittle diabetics are a subgroup of Type I where patients have frequent and rapid swings of blood sugar levels between hyperglycemia (a condition where there is too much glucose or sugar in the blood) and hypoglycemia (a condition where there are abnormally low levels of glucose or sugar in the blood). These patients may require several injections of different types of insulin during the day to keep the blood sugar level within a fairly normal range. Type II diabetes is considered a milder form of diabetes because of its slow onset (sometimes developing over the course of several years) and because it usually can be controlled with diet and oral medication. The consequences of uncontrolled and untreated Type II diabetes, however, are just as serious as those for Type I. This form is also called non-insulin-dependent diabetes, a term that is somewhat misleading. Many people with Type II diabetes can control the condition with diet and oral medications. However, insulin injections are sometimes necessary if treatment with diet and oral medication is not working. In various embodiments, the GLP-1R agonist polypeptides or peptides of the invention can be used to treat or prevent the development of diabetes (Type I and Type II) and hyperglycemia in a subject.

Obesity in humans and rodents is also commonly associated with insulin resistance. Before the development of diabetes, many obese patients develop a peripheral resistance to the actions of insulin. It was suggested that increased activities of key enzymes of pathways normally depressed by insulin contributes to insulin-resistance in obesity (Belfiore et al., Int. J. Obes. 3:301-23, 1979). This failure of insulin to depress enzymes of catabolic pathways manifests itself in enhanced basal lipolysis in adipose tissue, increased amino acid release from muscle, and elevation in the activity of key gluconeogenic enzymes in the liver. The GLP-1R agonist peptides of the invention can be employed to treat or prevent such disorders and conditions.

Similarly, the GLP-1R agonist polypeptides of the invention are also useful to treat glycogen storage diseases. Glycogen metabolism in the liver plays a major role in the homeostatic regulation of blood glucose levels. Glycogen storage diseases are known to be the result of genetic defects within the group of enzymes and transport proteins required by glycogen metabolism. Glycogen storage disease Type Ia (GSD, also known as von Gierke disease) is defined as the deficiency of glucose-6-phosphatase which is normally present in liver, kidney, and intestine. Thus, the GLP-1R agonists of the invention can be employed to treat subjects with these diseases.

In some therapeutic applications of the present invention, therapeutic effects are monitored by measuring circulating glucose level or insulin level. The measurement can be taken in the subject before and/or after administering a GLP-1R agonist polypeptide of the invention. Only routinely practiced methods are involved in monitoring blood glucose level and insulin level. For example, glucose level in the subject can be measured with methods well known in the art. For example, blood glucose levels can be measured very simply and quickly with many commercially available blood glucose testing kits.

VI. Pharmaceutical Compositions

The GLP-1R agonists of the invention can be directly administered under sterile conditions to the subject to be treated. The polypeptides can be administered alone or as the active ingredient of a pharmaceutical composition. Therapeutic composition of the present invention can be combined with or used in association with other therapeutic agents. For example, a subject may be treated with a compound along with other conventional anti-diabetes drugs. Examples of such known anti-diabetes drugs include Actos (pioglitizone, Takeda, Eli Lilly), Avandia (rosiglitazone, Smithkline Beacham), Amaryl (glimepiride, Aventis), Glipizide Sulfonlyurea (Generic) or Glucotrol (Pfizer), Glucophage (metformin, Bristol Meyers Squibb), Glucovance (glyburide/metformin, Bristol Meyers Squibb), Glucotrol XL (glipizide extended release, Pfizer), Glyburide (Micronase; Upjohn, Glynase; Upjohn, Diabeta; Aventis), Glyset (miglitol, Pharmacia & Upjohn), Metaglip (glipizide+metformin; fixed combination tablet), Prandin (repaglinide, NOVO), Precose (acarbose, Bayer), Rezulin (troglitazone, Parke Davis), and Starlix (nateglinide, Novartis). In addition to these known anti-diabetes drugs, other example of compounds that are useful in the treatment of insulin deficiency or resistance are also described in the art, e.g., U.S. Pat. Nos. 6,110,962, 6,399,745, 6,521,665, 6,683,107, 6,765,021.

Pharmaceutical compositions of the present invention typically comprise at least one active ingredient (e.g., a GLP-1R agonist polypeptide disclosed herein) together with one or more acceptable carriers thereof. Pharmaceutically carriers enhance or stabilize the composition, or to facilitate preparation of the composition. Pharmaceutically acceptable carriers are determined in part by the particular composition being administered, as well as by the particular method used to administer the composition. They should also be both pharmaceutically and physiologically acceptable in the sense of being compatible with the other ingredients and not injurious to the subject. This carrier may take a wide variety of forms depending on the form of preparation desired for administration, e.g., oral, sublingual, rectal, nasal, or parenteral. For example, the GLP-1R agonists can be complexed with carrier proteins such as ovalbumin or serum albumin prior to their administration in order to enhance stability or pharmacological properties.

The pharmaceutical compositions of the invention can be administered to subjects in need of treatment in a variety of ways. These include both local and systemic administrations. Specific examples of routes of administration include, without limitation, oral, parenteral (including subcutaneous, intravenous, intramuscular and intraperitoneal), rectal, vaginal, dermal, transdermal (topical), transmucosal, intrathoracic, intrapulmonary and intranasal (respiratory) routes. The means of administration may be by injection, using a pump or any other appropriate mechanism.

The pharmaceutical compositions can be prepared in various forms, such as granules, tablets, pills, suppositories, capsules, suspensions, salves, lotions and the like. The concentration of therapeutically active compound in the formulation may vary from about 0.1 to 100% by weight. Therapeutic formulations are prepared by any methods well known in the art of pharmacy. The therapeutic formulations can be delivered by any effective means which could be used for treatment. See, e.g., *Goodman & Gilman's The Pharmacological Bases of Therapeutics*, Hardman et al., eds., McGraw-Hill Professional (10th ed., 2001); *Remington: The Science and Practice of Pharmacy*, Gennaro, ed., Lippincott Williams & Wilkins (20$^{th}$ ed., 2003); and *Pharmaceutical Dosage Forms and Drug Delivery Systems*, Ansel et al. (eds.), Lippincott Williams & Wilkins (7$^{th}$ ed., 1999).

The therapeutic formulations can conveniently be presented in unit dosage form and administered in a suitable therapeutic dose. A suitable therapeutic dose can be determined by any of the well-known methods such as clinical studies on mammalian species to determine maximum tolerable dose and on normal human subjects to determine safe dosage. Except under certain circumstances when higher dosages may be required, the preferred dosage of a GLP-1R agonist usually lies within the range of from about 0.001 to about 1000 mg, more usually from about 0.01 to about 500 mg per day. The dosage to be administered to a subject can be any amount appropriate to eliminate or ameliorate at least one symptom associated with the disease or disorder to be treated (e.g., diabetis or obesity). Some factors that determine appropriate dosages are well known to those of ordinary skill in the art and may be addressed with routine experimentation. For example, determination of the physicochemical, toxicological and pharmacokinetic properties may be made using standard chemical and biological assays and through the use of mathematical modeling techniques known in the chemical, pharmacological and toxicological arts. The therapeutic utility and dosing regimen may be extrapolated from the results of such techniques and through the use of appropriate pharmacokinetic and/or pharmacodynamic models. Other factors will depend on individual patient parameters including age, physical condition, size, weight, the condition being treated, the severity of the condition, and any concurrent treatment. The dosage will also depend on the polypeptide chosen (e.g., P5 or P5-Fc as exemplified herein) and whether prevention or treatment is to be achieved, and if the polypeptide is chemically modified. Such factors can be readily determined by the animal models described herein or other animal models or test systems that are available in the art.

The GLP-1R agonist polypeptides or peptides provided herein can be administered in a single dose, in multiple doses, in a continuous or intermittent manner, depending, for example, upon the recipient's physiological condition, whether the purpose of the administration is therapeutic or prophylactic, and other factors known to skilled practitioners. The administration of the therapeutic agents can be essentially continuous over a pre-selected period of time or may be in a series of spaced doses. For example, therapeutic composition containing a GLP-1R agonist of the invention can be administered to the subject once or multiple times (e.g., twice or three times) a day, once or multiple times every week or every two weeks, or once or several times every month. Depending on the specific subjects and the condition to be treated, the administration can last for varying length of time, e.g., a few days, a few weeks, a few months, a few years or longer. In general, the amount of a given GLP-1R agonist included in a unit dose can vary widely. Thus, the amount of the drug to be administered in a unit dosage can be, e.g., at least about 0.01 mg/kg to about 500, 750 or 1000 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. Measured alternatively, the unit dosage to be administered can be in the range of at least about 0.5 nmol/kg to about 25 or 50 mmol/kg, at least about 1 nmol/kg to about 5 or 10 mmol/kg, or at least about 2.5 nmol/kg to about 500 or 1000 nmol/kg. In addition, when the drug is administered more frequently (e.g., daily administration), a lower unit dosage may be employed. Conversely, in some chronic treatment that involve less frequent administration of the drug (e.g., weekly or biweekly administration), a higher unit dosage can be used. Further, other than a fixed dosage throughout the treatment regimen or treatment process, the subject may also be administered with varying dosages along the duration of any treatment regimen or the entire treatment process. For example, a treatment regimen can employ daily or weekly dosages that are increasingly higher as the treatment regimen progresses. Alternatively, a treatment regimen can start with a higher daily or weekly dosage at the beginning, and gradually decrease the dosage administered in the following days or weeks. In some other embodiments, a treatment process can contain multiple treatment regimens that employ differing dosages.

The preferred dosage and mode of administration of a GLP-1R agonist of the invention can vary for different subjects, depending upon factors that can be individually reviewed by the treating physician, such as the condition or conditions to be treated, the choice of composition to be administered, including the particular GLP-1R agonist, the age, weight, and response of the individual subject, the severity of the subject's symptoms, and the chosen route of administration. As a general rule, the quantity of a GLP-1R agonist administered is the smallest dosage which effectively and reliably prevents or minimizes the conditions of the subjects. Therefore, the above dosage ranges are intended to provide general guidance and support for the teachings herein, but are not intended to limit the scope of the invention.

EXAMPLES

The following examples are provided to further illustrate the invention but not to limit its scope. Other variants of the invention will be readily apparent to one of ordinary skill in the art and are encompassed by the appended claims.

Example 1 System Constructions and Selection of GLP-1R Agonist Peptides

Figure 10:
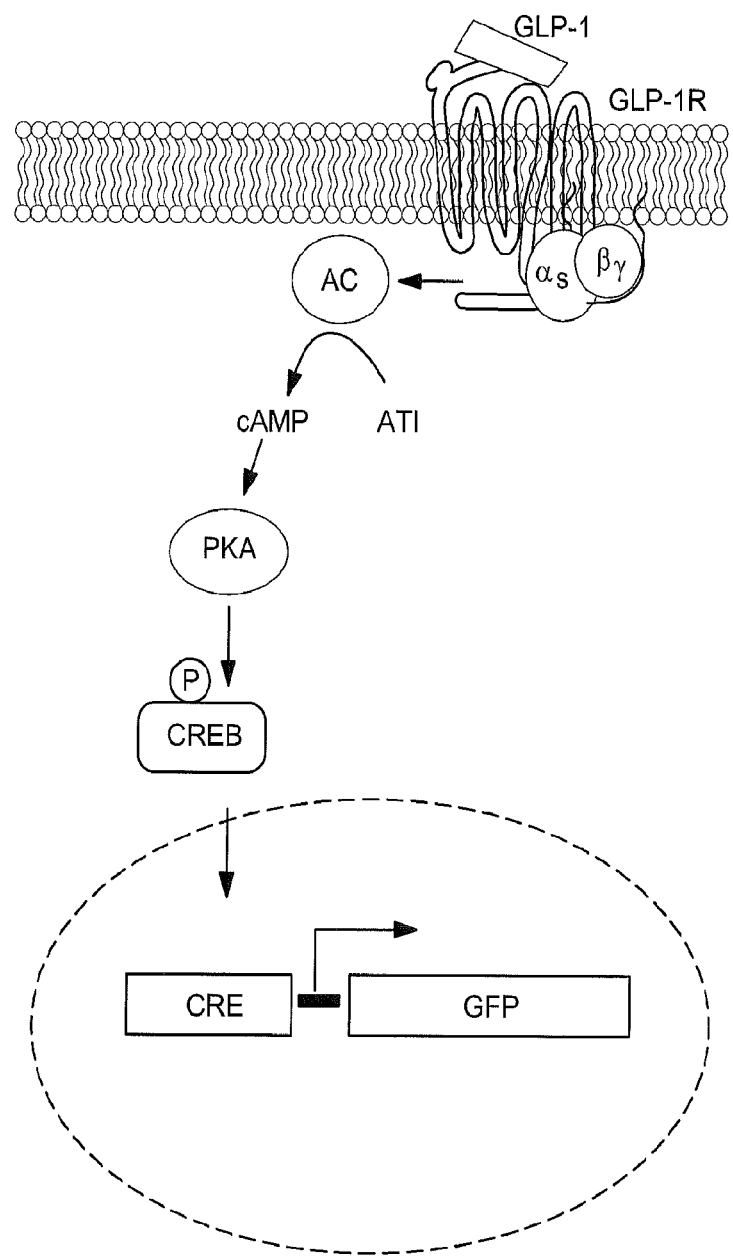
FIG. 10 shows schematically the construction of the HEK293-GLP-1R-GFP reporter cell line.

In order to identify potential G-protein biased ligands for the GLP-1R, we expressed a peptide library at the cell surface of a reporter cell line co-expressing the GLP-1R and the green fluorescent protein (GFP) (HEK293-GLP-1R-GFP) (FIG. 10). The protein expression was put under the control of CRE promoter in order to screen for peptides that induce GLP-1R mediated cAMP production. This autocrine system coupled to FACS cell sorting enable the screening of about 1 million different peptides sequences. The peptide library used in the screening was based on Exendin-4 (Ex4) which, with a full length of residues 1-39, is GLP-1R agonist. Specifically, three combinatorial peptide libraries were generated to add 7-10 amino acids to the N-terminus of a truncated Ex4 containing residues 9-39 termed "Ex4 (9-39)". In the first two libraries a randomized tetrapeptide ($CX_4C$) or pentapeptide ($CX_5C$) was inserted between IL-2 signal sequence and Ex4 (9-39) (FIG. 1a). These two libraries with cyclic peptide N terminal were designed based on the fact that many GPCR natural ligands are cyclic peptides such as calcitonin, oxytocin and somatostatin (reference: ligand based peptide design and combinatorial library to target GPCR). The third library consisted of seven random amino acids at N terminal of the exendin-4 (9-39).

In order to determine the optimal length of the linker between the Ex4 sequence and the PDGFR transmembrane anchor, we first infected HEK293-GLP-1R-GFP cells with the various constructs containing one, two or three repeats of the linker sequence (FIG. 1a). In addition, in order to control transduction efficiency, the mCherry fluorescent protein was added at the C-terminus of the PDGFR sequence (FIG. 1a). Exogenous Ex4 and membrane bound Ex4 stimulated GFP expression (FIG. 1b). Interestingly, GFP expression was found to be independent of the length of the linker between the PDGFR transmembrane domain and the peptide library (FIG. 1c). Thus, the three libraries described above were inserted upstream of single linker sequence followed by the PDGFR and the mCherry sequences. Following HEK293-GLP-1R-GFP infection, active peptides were selected after multiple rounds of enrichment using our standard protocol as described in Xie et al., Proc Natl Acad Sci USA 110, 8099-8104, 2013 (FIG. 2c). Following the first round, no significant enrichment could be detected (FIG. 2d). However, following a second round, enrichment was observed (0.31% of the population) and by the third round of selection, GFP positive cells yielded 10.6% of the cell population (FIG. 2d). Using deep sequencing, thirteen peptide sequences with frequency higher than 1% were identified as GLP-1R activating hits following the third round of selection. Notably, we identified sequence from the linear heptapeptide($X_7$) or the heptapeptide($CX_5C$) library but not from the hexapeptide library($CX_4C$). Interestingly, all the hits' sequences were unrelated to the N-terminus of the parent molecule Ex4.

Example 2 Characterization of Identified GLP-1R Agonist Peptides

To quantitatively characterize the identified hits, we constructed GLP-1 responsive reporter cell line with luciferase under control of cAMP response element (HEK293-GLP-1R-Luciferase). It was found that several peptides, including P1, P2, P5 and P10, can stimulate cAMP production.

Figure 5:
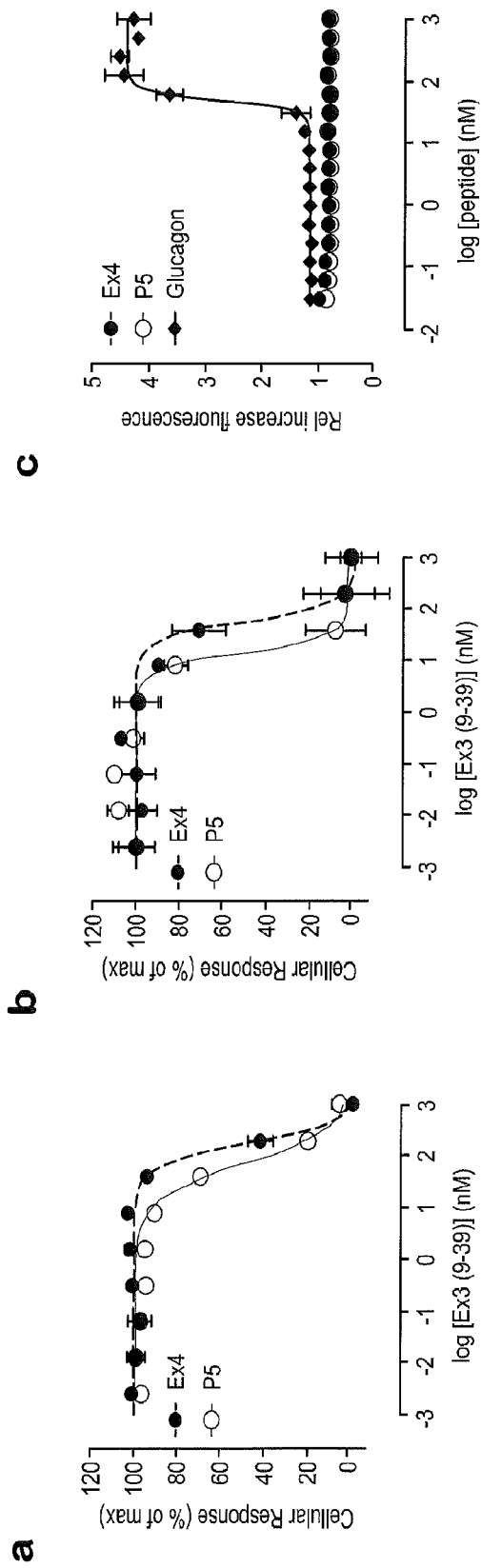
FIG. 5 shows additional in vitro pharmacological characterization of Peptide P5 selectivity. a-b, Concentration response curves for Ex9-induced decrease in cAMP production in presence of an Ec90 of P5 in CHO cells expressing the human GLP-1R (a) or in HEK293 expressing the mouse GLP-1R (b). c, Concentration response curves for glucagon-P5- and Ex4-induced calcium mobilization in CHO cells expressing the human glucagon receptor. The data are mean±SEM of typical experiment that was performed three times.

It is known that GPCR ligands can induce distinct active receptor conformations with unique downstream signal pathways profiles. In an effort to identify possible G-protein biased agonists, three distinct in vitro assays was used to characterize the relative efficacy of the identified peptides to signal though G-protein and β-arrestin. For each assay, a concentration response curve was generated, and half-maximal effective concentration (Ec50) and the maximal efficacy ($E_{max}$ (%)) relative to the reference peptide Ex4 ($E_{max}$ (%)) were determined for some of the identified GLP-1R agonist peptides (e.g., Peptides 1, 2, 3, 5 and 10). The data are shown in FIGS. 2a-2d, FIGS. 5a-5c, and Table 1. As shown in the data, one of these peptides, P5, behaved as a full agonist and displayed similar nanomolar potency as Ex4 at both the human (hGLP-1R) and mouse receptor (mGLP-1R) (FIG. 2a, 2b, Table 1). Importantly, P5-induced cAMP production was inhibited by the selective GLP-1R antagonist Ex9-39 in a concentration-dependent manner (FIG. 5a, 5b). In addition, in a HEK293 cell line expressing the human glucagon receptor, P5-induced cAMP production was negligible (FIG. 5c). These data indicated that P5 selectively interacts with the GLP-1R.

We next investigated the ability of P5 to increase intracellular $Ca^{2+}$ concentration. It was found that P5 induced a concentration-dependent increase in $[Ca^{2+}]_i$ and displayed similar potency and efficacy when compared to Ex4 (FIG. 2c, Table 1). It is known that GLP-1R also couples to β-arrestin 1 and β-arrestin 2 following activation with Ex4. Therefore, we examined P5 ability to recruit β-arrestin 1 and β-arrestin 2 using a cell-based assay based on enzyme fragment complementation. We found that P5 showed a greatly diminished efficacy ($E_{max}$=29% and 32%) and potency (Ec50=447 nM and 529 nM) for β-arrestin 1 and 2, respectively, when compared to Ex4 (Ec50=29.57 nM and 5.6 nM) (FIG. 2d, 2e). Using an equiactive comparison, we further quantified the biased agonism of P5 compared to Ex4. P5 yielded bias factors (β) of 0.9 and 1.4 for Gαs-protein over β-arrestin 1 and β-arrestin 2, respectively, and of 1.7 and 2.4 for Gαq-protein over β-arrestin 1 and for β-arrestin 2, respectively (FIG. 2f). Importantly, these values were significantly different from the bias factors obtained with the natural ligand GLP-1 (FIG. 2f), confirming that P5 has a preference for G-protein activation (referred to as G-protein bias). Thus, together these experiments revealed that P5 is an efficacious and selective G-protein biased agonist at both the human and mouse GLP-1R.

TABLE 1

In vitro activity of peptides. Characterization of the relative efficacy of the peptides to signal through Gαs-protein in human and mouse GLP-1R expressing cell lines, and through Gαq-protein, β-arrestin-1 and β-arrestin-2 in human GLP-1R expressing cell lines. EC50 values represent the concentration (nM) of peptide required to simulate half-maximum GLP-1R activation. $E_{max}$ (%) values represent the maximum activation obtained with each peptide relative to Ex4 maximum activation.

| | Gαs | | | | Gαq | | β-arrestin-1 | | β-arrestin-2 | |
|---|---|---|---|---|---|---|---|---|---|---|
| | human GLP-1R | | mouse GLP-1R | | human GLP-1R | | human GLP-1R | | human GLP-1R | |
| Peptide | EC50 (nM) | $E_{max}$ (%) | EC50 (nM) | $E_{max}$ (%) | EC50 (nM) | $E_{max}$ (%) | EC50 (nM) | $E_{max}$ (%) | EC50 (nM) | $E_{max}$ (%) |
| Ex4 | 0.091 | 100 | 0.322 | 100 | 55.132 | 100 | 29.57 | 100 | 5.615 | 100 |
| GLP-1 | 0.912 | 73 | nd | nd | 308.536 | 60 | 280.809 | 71 | 60.133 | 77 |
| P1 | 2028.000 | 14 | 542.000 | 18 | nd | nd | nd | nd | nd | nd |
| P2 | 385.600 | 51 | 364.300 | 53 | nd | nd | nd | nd | nd | nd |
| P3 | nc | nc | nc | nc | nd | nd | nd | nd | nd | nd |
| P5 | 0.852 | 102 | 0.967 | 100 | 84.94 | 113 | 447.635 | 29 | 529.723 | 32 |
| P10 | 3.200 | 11 | nc | 5 | nd | nd | nd | nd | nd | nd |

The data are means of a typical experiment that was performed three times.

Example 3 In Vivo Activities of Exemplary GLP-1R Agonist Peptide P5

Figure 3:
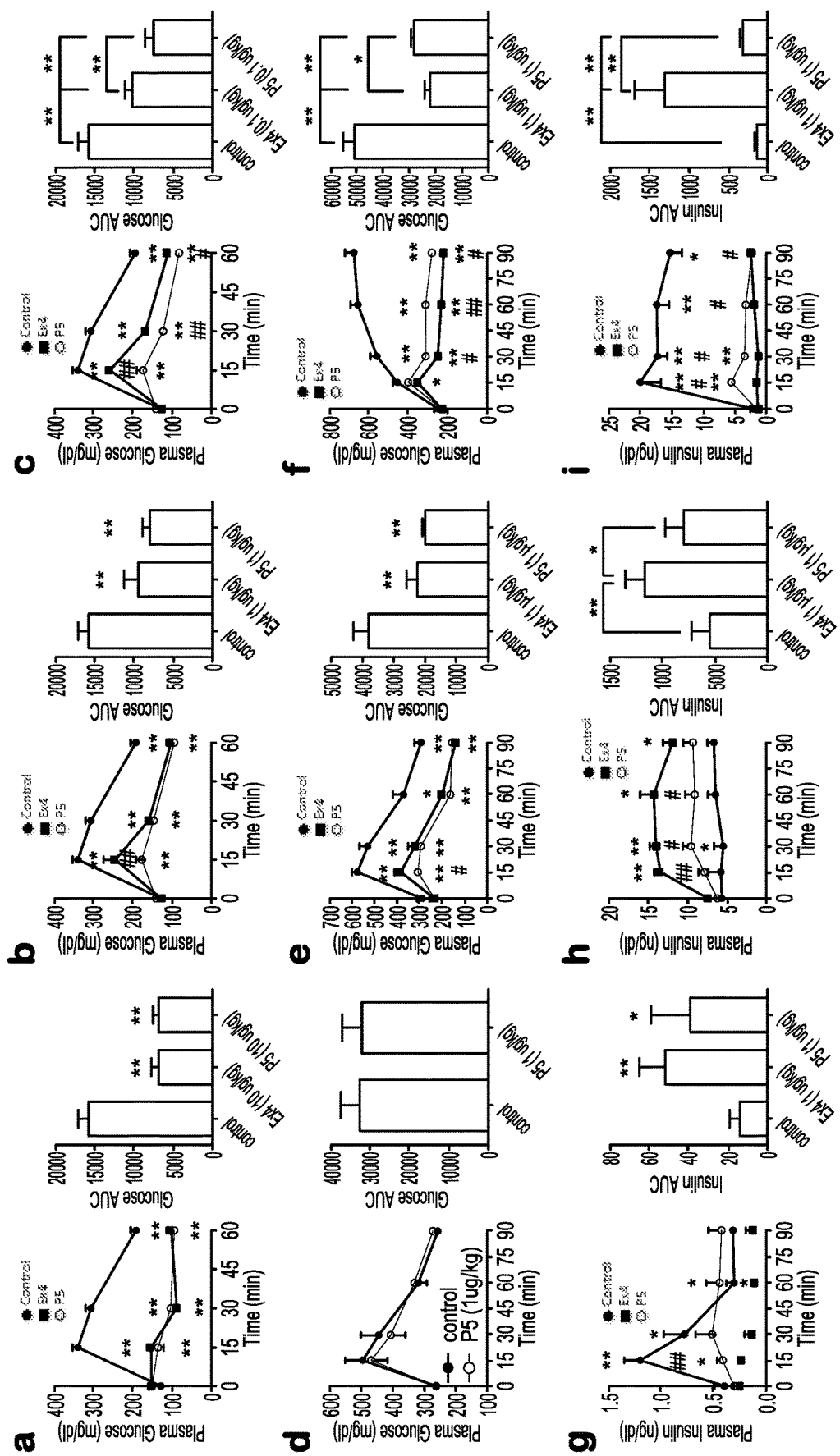
FIG. 3 shows acute P5 injection lowers glucose in diabetic mice. a-i, Intraperitoneal glucose tolerance ("insulin disposal") test; a single intraperitoneal injection of saline, Ex4 or P5, co-injected with an intraperitoneal glucose challenge (n=5). Glucose tolerance in lean mice treated with 10 μg/kg (a), 1 μg/kg (b) or 0.1 μg/kg peptides (c), in GLP-1-R KO treated with 1 μg/kg peptides (d), in ob/ob mice treated with 1 μg/kg peptides (e) and in DIO mice treated with 1 μg/kg peptides (f). g-i, Plasma insulin levels was analyzed after a single intraperitoneal co-injection of saline, 1 μg/kg of Ex4 or 1 μg/kg of P5 G-protein biased agonist with glucose challenge (n=5) in lean mice (g), in ob/ob mice (h) and in DIO mice (i). Data are mean±s.e.m. Statistic by two-tailed t-test: *$P<0.05$; **$P<0.01$, comparing saline to peptide injection; #$P<0.05$; ##$P<0.01$, comparing Ex4 to P5 injection. AUC, area under the curve.

As P5 demonstrated distinct in vitro pharmacology at the GLP-1-R, we next explored its efficacy in various mouse models of T2D. In 8 week-old lean mice fed on normal chow, a single dose injection of P5 or Ex4 significantly improved glucose tolerance at all doses tested when compared to vehicle-control mice (FIGS. 3a-3c). Interestingly, P5 dosed at 1 µg/kg$^{-1}$ lowered fasting blood glucose level with a faster onset compared to the same dose of Ex4 (FIG. 3b). Furthermore, at the lowest dose tested (0.1 µg/kg$^{-1}$), P5 showed improved efficacy at all time points compared to the equivalent dose of Ex4, and the value of area under the curve (AUC) of GTT was significantly decreased (FIG. 3c). Collectively, these data indicate that P5 at 0.1 µg/kg$^{-1}$ improved blood glucose tolerance to the same extent as a 100-fold higher dose of Ex4. P5 failed to improve glucose tolerance in the GLP-1R knockout mice, indicating that the peptide does not display any off-target effects that may contribute to its glucoregulatory activity (FIG. 3d). Together, these data indicate that in metabolically healthy lean mice, P5, a G-protein biased agonist of the GLP-1R, has a sustained and greater glucoregulatory activity compared the reference agonist Ex4.

Figure 6:
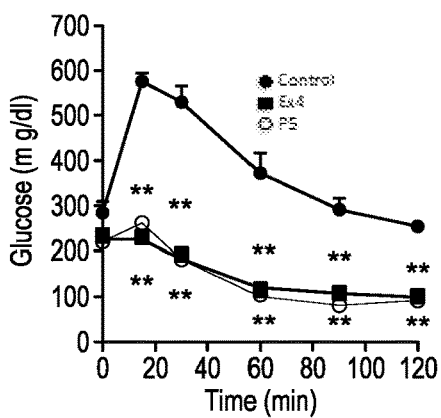
FIG. 6 displays additional results indicating effect of acute P5 injection on glycemia and insulin level in ob/ob mice. a-i, Acute treatment of male mice with P5 G-protein biased agonist. a-c, Effect on intraperitoneal glucose tolerance and plasma insulin levels following a single intraperitoneal co-injection with glucose challenge (n=5) of saline, Ex4 and P5 G-protein biased agonist. Glucose tolerance in ob/ob mice treated with 10 μg/kg (a), 0.1 μg/kg (b) (n=5). c, Plasma insulin level in ob/ob mice were analyzed after a single intraperitoneal co-injection of saline, 10 μg/kg of Ex4 or 10 μg/kg of P5 G-protein biased agonist with glucose challenge (n=5). Data are mean±s.e.m. Statistic by two-tailed t-test: *$P<0.05$; **$P<0.01$, comparing saline to peptide injection; #$P<0.05$; ##$P<0.01$, comparing Ex4 to P5 injection. AUC, area under the curve.
Figure 6:
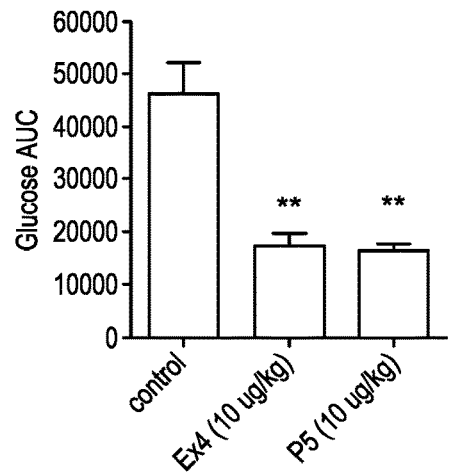
Figure 6:
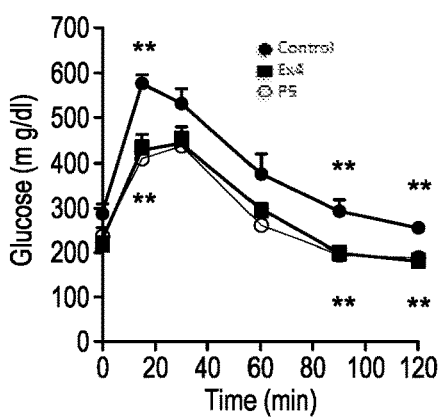
Figure 6:
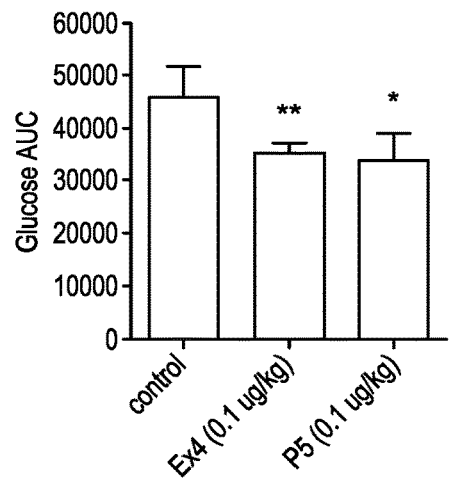
Figure 6:
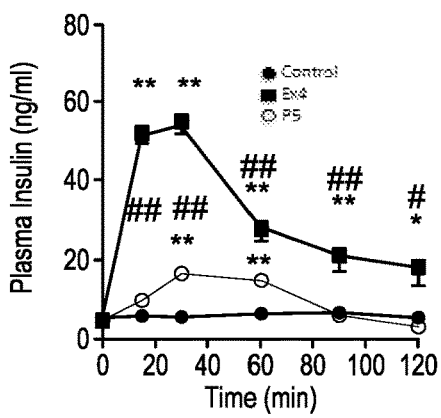
Figure 6:
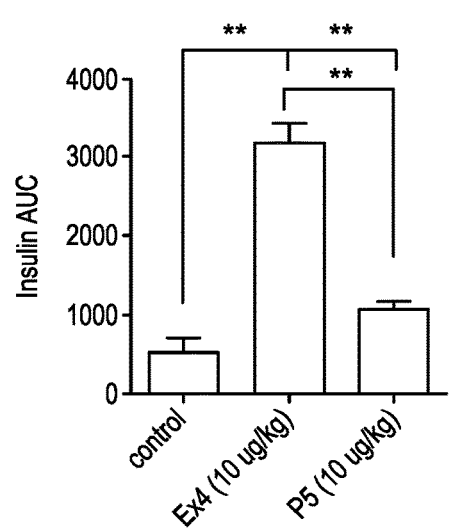

We next compared the effect of escalating doses of P5 and Ex4 in 8 week old leptin deficient ob/ob mice. Injection of P5 or Ex4 induced a reduction in blood glucose level in a dose-dependent manner (FIG. 3e, FIGS. 6a and 6b). In this mouse model of T2D, P5 treated animals also showed significantly improved glucoregulatory activity at the 15 min time point compared to Ex4 when dosed at 1 µg/kg$^{-1}$ (FIG. 3e). We further tested P5 efficacy in the diet induced obesity (DIO) mouse model of pre-type 2 diabetes. A single injection of P5 or Ex4 (1 µg/kg$^{-1}$) significantly improved glucose clearance in response to glucose challenge (FIG. 3f). However, in contrast to Ex4, P5 showed slightly reduced glucose clearance in GTT (FIG. 3f).

Since GLP-1 agonists contribute to glycemic control by potentiating glucose-dependent stimulation of insulin secretion from pancreatic β-cells, we further compared the effect P5 and Ex4 on plasma insulin level in response to glucose challenge. In lean mice fed the normal chow, P5 or Ex4 dosed at 1 µg/kg$^{-1}$ significantly increased the level of insulin compared to control mice (FIG. 3g). Surprisingly, although P5 displayed a greater glucoregulatory activity compared to Ex4 in lean mice (FIGS. 3a-3c), P5 potentiated the insulin secretory response to a less extent than Ex4 (FIG. 3e). In hyperinsulinemic ob/ob mice and DIO mice, P5 dosed at 1 µg/kg$^{-1}$ only modestly potentiated the insulin secretory response, whereas Ex4 significantly increased the level of insulin when compared to the control group (FIG. 3h). At a higher dose (10 µg/kg$^{-1}$), P5 significantly increased plasma insulin level in ob/ob mice when compared to control group. However, the insulin secretory response was significantly lower when compared to a similar dosing of Ex4 (FIG. 6c). In mice fed the high fat diet, while a single injection of P5 or Ex4 (1 µg/kg$^{-1}$) significantly increased plasma insulin level, plasma insulin level displayed significantly lower response to P5 compared to the same dose of Ex4 (FIG. 3i). These data indicate that P5, a GLP-1R G-protein biased agonist peptide, displays decreased secretagogue activity relative to the reference agonist Ex4, suggesting that in vivo, β-arrestin 1/2 signaling downstream of GLP-1R activation plays a critical role in potentiating glucose-stimulated insulin secretion (GSIS). β-arrestin 1 was found to be indispensable for the potentiating action of GLP-1 and the pituitary adenylate cyclase-activation polypeptide on GSIS in cultured pancreatic β-cells. Furthermore, it was reported that the potentiating effect of GLP-1 on GSIS was decreased in β-arrestin 2 deficient islets (Zhang et al., *Biochem Biophys Res Commun* 435, 345-349, 2013). Thus, GLP-1-R G-protein biased ligands described herein offer new and unappreciated advantages in the context of chronic treatment such as improving glycemic control while preserving pancreatic β cell function by minimizing the insulin secretory burden.

Example 4 Efficacy of Exemplary GLP-1R Agonist Peptide P5 in Chronic Treatment

Figure 4:
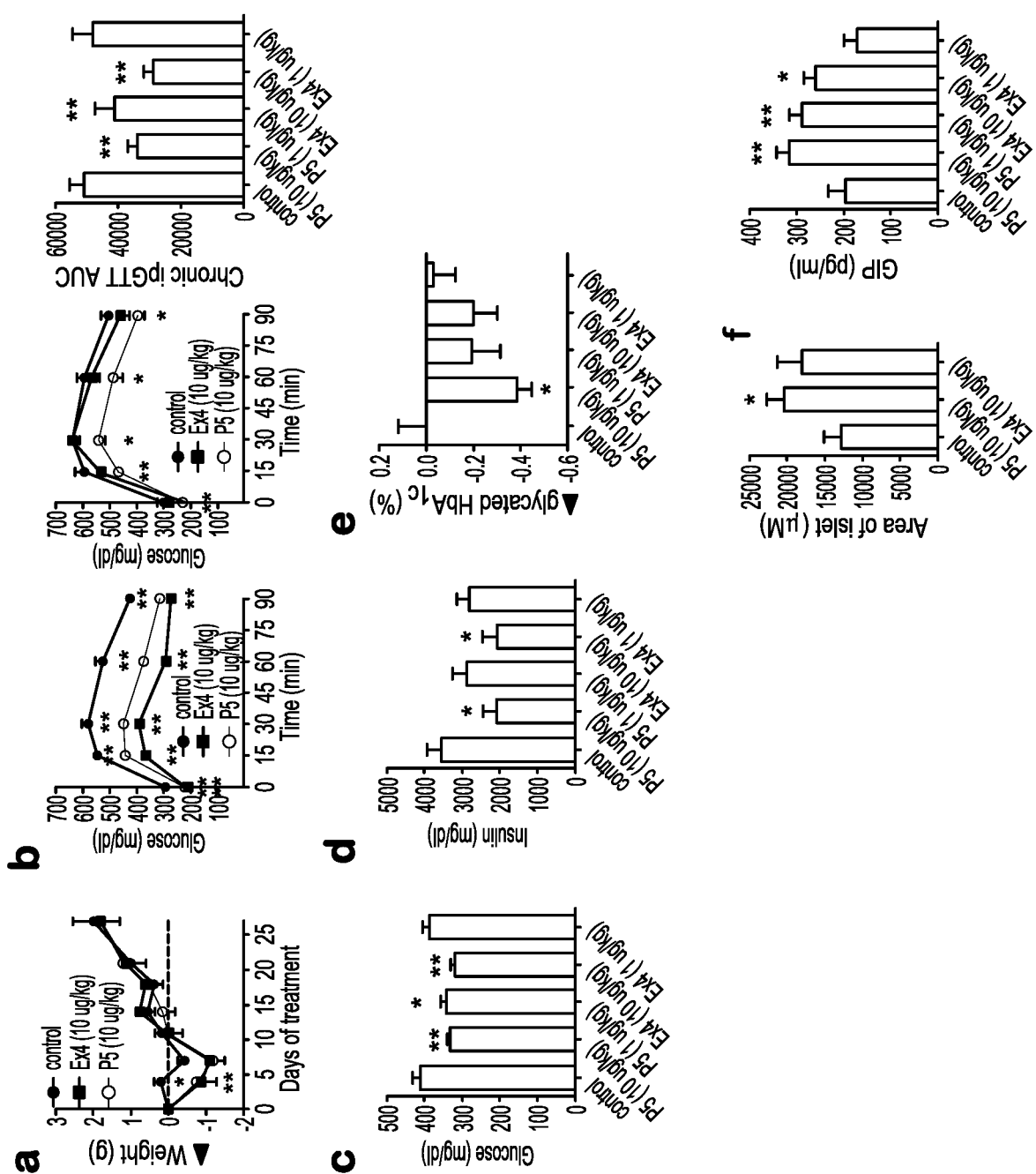
FIG. 4 shows that chronic administration of the G-protein biased GLP-1R agonist peptide P5 improves glycemic status in diabetic mice. a-g, four week of treatment of DIO male mice with daily dose of Ex4 and P5 biased agonist. Effect on body weight (a), intraperitoneal glucose tolerance (b), ad-libitum-fed plasma glucose level (c), insulin plasma level (d), HbA$_{1C}$ (e), and GIP plasma level (f) after daily subcutaneous injections of saline, Ex4 and P5 G-protein biased agonist at 1 μg/kg (lighter shade) or 10 μg/kg (darker shade). Data are mean±s.e.m. Statistic by two-tailed t-test: *$P<0.05$; **$P<0.01$, comparing saline to peptide injection. AUC, area under the curve.
Figure 7:
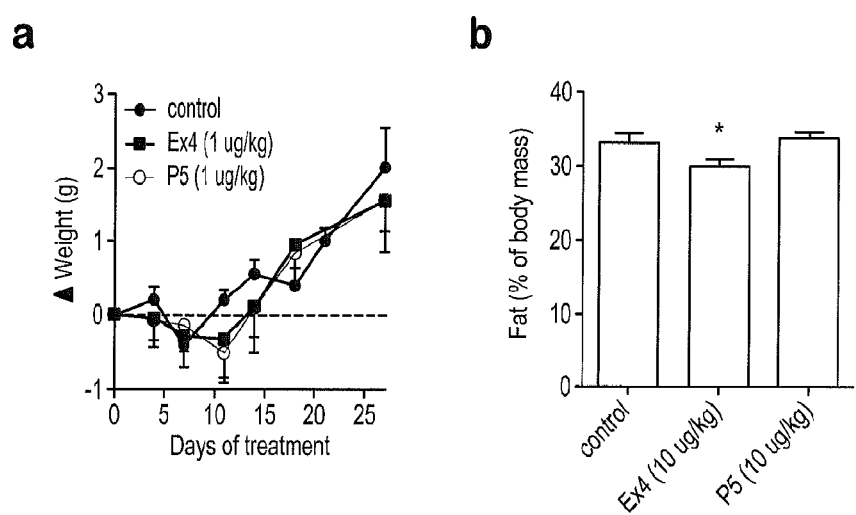
FIG. 7 displays additional results indicating that chronic administration of Peptide P5 improves glycemic status in diabetic mice independently of body weight and fat mass. a-b Four week of treatment of DIO male mice with daily dose of Ex4 and P5 biased agonist. MRI analyses of fat (a) and body weight (b) following daily subcutaneous injections of saline, Ex4 and P5 G-protein biased agonist at 10 μg/kg (n=8). Data are mean±s.e.m. Statistic by two-tailed t-test: *$P<0.05$; **$P<0.01$, comparing saline to peptide injection.
Figure 8:
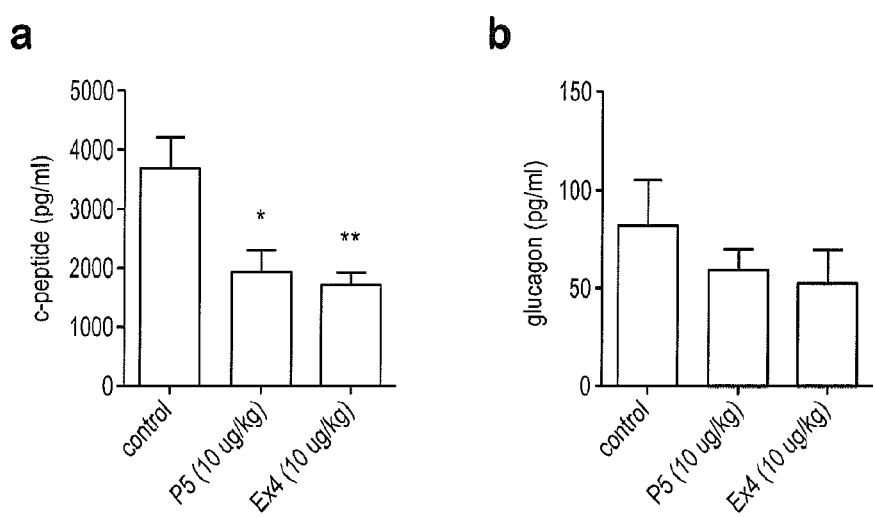
FIG. 8 displays additional results indicating effect of chronic administration of Peptide P5 on metabolic hormones in DIO mice. Four week of treatment of DIO male mice with daily dose of Ex4 and P5 biased agonist. Effects on c-peptide plasma level (a) and glucagon plasma level (b) (n=8) after daily subcutaneous injections of saline, Ex4 and P5 G-protein biased agonist at 10 μg/kg. Data are mean±s.e.m. Statistic by two-tailed t-test: *$P<0.05$; **$P<0.01$, comparing saline to peptide injection.

To determine whether metabolic improvement can be achieved by chronic treatment with the GLP-1R G-protein biased agonist, DIO mice were treated daily with escalating doses of P5 or equimolar doses of Ex4 for 4 weeks. At the highest dose studied (10 µg/kg), both P5 and Ex4, induced a modest decrease in body weight during the initial phase of treatment (FIG. 4a) whereas at the lower dose (1 µg/kg) neither P5 nor Ex4 induced weight loss (FIG. 8a). In contrast to Ex4, P5 dosed at 10 µg/kg did not affect fat mass when compared to vehicle treated animals (FIG. 7b). We next compared the outcome of chronic treatment of DIO mice with P5 and Ex4 on glucose homeostasis. Daily dosing with P5 or Ex4 at 10 µg/kg for 4 weeks, significantly lowered fasting blood glucose level (FIG. 4b). In contrast, when dosed at 1 µg/kg, only P5 significantly decreased fasting blood glucose level when compared to (FIG. 4b). In GTT after 4 week treatment, both P5 and Ex4 improved glucose tolerance when dosed daily at 10 µg/kg. When dosed at 1 µg/kg, P5 but not Ex4, improved glucose tolerance (FIG. 4b). Furthermore, the high and low doses of P5 significantly decreased ad libitum-fed blood glucose level (FIG. 4c). In contrast, Ex4 corrected non-fasting blood glucose level only at the highest dose tested (FIG. 4c). Both peptides significantly decreased the concentration of circulating insulin and c-peptide at the highest dose, which is indicative of improved insulin sensitivity (FIG. 4d, and FIG. 8a). Notably, P5 induced a dose dependent decrease in HbA$_{1c}$ (FIG. 4e). When compared to control, the mean change in HbA$_{1c}$ ranged from −0.19% to −0.38% in DIO mice treated with 1 µg/kg and 10 µg/kg of P5, respectively (FIG. 4e). The effect of P5 in lowering HbA$_{1c}$ level was superior when compared to Ex4 (−0.03% to −0.2% at 1 µg/kg and 10 µg/kg). Histological analysis of the pancreas revealed that the biased agonist preserved proper insulin immunoreactivity and significantly increased islet area (FIG. 4f).

Improved glucoregulatory efficacy of peptide P5 was also demonstrated by the circulating levels of glucagon and glucose-dependent insulinotropic polypeptide (GIP), two other enteroinsular hormones involved in the regulation of glucose homeostasis. At the highest dose, both P5 and Ex4 tend to decrease glucagon level (FIG. 8b). Interestingly, daily dosing of P5 resulted in a significant increase in circulating GIP level in a dose dependent manner (FIG. 4g). Notably, P5 efficacy to increase circulating level of GIP was superior when compared to equivalent daily doses of Ex4. Interestingly, dipeptidylpeptidase IV (DPP-IV) inhibitors, a monotherapy used to improve glycaemic control in subjects with T2D, was known to increase endogenous levels of both GLP-1 and GIP (Russell-Jones et al., *Clin. Endocrinol.* 77, 489-499, 2012). In addition, previous studies demonstrated that the simultaneous activation of the GLP-1R and the GIP-R resulted in enhanced glycemic control as well as in lower HbA1c level in human and rat, suggesting a GIP and GLP-1 synergism. Thus, the superior glycemic control observed with the G protein biased agonist may result from increased GIP level and concomitant receptor activation.

Figure 9:
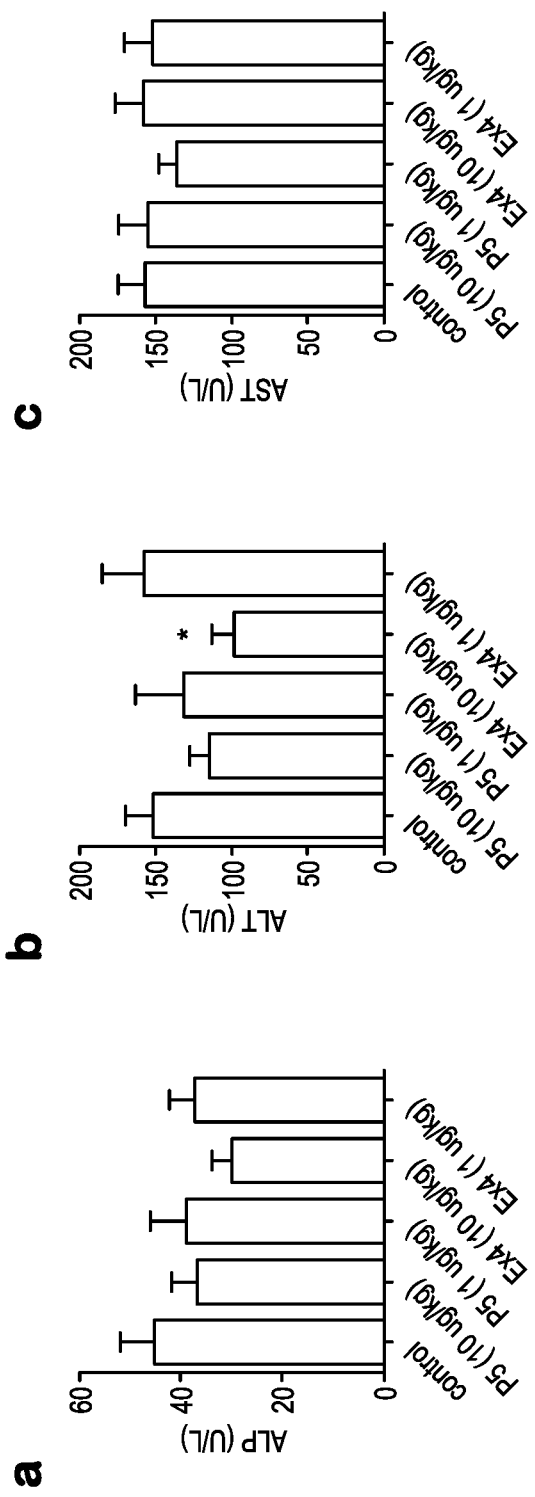
FIG. 9 displays additional results indicating effect of chronic administration of P5 G-protein biased agonist on hepatoxicity and steatosis in DIO mice. Four week of treatment of DIO male mice with daily dose of Ex4 and P5 biased agonist. Effects on plasma ALP (a), plasma ALT (b), and plasma AST (c) following daily subcutaneous injections of saline (control), Ex4 and P5 G-protein biased agonist. Data are mean±s.e.m. Statistic by two-tailed t-test: *$P<0.05$; **$P<0.01$, comparing saline to peptide injection.

We further observed that chronic treatment with P5 for 4 weeks did not induce hepatocellular toxicity as reflected by the absence of changes in plasma level of alanine aminotransferase (ALT), alkaline phosphatase (ALP), and aspartate aminotransferase (AST) (FIG. 9a-9c) and improved hepatic steatosis. In addition, the G-protein biased agonist performed equally well to reduce low-density lipoprotein levels without affecting high-density lipoprotein or triglycerides levels when compared to similar dosing of Ex4 (Table 2). Collectively, these data suggest that chronic treatment with a GLP-1R G-protein biased agonist peptide improves lipid metabolism and results in greater and sustained correction of hyperglycemia in DIO mice when compared to the reference agonist Ex4. In addition, the absence of hepatocellular toxicity suggests that even more aggressive dosing can be used in order to improve P5 in vivo efficacy.

TABLE 2

Metabolic parameters of DIO mice chronically treated with P5. Male DIO mice injected subcutaneously daily with saline (control), P5 or Ex4 for 4 weeks (n = 8).

| Treatment | Albumin g/dL | ALP U/L | ALT U/L | AST U/L | Triglycerides mg/dL | HDL mg/dL | LDL mg/dL |
|---|---|---|---|---|---|---|---|
| control | 2.3 ± 0.6 | 39 ± 22 | 151 ± 50 | 156 ± 56 | 115 ± 20 | 177 ± 27 | 29 ± 7 |
| P5 (10 ug/kg) | 2.3 ± 0.3 | 37 ± 15 | 115 ± 32 | 155 ± 50 | 125 ± 35 | 189 ± 15 | 21 ± 3* |
| Ex4 (10 ug/kg) | 2.7 ± 0.6 | 30 ± 11 | 100 ± 37* | 159 ± 49 | 120 ± 34 | 186 ± 23 | 20 ± 4* |
| P5 (1 ug/kg) | 2.3 ± 0.6 | 39 ± 22 | 132 ± 88 | 136 ± 30 | 130 ± 36 | 173 ± 34 | 26 ± 10 |
| Ex4 (1 ug/kg) | 2.5 ± 0.4 | 37 ± 16 | 158 ± 89 | 152 ± 60 | 113 ± 18 | 199 ± 31 | 26 ± 11 |

Data are mean ± s.e.m.
Statistic by two-tailed t-test:
*P < 0.05;
**P < 0.01, comparing saline to peptide injection.

Example 5 Additional Studies of GLP-1R Agonizing Activities of Other Identified Peptides As noted above for Peptide P5, other identified peptides were also tested for ability to stimulate cAMP production in a HEK293-GLP-1R-Luciferase reporter cell line. It was found that several peptides, e.g., P1, P2, and P10, all promote cAMP production. In another study, G protein bias of the peptides was tested with an hGLP-1R CRE-GFP reporter cell line and an hGLP-1R Tango reporter cell line to respectively monitor the cAMP increase and β-arrestin recruitment after GPCR activation. As shown in FIG. 1b, it was found that Peptide 1 and Peptide 2 also display G protein signaling bias relative to the GLP-1R natural ligand Ex4. In a further study, activities of the other GLP-1R agonist polypeptides of the invention were examined for their effect on insulin secretion using rat INS cell and GLP-1R-mediated ERK1/2 phosphorylation. It was found that along with Peptide 5 and Exe4, Peptide 2 is also active in the insulin secretion assay, consistent with results obtained from the other studies.

Example 6. Characterization of a GLP-1R Agonist Fused with IgG Fc Domain

A fusion polypeptide containing P5 fused at its C-terminus to an Fc domain (SEQ ID NO:45) (FIG. 12a) was produced and purified using an expression vector that was constructed via the standard protocols described herein. Briefly, DNA encoding P5 sequence was fused to 5' end of the Fc fragment by PCR. The P5-Fc fragment was inserted to an expression vector under the control of EF1a promoter. The expression plasmid was transfected to 293F cells, and the P5-Fc fusion protein was purified by protein G capture from the supernatant. Quality was analyzed by SDS-PAGE, which shows a purity of >90%. To aid the protein translocation and secretion, the coding sequence in the vector also encodes the IL-2 signal peptide sequence (SEQ ID NO:44) at the N-terminus of the P5 peptide. The purified P5-Fc fusion agonist polypeptide (SEQ ID NO:45), which does not contain the signal peptide, was then subject to various in vitro and in vivo tests for GLP-1R agonist activities.

Figure 12:
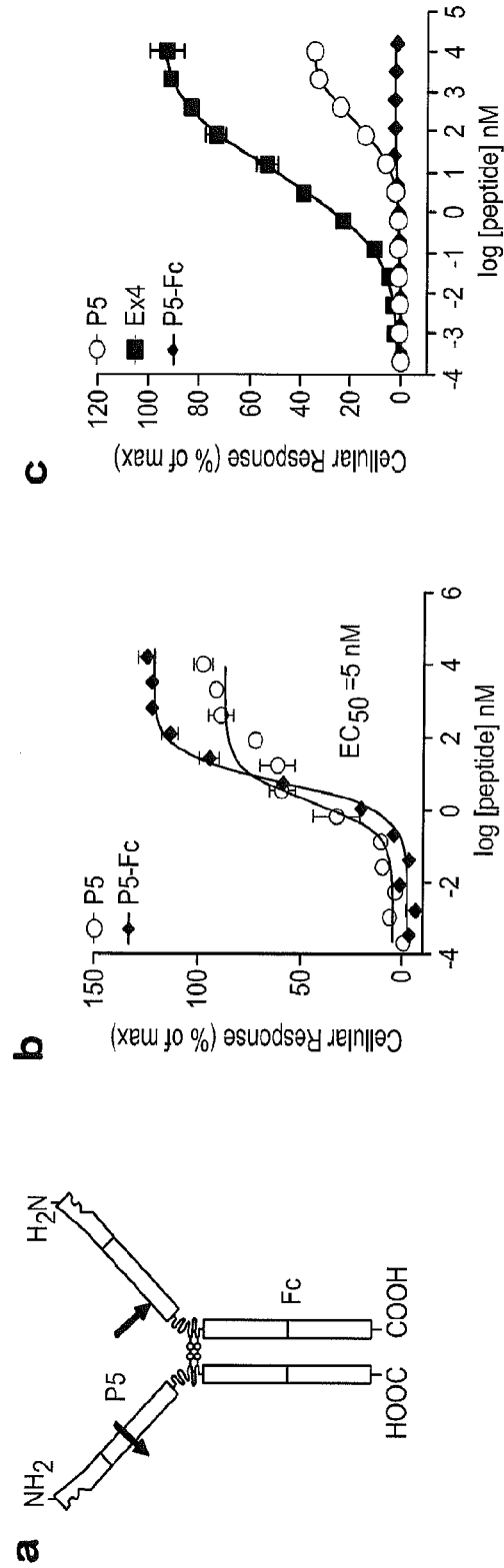
FIG. 12 shows in vitro characterization of the long acting G-protein biased agonist fusion polypeptide P5-Fc. (a) Schematic representation of P5-Fc (b) Concentration response curves for P5- and P5-Fc-induced increase in cAMP production in CHO cells expressing the human GLP-1R. (c) Concentration response curves for P5, and Ex4-induced β-arrestin-2 recruitment in CHO cells expressing the human GLP-1R.
Figure 13:
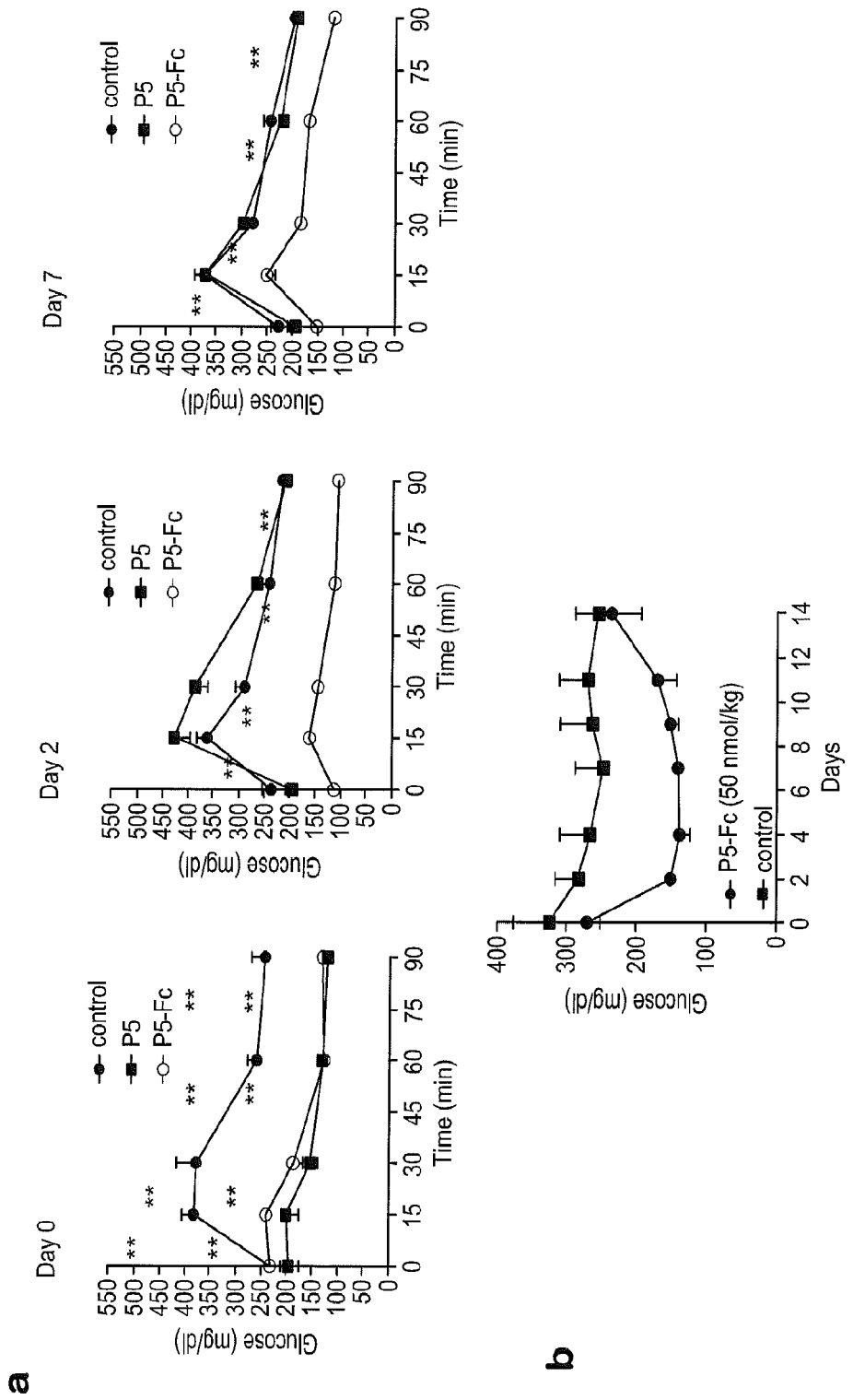
FIG. 13 shows that GLP-1R agonist fusion polypeptide P5-Fc displays enhanced pharmacodynamics. (a) Glucose tolerance tests performed either directly following a single injection of P5 (20 nmol/kg) or P5-fc (5 nmol/kg) (day 0) or two and seven days later. (b) Effect of a single injection of P5-fc (50 nmol/kg) on fed blood glucose level.

As shown in FIGS. 12b and 12c, P5-Fc stimulated cAMP production in CHO cells expressing the human GLP-1R with an $EC_{50}$ similar to P5. In addition, similarly to P5, P5-Fc showed a greatly diminished efficacy for β-arrestin recruitment. Direct comparison of the acute effects of P5 versus P5-Fc on glucose tolerance in lean mice revealed that a single dose of P5-Fc (5 nmol/kg, i.p.) significantly increases glucose tolerance up to 7 days after injection whereas a single dose of P5 (20 nmol/kg, i.p.) was effective only directly after injection (day 1) (FIG. 13a). In addition, a single injection of P5-Fc (50 nmol/kg) significantly decreased the ad libitum fed blood glucose level in DIO mice for up to 12 days (FIG. 13b). Together these data indicate that P5-Fc displays greatly enhanced pharmacodynamic when compared to P5.

Efficacy of the biased agonist P5-Fc was also tested in the diet induced obesity (DIO) mouse model of T2D. It was additionally observed that a once-weekly sub-cutaneous (s.c.) dosage of P5-Fc at either 10 nmol/kg or 50 nmol/kg could significantly reduce body weight in the DIO mice (FIG. 14a). Both P5-Fc dosages also significantly reduced fat mass, but not fluid mass or lean mass, when compared to vehicle treated control mice (FIG. 14b).

Figure 14:
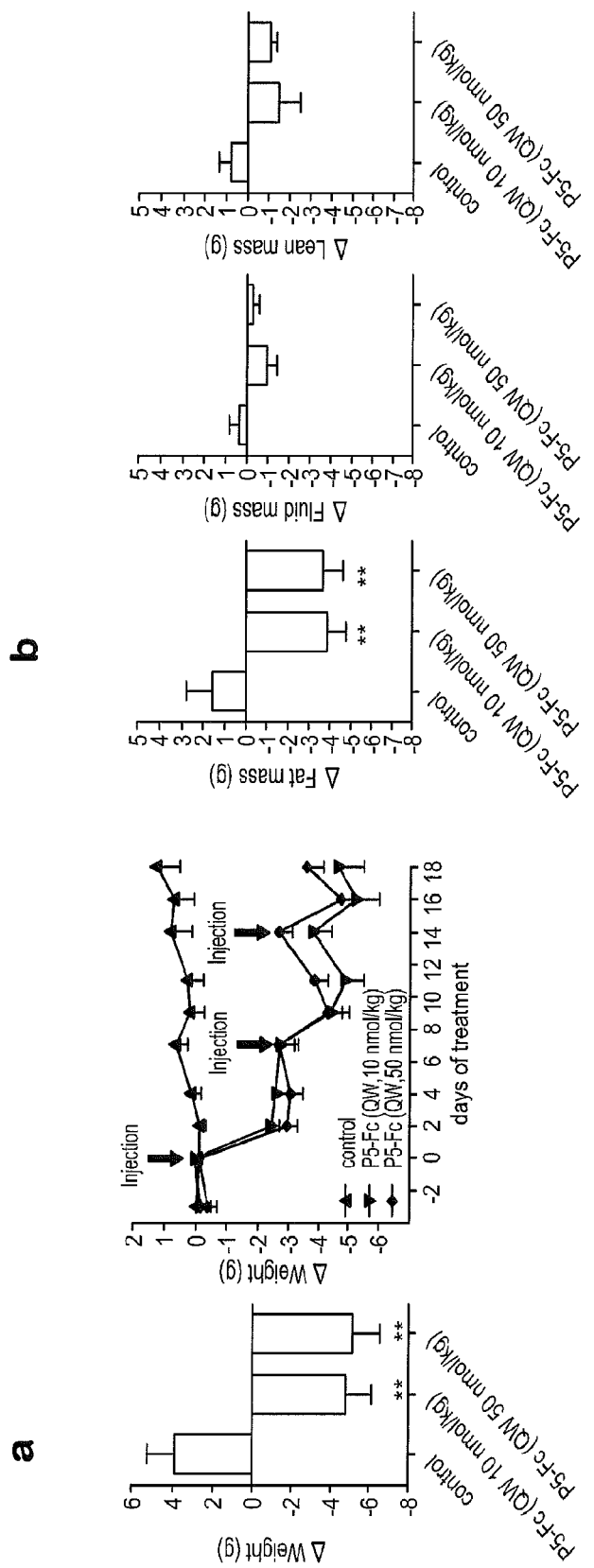
FIG. 14 shows that P5-Fc decreases body weight and fat mass in diabetic mice. (a) Effect of once-weekly administration of P5-Fc on body weight in DIO mice. (b) Effect of once-weekly administration of P5-Fc on fat mass, fluid mass and lean mass and in DIO mice (after injection 6). n=5; *, p<0.05; **, p<0.01.
Figure 15:
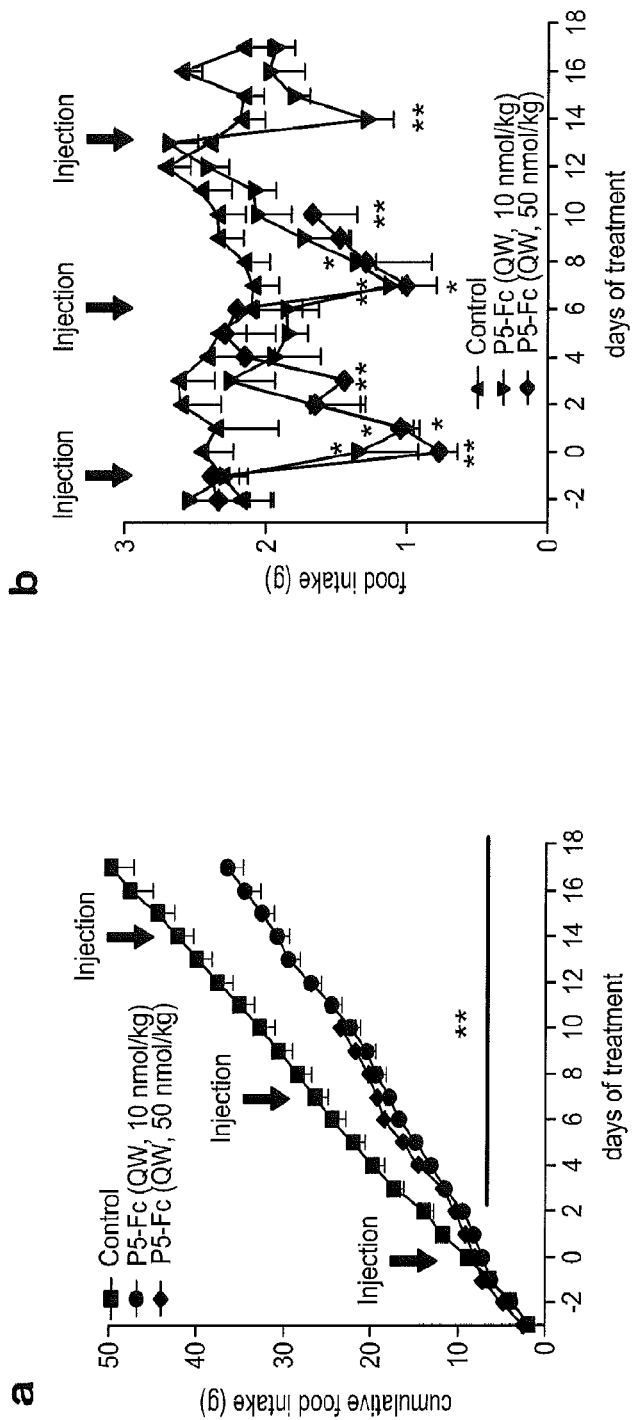
FIG. 15 shows that P5-Fc decreases food intake in diabetic mice. (a) and daily food intake (b). P5-Fc significantly decreases food intake for 2-3 days post injection. n=5; *, p<0.05; **, p<0.01.
Figure 16:
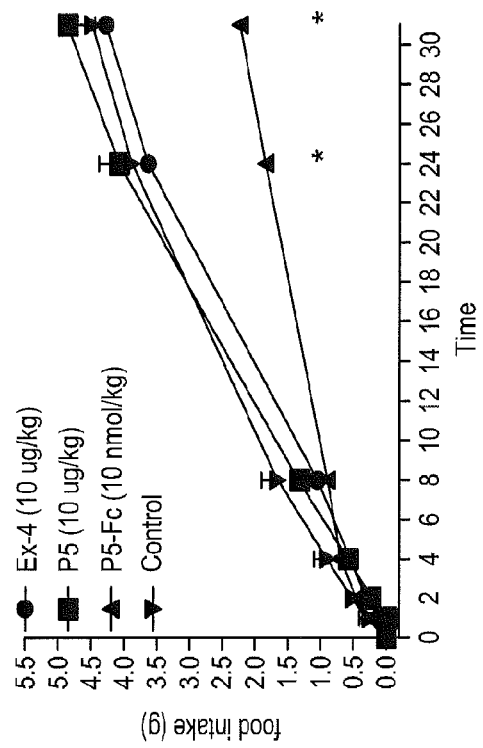
FIG. 16 shows effect of P5 and P5-Fc on reducing re-feeding of fasting mice. Male C57BL/6 mice (12-14 wk; 28-30 g) fasted for 16-18 h were injected ip with P5, P5-Fc and Ex4. Cumulative FI was measured at 1, 2, 4, 8, 24 and 31 h post-injection. n=3; *, p<0.05
Figure 16:
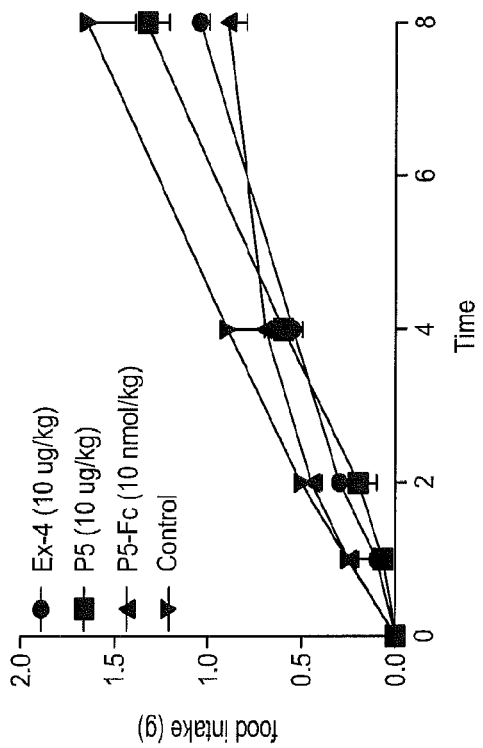

Once-weekly injection with P5-Fc (10 nmol/kg or 50 nmol/kg) was also found to decrease calories intake DIO mice (FIGS. 15a and 15b). This effect was maximal for 3 to 4 days post injection. (FIG. 15b). The effects of peripherally administrated P5-Fc, P5 and Ex on food intake were also examined in fasted male C57BL/6 mice (12-14 wk; 28-30 g). Food intake was monitored at 1, 2, 4, 8, 24 and 31 h post-injection. Administration of P5 or Ex4 produce a slight decrease in food intake for a relatively short period of time (1-4 h) when compared to vehicle treated mice (FIG. 16 right panel). However, both P5- and Ex4-treated mice ate similar amount of food over a 24h period of time. In contrast, mice given P5-fc ate significantly less than control mice after the 8 h time point (FIG. 16, left panel). These data suggest that P5-Fc induce a significant anorexic effect in mice that correlate with the weight loss observed previously (FIG. 14).

Figure 17:
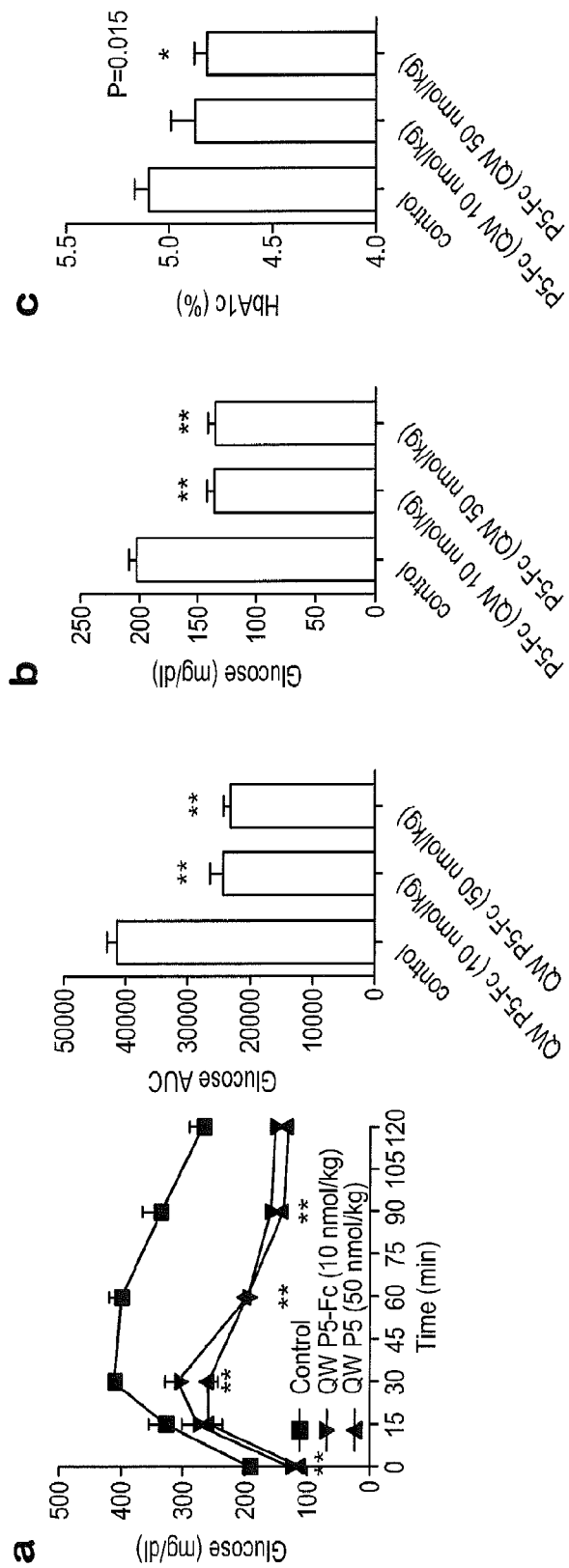
FIG. 17 shows anti-hyperglycemia efficacy of P5-Fc in treating diabetic mice. (a) Effect of once-weekly administration of P5-Fc on glucose tolerance in response to glucose challenge (one week after injection 5 and before injection 6). (b) Effect of once-weekly administration of P5-Fc on fed plasma glucose levels (one week after injection 5 and before injection 6) and (c) on HbA1c (after injection 5). n=5; *, p<0.05; **, p<0.01.

Additionally, a glucose tolerance test was performed in DIO mice treated once-weekly for 5 weeks with P5-Fc. When dosed at either 10 nmol/kg or 50 nmol/kg, P5-Fc significantly lowered fasting blood glucose levels and improved glucose tolerance compared to vehicle-treated animal (FIG. 17a). Furthermore, P5-Fc significantly decreased ad libitum-fed blood glucose level when compared to control mice (FIG. 17b). As an index of long term blood glucose regulation, we further investigated the haemoglobin (HbA1c) levels in DIO mice treated once weekly with either 10 nmol/kg or 50 nmol/kg of P5-fc for 4 weeks. P5-Fc, at the highest dose tested, produced a significant decrease in HbA1c when compared to control (FIG. 17c).

Figure 18:
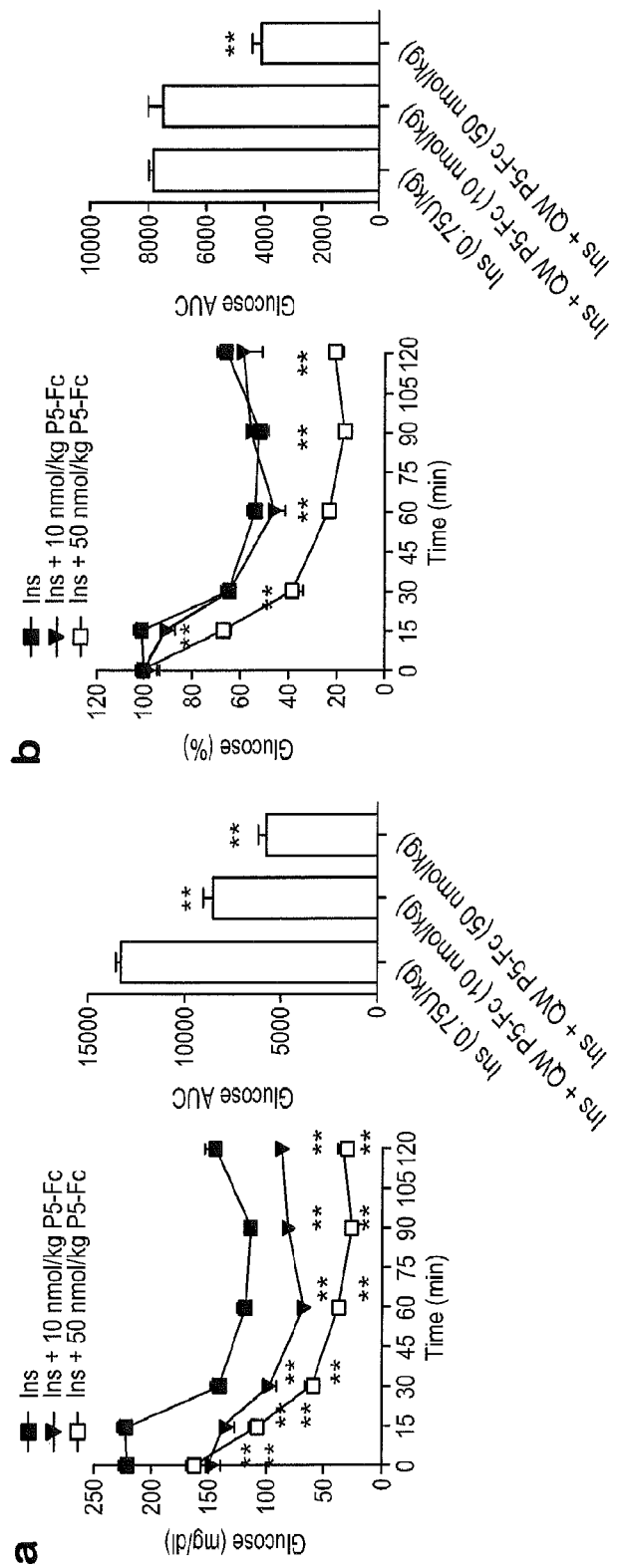
FIG. 18 shows that P5-Fc enhances insulin sensitivity in diabetic mice. (a) Effect of once-weekly administration of P5-Fc on glucose level in response to insulin injection (0.75 U/kg) (one week after injection 4 and before injection 5). (b) Data are represented as a % of basal blood glucose level for each individual group. n=5; *, p<0.05; **, p<0.01.

In addition, P5-Fc was found to restore insulin sensitivity in the diabetic DIO mice (FIG. 18). Insulin tolerance test performed in DIO mice treated once-weekly for 4 weeks with 50 nmol/kg of P5-Fc revealed a significant enhancement of the hypoglycemia response (FIGS. 18a and 18b).

Figure 19:
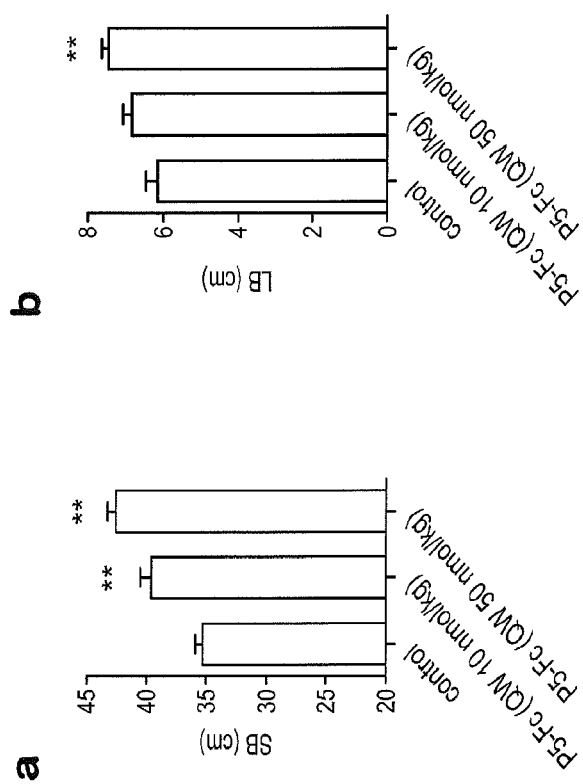
FIG. 19 shows that P5-Fc induces intestinal growth. Effect of once-weekly administration of P5-Fc on (a) small bowel (SB) length, and (b) large bowel (LB) length, n=5; *p<0.05, **, p<0.01.

Finally, once-weekly administration of P5-Fc (10 nmol/kg or 50 nmol/kg) for 5 weeks was found to display intestinotropic activity. Indeed, P5-Fc promoted intestinal growth as reflected by an increase in small bowel mass and length in P5-Fc treated animal when compared to vehicle-treated control mice. The results are shown in FIGS. 19a and 19b.

Example 7. Therapeutic Effect of P5 on Hepatic Steatosis in DIO Mice

Figure 20:
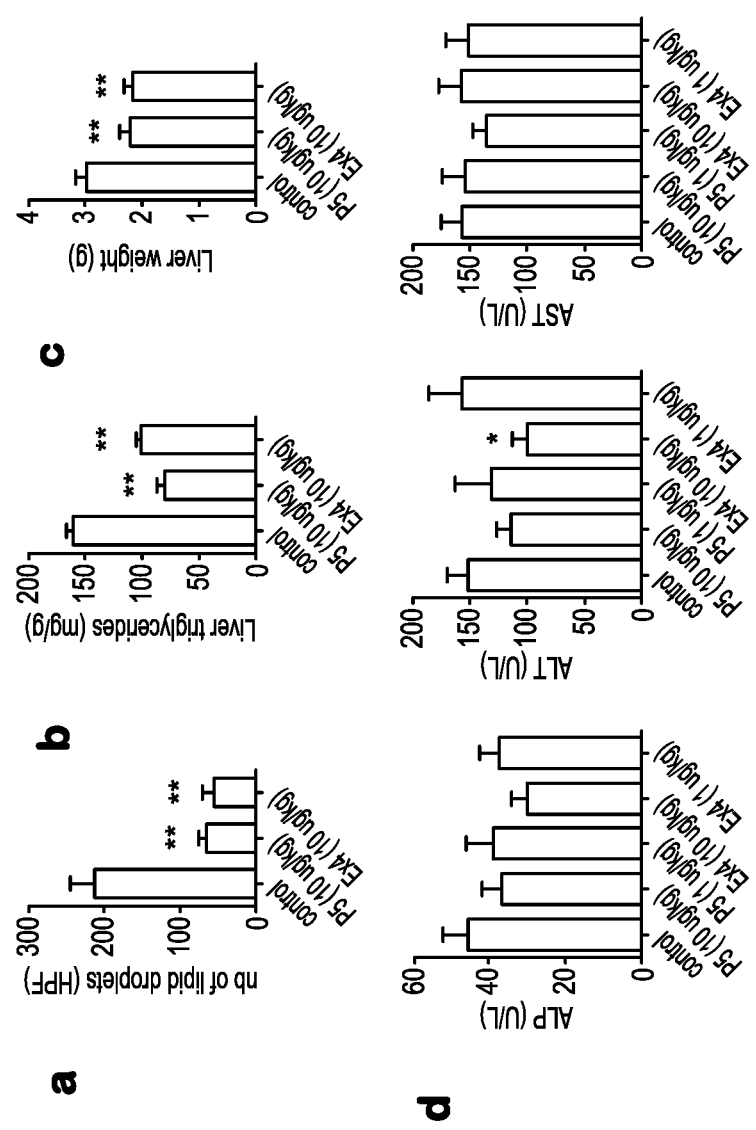
FIG. 20 shows that chronic administration of a G-protein biased agonist improves hepatic steatosis in DIO mice.

We first observed that chronic administration of the G-protein biased agonist P5 improves hepatic steatosis in DIO mice. Importantly, the observed effects were specific to the G-protein biased agonist P5 as compared to effects of Ex4. Results from this study are shown in FIG. 20. Specifically, FIG. 20a shows lipid droplet number per HPF. In the figure, section were stained with Oil Red O to investigate the presence of lipids in the liver (n=4). Scale bar, 100 µm. FIG. 20b shows liver triglyceride content normalized with liver weight, and FIG. 20c shows liver weight in DIO mice following daily subcutaneous injections of saline (control), Ex4 or P5. Additionally, effect of P5 or Ex4 on plasma ALP, ALT and AST (n=8) is shown in FIG. 20d. In the figure, data are mean±s.e.m. Statistic by two-tailed t-test: *P<0.05; **P<0.01, comparing saline to peptide injection.

Figure 21:
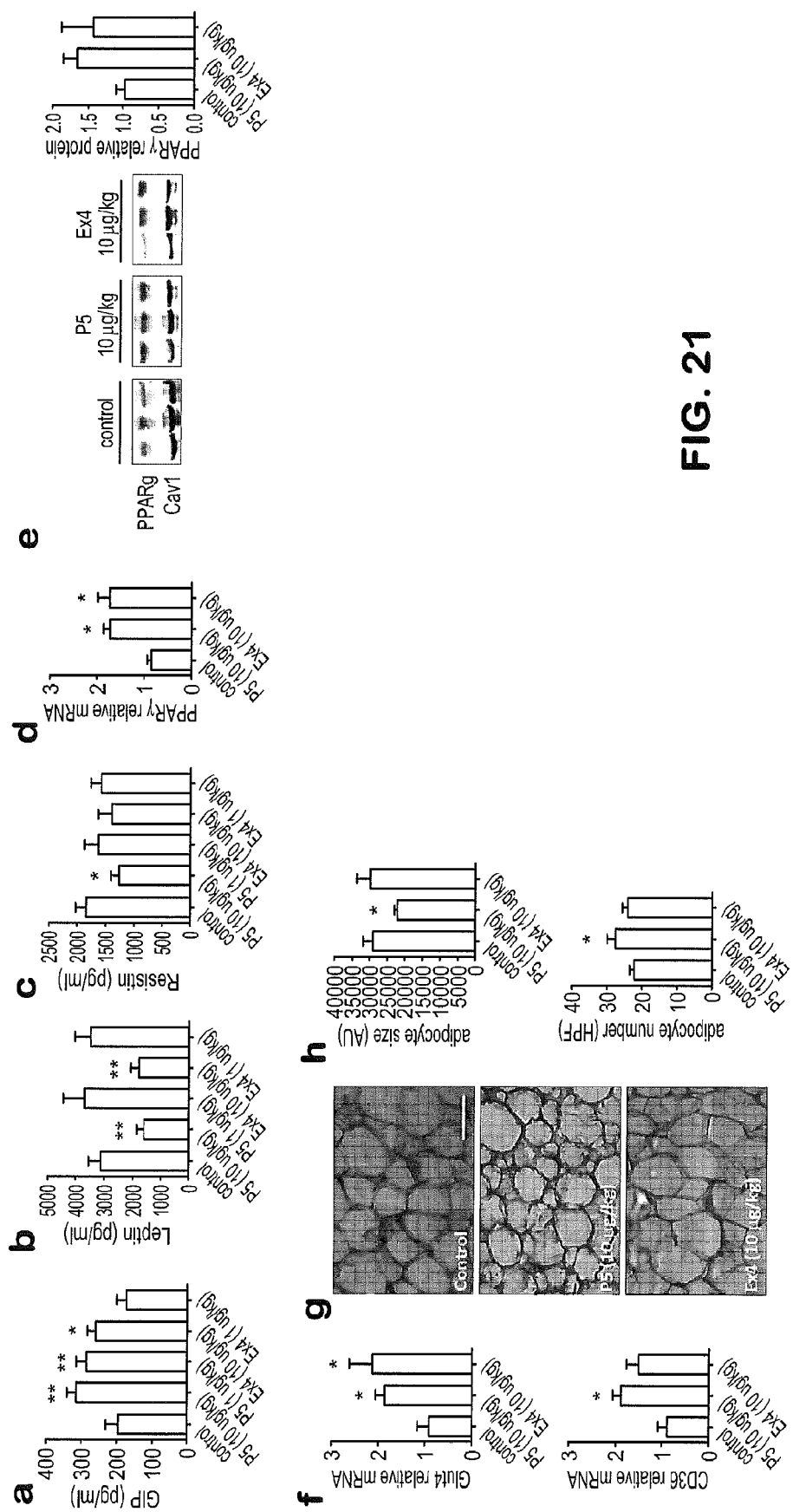
FIG. 21 shows that chronic administration of the G-protein biased agonist modulates adipogenesis and insulin sensitivity in DIO mice.

We also found that chronic administration of the G-protein biased agonist polypeptide P5 can modulate adipogenesis and insulin sensitivity in DIO mice. Results from this study are shown in FIG. 21. As indicated in the figure, the therapeutic activities of P5 are evidenced by the effect on GIP (FIG. 21a), leptin (FIG. 21b), and resistin (FIG. 21c) plasma levels following daily subcutaneous injections of saline (control), Ex4 or P5 (n=6). Also shown in the figure are real-time quantitative PCR (qPCR) analysis on the expression of the gene encoding PPARγ (n=6) (FIG. 21d) and Western Blot analysis of PPARγ protein expression in epididymal white adipose tissue (eWAT) following daily subcutaneous injections of saline (control), Ex4 or P5 (FIG. 21e). Caveolin 1 (Cav1) was used as loading control in the study. Additionally shown in the figure are qPCR analysis of eWAT mRNA expression of genes regulated by PPARγ activity, Glut4 and CD36, following daily subcutaneous injections of saline (control), Ex4 or P5 (n=6) (FIG. 21f). Representative microscopy images of eWAT from DIO mice following daily subcutaneous injections of saline (control), Ex4 or P5 are shown in FIG. 21g. In this figure, sections were stained using hematoxylin and eosin (n=4) (Scale bar, 100 µm). Finally, FIG. 21h shows adipocyte cell size and number per high-powered field (HPF) in DIO mice following daily subcutaneous injections of saline (control), Ex4 or P5.

Example 8. Materials and Methods

This Example describes some materials and methods that were employed in exemplifying the make and use of the GLP-1R agonist peptides of the invention.

Construction of Exendin-4 Based Membrane Tethered Combinatorial Peptide Library. The expression of transmembrane tethered exendin-4 was under control of EF1a in the lentiviral vector. The arrangement of genes are in the order of Interleukin 2 signal peptide at the N terminus; exendin-4; tandem repeats of the GGGGS (SEQ ID NO:43) linker; a PDGFR transmembrane region and mCherry fused at the intracellular side of the PDGFR transmembrane region. To construct exendin-4 based combinatorial peptide libraries, the exendin-4 (residues 9 to 39) antagonist as anchor site to GLP-1R extracellular domain was kept constant. Randomized peptides in the format of $X_7$, $CX_5CX_2$ and $CX_4CX_3$ (X=20 natural amino acids) were appended to the N terminus of exendin-4 (9-39) by PCR using oligonucleotides with degenerate codons. The diversity of each library is ~300 thousand members. The lentiviral library was prepared by co-transfection of HEK293T cells with the library plasmid and package plasmids. Supernatants containing virus were collected at 48 h post-transfection. The titer of lentivirus preparations was determined using Lenti-X p24 ELISAs (Clontech).

FACS Based Sorting. HEK293-GLP-1R-GFP cells were transduced with the lentivirus peptide library. Two Days post-infection, the cells were disassociated and GFP positive cells were sorted using a MoFlo Astrios fluorescence activated cell sorter (Beckman Coulter's). The peptide sequences were recovered directly from sorted cells by PCR and cloned into lentiviral vectors to construct libraries for the next round selection. Lentivirus were prepared and HEK293-GLP-1R-GFP reporter cells were transduced for the next round of sorting. Three Iterative rounds of selection were carried out.

Ion Torrent PGM Library Preparation, Template Preparation, Sequencing and Bioinformatics Analysis: Sequencing was performed on the Ion PGM System with an Ion PGM™ Sequencing 400 Kit and a 318 v2 chip for a total of 850 nucleotide flows. The standard base calling procedure was used in raw data processing. A total of 7,042,611 reads were generated with a mean read length of 489 bp. An in-house bioinformatics pipeline was developed to process and analyze the deep sequencing data of peptide libraries generated by PGM. The pipeline processing consists of four steps: each sequence read will be: (1) reformed and labeled with a unique index number; (2) aligned to the N- and C-terminal flanking regions to extract the peptide sequence; (3) compared with the template peptide sequences at the nucleotide level using a global alignment module in CLUSTALW2; and (4) translated to amino acid sequences to determine whether there are indel errors in the peptide region. The filtered and annotated peptide libraries were used for frequency analysis and clustering analysis.

Cell culture. HEK293-GLP-1R-GFP and HEK293-GLP-1R-Luciferase cells were cultured in Dulbecco's modified Eagle's medium (DMEM) supplemented with 10% fetal bovine serum and 1 mg/ml geneticin 100 µg/ml hygromycin. The stable CHO cell line expressing a functional human GLP-1R was cultured in F12 medium (Gibco) supplemented with 10% fetal bovine serum and 1 mg/ml geneticin. The HEK293 cell line expressing a functional mouse GLP-1R and the HEK293 cell line expressing a functional human glucagon receptor were cultured in Dulbecco's modified Eagle's medium (DMEM) supplemented with 10% fetal bovine serum and 1 mg/ml geneticin. PathHunter EA-β-Arrestin-1 CHO-cells and PathHunter EA-β-Arrestin-2 CHO-cells expressing the human GLP-1R (Discoverx) were cultured in F12 medium supplemented with 10% fetal bovine serum and 1 mg/ml geneticin and 100 µg/ml hygromycin.

In vitro pharmacology. cAMP HTRF-assay to measure the effects of peptide-induced GLP-1R-mediated stimulation of cAMP production was performed according to the technical manual's instruction (cAMP dynamic 2 HTRF assay kit, Cisbio). Briefly, cells were plated in 20 µl at 1000 cells per well in a 384-well plate and cultured overnight. The following day, 5 µl of peptides prepared as 5× solution in phosphate buffer saline (PBS) were added to the cells at the indicated concentrations. When GLP-1 was tested PBS was supplemented with DPP IV inhibitor (Tocris). Following 5 min incubation at room temperature, the cells were lysed in the detergent buffer containing the HTRF conjugates. The amount of cAMP in lysate samples was quantified according to the manufacturer's instruction on the Envision plate reader (PerkinElmer).

To measure the effects of peptide on intracellular calcium mobilization, CHO cells stably expressing the human GLP-1R were seeded into black-walled 384-well plates at a density of 10,000 cells per well in 20 µl of growth media and cultured overnight. The following day medium was removed and replaced with 20 µl of loading medium consisting of 1:1 (v/v) Opti-MEM:Hanks' balanced salt solution (HBSS), 2,5% (v/v) FBS, 20 mM HEPES, pH 7.4, 2.5 mM probenicid and fluorescent indicator 2 µM Fluo-4 AM (Invitrogen). Following a 60 min incubation of cells in the loading medium, cell and compound plates were placed into the FLIPR (Molecular Devices). Peptides (prepared as 5× solution in HBSS and 20 mM HEPES, pH 7.4) were added at time=10 s and changes in fluorescence were monitored over a period of 250s following excitation at a wavelength of 488 nm and detection at 510-560 nm. Relative changes over baseline (ΔF/F) were determined.

The PathHunter β-arrestin recruitment assays to measure the effects of the peptide on β-arrestin recruitment were performed according to the technical manual's instruction (PathHunter β-arrestin recruitment assay, DiscoveRx). Briefly, PathHunter EA-β-Arrestin CHO-cells expressing the GLP-1R (Discoverx) were seeded overnight in white 384-well plates at 10 000 cells/well in 20 µl of F12 medium and incubated overnight. The following day, the medium was removed and replaced with 20 µl of Opti-MEM (Gibco). Cells were then stimulated with peptides (prepared as 5× solution in PBS) or vehicle for 90 min at room temperature. Detection reagent was added, and luminescence was read on Envision plate reader. For all the cell based assays, concentration-response curves (CRC) were recorded with four wells per concentration and experiment.

The effects of peptides were calculated relative to the stimulation obtained with a maximally active concentration of exendin-4 (Ex4). CRCs were determined by nonlinear regression analysis using Prism software (GraphPad Software Inc., San Diego, Calif.). Ligand bias was determined using the equiactive comparison as described in Rajagopal et al. *Mol. Pharmacol.* 80, 367-377, 2011. A bias factor (1), which quantifies the relative engagement of one signaling state over another compared with the reference peptide, was calculated using the following equation:

$$\beta = \log\left(\left(\frac{E_{max,1}}{EC_{50,1}} \frac{EC_{50,2}}{E_{max,2}}\right)_{lig} \times \left(\frac{E_{max,2}}{EC_{50,2}} \frac{EC_{50,1}}{E_{max,1}}\right)_{ref}\right)$$

Where $E_{max}$ is the maximal effect, $EC_{50}$ is the half maximal concentration of the peptide, lig is the peptide being tested (P5 or GLP-1), ref is the reference peptide (Ex4), 1 is for values for the G-protein pathway and 2 for the β-arrestin pathway.

Animals. Mice were group-housed on a 12:12 housed light-dark cycle in a temperature-controlled environment with free access to food and water. Male C57BL/6 mice (Jackson Laboratories) and male ob/ob mice (B6.Cg-Lep$^{ob}$; Jackson Laboratories) were fed standard chow diet (Tekland Global Diet 2920X; Harlan). The mice were between the ages of 8 and 10 weeks when used in the studies. Male DIO mice, (C57BL/6 mice; Jackson Laboratories) were fed a diabetogenic diet, which is high-fat diet with 60% kcal from fat (high-fat diet (60%) diet D12492; Research Diets), for a minimum of 18 weeks before initiation of the studies and were between the ages of 6 and 7 months. GLP-1R KO mice (C57BL/6) and wild type littermate were bred in house and fed standard chow diet. All mice studies were approved by and performed according to the guidelines of the Institutional Animal Care and Use Committee of the Scripps Research Institute.

Body composition measurement. Whole body composition was measured with nuclear magnetic resonance technology (Minispec LF-50/mq 7.5 NMR; Brucker Optics)

Blood parameters. Blood was collected from tail veins or after euthanasia, using heparinized microhematocrit tubes (SafeCrit) or EDTA-coated microcuvette tubes (Sarsdedt), respectively, centrifuged at 5000 g at 4° C. for 5 min and plasma was stored at −80° C. Plasma insulin was quantified using either AlphaLISA Insulin kit (PerkinElmer) and the Mouse Metabolic Magnetic Bead Panel (Millipore). Plasma c-peptide, glucagon and GIP were measured using the Mouse Metabolic Magnetic Bead Panel. Plasma triglyceride, HDL, LDL, ALP, ALT and AST by enzymatic assays kits (Roche). HbA1C values were determined using A1CNow kit (Bayer). All assays were performed according to the manufacturer's instructions.

Glucose tolerance test (GTT). GTTs were conducted after fasting the C57BL/6 mice and the GLP-1R KO mice for 4 hours and the ob/ob mice and the DIO mice for 8 hours. Mice were injected intraperitoneally with 2 g of glucose per kilogram body weight and tail blood glucose level was monitored at the indicated time points using an AphaTRAK2 glucometer (Abbott).

Insulin tolerance test (IIT). ITTs were conducted after fasting the DIO mice for 4 hours. Mice were injected intraperitoneally with insulin (0.75 U/kg) and tail blood glucose level was monitored at the indicated time points using an AphaTRAK2 glucometer (Abbott).

Histology and immunohistochemistry. Tissues were fixed in 4% paraformaldehyde solution in phosphate buffer for 12 hours, placed in 20% sucrose overnight, embedded in Tissue-Tek (SAKURA) and stored at −80° C. until use. For immunofluorescent staining, pancreas sections (4 m) were incubated with anti-insulin antibody (abcam), followed by the appropriate secondary fluorophore-conjugated antibodies (Invitrogen) and counterstained with 4',6-diamidino-2-phenylindole (DAPI) (Sigma). Islet morphology was visualized using an Olympus Fluoview F1000 confocal laser-scanning microscope. To investigate the presence of lipids in the liver, sections (8 µM) were stained with Oil Red O (LIFELINE) in accordance with standard procedures. Small bowel length was measured under tension by suspending a 1 g weight from the distal end, prior to flushing with PBS to remove luminal content. The entire small bowel was then blotted to remove PBS before being weighed.

Statistical analysis and general methods. To enable statistical significance, five to ten Age-matched and weight matched mice cohort were randomly assigned to treatment or control groups. Statistical analysis (two-tailed student's t-test) was applied and P values lower than 0.05 was considered significant.

Construction of the GLP-1R CRE Reporter Cell Line: The human GLP-1 receptor was cloned into a lentiviral vector to express hGLP-1R under control of the human ubiquitin C promoter (UbC). The Lenti CRE Reporter lentivirus (Sabiosciences) encodes the GFP gene under the control of a minimal CMV promoter and tandem repeats of the cAMP response element (CRE). The HEK293T cell was co-infected with both GLP-1R encoding and CRE Reporter lentivirus. The GLP-1R CRE Reporter cell line was created through sorting by FACS of GFP+ cells responsive to stimulation of exendin-4.

Construction of the GLP-1R Tango Reporter Cell Line: The human GLP-1 receptor was cloned into Tango-pcDNA-Bait vector as fusion to transcription factor GAL4-VP16 at its C terminus. The specific cleavage sequence TEV was interposed between the GLP-1R and the transcription factor. This Bait vector was transfected into U2OS cells containing the β-lactamase reporter gene that is responsive to the transcription factor and TEV protease tagged β-arrestin 2 prey vector and a stable cell line was selected under Geneticin pressure. The stable cells were stimulated with exendin-4 for 18h and loaded with LiveBLAzer-FRET B/G Substrate. The most responsive cells that had the highest blue-to-green fluorescence ratio were sorted using a MoFlo Astrios fluorescence activated cell sorter (Beckman Coulter's).

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, databases, GenBank sequences, patents, and patent applications cited in this specification are herein incorporated by reference as if each was specifically and individually indicated to be incorporated by reference.

What is claimed is:

1. An isolated or recombinant polypeptide comprising a first randomized peptide that is fused at its C-terminus to a second peptide capable of binding to the extracellular domain of glucagon-like peptide 1 receptor (GLP-1R), wherein the randomized peptide comprises ELVDNAV (SEQ ID NO:8), or a conservatively modified variant thereof, and wherein the second peptide comprises SEQ ID NO: 17, except for conservative substitution at one or more residues.

2. The polypeptide of claim 1, comprising or consisting of SEQ ID NO: 36.

3. The polypeptide of claim 1, further comprising an Fc-domain fused at its N-terminus or C-terminus.

4. The polypeptide of claim 3, comprising an Fc-domain that is fused at the C-terminus of SEQ ID NO:36.

5. The polypeptide of claim 3, further comprising a signal peptide at the N-terminus.

6. The polypeptide of claim 3, comprising SEQ ID NO: 45.

* * * * *

SEQUENCE LISTING

```
<160> NUMBER OF SEQ ID NOS: 45

<210> SEQ ID NO 1
<211> LENGTH: 7
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(7)
<223> OTHER INFORMATION: X is any amino acid residue

<400> SEQUENCE: 1

Xaa Xaa Xaa Xaa Xaa Xaa Xaa
1               5

<210> SEQ ID NO 2
<211> LENGTH: 9
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (2)..(6)
<223> OTHER INFORMATION: X is any amino acid residue
<220> FEATURE:
<221> NAME/KEY: MISC_FEATURE
<222> LOCATION: (8)..(9)
<223> OTHER INFORMATION: X is any amino acid residue

<400> SEQUENCE: 2

Cys Xaa Xaa Xaa Xaa Xaa Cys Xaa Xaa
1               5

<210> SEQ ID NO 3
<211> LENGTH: 9
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (2)..(5)
<223> OTHER INFORMATION: X is any amino acid residue
<220> FEATURE:
<221> NAME/KEY: MISC_FEATURE
<222> LOCATION: (7)..(9)
<223> OTHER INFORMATION: X is any amino acid residue

<400> SEQUENCE: 3
```

```
Cys Xaa Xaa Xaa Xaa Cys Xaa Xaa Xaa
1               5
```

<210> SEQ ID NO 4
<211> LENGTH: 10
<212> TYPE: PRT
<213> ORGANISM: Artificial sequence
<220> FEATURE:
<223> OTHER INFORMATION: Synthetic sequence

<400> SEQUENCE: 4

```
Ala Cys Cys Ile Asp Ser Val Cys Val Ile
1               5                   10
```

<210> SEQ ID NO 5
<211> LENGTH: 7
<212> TYPE: PRT
<213> ORGANISM: Artificial seuqence
<220> FEATURE:
<223> OTHER INFORMATION: Synthetic sequence

<400> SEQUENCE: 5

```
Val Cys Pro Asp Cys Gln Val
1               5
```

<210> SEQ ID NO 6
<211> LENGTH: 10
<212> TYPE: PRT
<213> ORGANISM: Artificial sequence
<220> FEATURE:
<223> OTHER INFORMATION: Synthetic sequence

<400> SEQUENCE: 6

```
Ala Cys Ser Tyr Met Ile Asp Cys Val Leu
1               5                   10
```

<210> SEQ ID NO 7
<211> LENGTH: 10
<212> TYPE: PRT
<213> ORGANISM: Artificial sequence
<220> FEATURE:
<223> OTHER INFORMATION: Synthetic sequence

<400> SEQUENCE: 7

```
Ala Cys Tyr Val Lys Phe Pro Cys Asp Ile
1               5                   10
```

<210> SEQ ID NO 8
<211> LENGTH: 7
<212> TYPE: PRT
<213> ORGANISM: Artificial sequence
<220> FEATURE:
<223> OTHER INFORMATION: Synthetic sequence

<400> SEQUENCE: 8

```
Glu Leu Val Asp Asn Ala Val
1               5
```

<210> SEQ ID NO 9
<211> LENGTH: 10
<212> TYPE: PRT
<213> ORGANISM: Artificial sequence
<220> FEATURE:
<223> OTHER INFORMATION: Synthetic sequence

<400> SEQUENCE: 9

```
Ala Cys Ala Leu Glu Val Asp Cys Ala Ile
1               5                   10

<210> SEQ ID NO 10
<211> LENGTH: 10
<212> TYPE: PRT
<213> ORGANISM: Artificial sequence
<220> FEATURE:
<223> OTHER INFORMATION: Synthetic sequence

<400> SEQUENCE: 10

Ala Cys Ser His Ser Gly Phe Cys Val Leu
1               5                   10

<210> SEQ ID NO 11
<211> LENGTH: 10
<212> TYPE: PRT
<213> ORGANISM: Artificial sequence
<220> FEATURE:
<223> OTHER INFORMATION: Synthetic sequence

<400> SEQUENCE: 11

Ala Cys His Asp Arg Val Asp Cys Leu Val
1               5                   10

<210> SEQ ID NO 12
<211> LENGTH: 10
<212> TYPE: PRT
<213> ORGANISM: Artificial sequence
<220> FEATURE:
<223> OTHER INFORMATION: Synthetic sequence

<400> SEQUENCE: 12

Ala Cys Ser Cys Tyr Gly Tyr Cys Ala Thr
1               5                   10

<210> SEQ ID NO 13
<211> LENGTH: 10
<212> TYPE: PRT
<213> ORGANISM: ARTIFICIAL SEQUENCE
<220> FEATURE:
<223> OTHER INFORMATION: Synthetic sequence

<400> SEQUENCE: 13

Ala Cys Gly Trp Cys Gly Glu Cys Thr Val
1               5                   10

<210> SEQ ID NO 14
<211> LENGTH: 7
<212> TYPE: PRT
<213> ORGANISM: Artificial sequence
<220> FEATURE:
<223> OTHER INFORMATION: Synthetic sequence

<400> SEQUENCE: 14

Val Met Ile Asp Gln Arg Leu
1               5

<210> SEQ ID NO 15
<211> LENGTH: 10
<212> TYPE: PRT
<213> ORGANISM: Artificial sequence
<220> FEATURE:
<223> OTHER INFORMATION: Synthetic sequence

<400> SEQUENCE: 15

Ala Cys Arg Val Asp Gln Arg Cys Phe Trp
```

```
1               5                   10
```

<210> SEQ ID NO 16
<211> LENGTH: 10
<212> TYPE: PRT
<213> ORGANISM: Artificial sequence
<220> FEATURE:
<223> OTHER INFORMATION: Synthetic sequence

<400> SEQUENCE: 16

```
Ala Cys Cys Val Cys Phe Thr Cys Val Phe
1               5                   10
```

<210> SEQ ID NO 17
<211> LENGTH: 31
<212> TYPE: PRT
<213> ORGANISM: Homo sapiens

<400> SEQUENCE: 17

```
Asp Leu Ser Lys Gln Met Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30
```

<210> SEQ ID NO 18
<211> LENGTH: 22
<212> TYPE: PRT
<213> ORGANISM: Homo sapiens

<400> SEQUENCE: 18

```
Asp Val Ser Ser Tyr Leu Glu Gly Gln Ala Ala Lys Glu Phe Ile Ala
1               5                   10                  15

Trp Leu Val Lys Gly Arg
            20
```

<210> SEQ ID NO 19

<400> SEQUENCE: 19

000

<210> SEQ ID NO 20

<400> SEQUENCE: 20

000

<210> SEQ ID NO 21
<211> LENGTH: 33
<212> TYPE: PRT
<213> ORGANISM: Homo sapiens

<400> SEQUENCE: 21

```
Gly Gly Asp Leu Ser Lys Gln Met Glu Glu Ala Val Arg Leu Phe
1               5                   10                  15

Ile Glu Trp Leu Lys Asn Gly Gly Pro Ser Ser Gly Ala Pro Pro Pro
            20                  25                  30

Ser
```

<210> SEQ ID NO 22
<211> LENGTH: 9
<212> TYPE: PRT
<213> ORGANISM: Artificial sequence
<220> FEATURE:

<223> OTHER INFORMATION: Synthetic sequence

<400> SEQUENCE: 22

Cys Cys Ile Asp Ser Val Cys Val Ile
1               5

<210> SEQ ID NO 23
<211> LENGTH: 9
<212> TYPE: PRT
<213> ORGANISM: Artificial sequence
<220> FEATURE:
<223> OTHER INFORMATION: Synthetic sequence

<400> SEQUENCE: 23

Cys Ser Tyr Met Ile Asp Cys Val Leu
1               5

<210> SEQ ID NO 24
<211> LENGTH: 9
<212> TYPE: PRT
<213> ORGANISM: Artificial sequence
<220> FEATURE:
<223> OTHER INFORMATION: Synthetic sequence

<400> SEQUENCE: 24

Cys Tyr Val Lys Phe Pro Cys Asp Ile
1               5

<210> SEQ ID NO 25
<211> LENGTH: 9
<212> TYPE: PRT
<213> ORGANISM: Artificial sequence
<220> FEATURE:
<223> OTHER INFORMATION: Synthetic sequence

<400> SEQUENCE: 25

Cys Ala Leu Glu Val Asp Cys Ala Ile
1               5

<210> SEQ ID NO 26
<211> LENGTH: 9
<212> TYPE: PRT
<213> ORGANISM: Artificial sequence
<220> FEATURE:
<223> OTHER INFORMATION: Synthetic sequence

<400> SEQUENCE: 26

Cys Ser His Ser Gly Phe Cys Val Leu
1               5

<210> SEQ ID NO 27
<211> LENGTH: 9
<212> TYPE: PRT
<213> ORGANISM: Artificial sequence
<220> FEATURE:
<223> OTHER INFORMATION: Synthetic sequence

<400> SEQUENCE: 27

Cys His Asp Arg Val Asp Cys Leu Val
1               5

<210> SEQ ID NO 28
<211> LENGTH: 9
<212> TYPE: PRT
<213> ORGANISM: Artificial sequence
<220> FEATURE:
<223> OTHER INFORMATION: Synthetic sequence

```
<400> SEQUENCE: 28

Cys Ser Cys Tyr Gly Tyr Cys Ala Thr
 1               5

<210> SEQ ID NO 29
<211> LENGTH: 9
<212> TYPE: PRT
<213> ORGANISM: Artificial sequence
<220> FEATURE:
<223> OTHER INFORMATION: Synthetic sequence

<400> SEQUENCE: 29

Cys Gly Trp Cys Gly Glu Cys Thr Val
 1               5

<210> SEQ ID NO 30
<211> LENGTH: 9
<212> TYPE: PRT
<213> ORGANISM: Artificial sequence
<220> FEATURE:
<223> OTHER INFORMATION: Synthetic sequence

<400> SEQUENCE: 30

Cys Arg Val Asp Gln Arg Cys Phe Trp
 1               5

<210> SEQ ID NO 31
<211> LENGTH: 9
<212> TYPE: PRT
<213> ORGANISM: Artificial sequence
<220> FEATURE:
<223> OTHER INFORMATION: Synthetic sequence

<400> SEQUENCE: 31

Cys Cys Val Cys Phe Thr Cys Val Phe
 1               5

<210> SEQ ID NO 32
<211> LENGTH: 40
<212> TYPE: PRT
<213> ORGANISM: Artificial sequence
<220> FEATURE:
<223> OTHER INFORMATION: Synthetic sequence

<400> SEQUENCE: 32

Val Cys Pro Asp Cys Gln Val Gly Gly Asp Leu Ser Lys Gln Met Glu
 1               5                  10                  15

Glu Glu Ala Val Arg Leu Phe Ile Glu Trp Leu Lys Asn Gly Gly Pro
                20                  25                  30

Ser Ser Gly Ala Pro Pro Pro Ser
            35                  40

<210> SEQ ID NO 33
<211> LENGTH: 32
<212> TYPE: PRT
<213> ORGANISM: Artificial sequence
<220> FEATURE:
<223> OTHER INFORMATION: Synthetic sequence

<400> SEQUENCE: 33

Val Cys Pro Asp Cys Gln Val Gly Gly Asp Val Ser Ser Tyr Leu Glu
 1               5                  10                  15

Gly Gln Ala Ala Lys Glu Phe Ile Ala Trp Leu Val Lys Gly Arg Gly
                20                  25                  30
```

<210> SEQ ID NO 34
<211> LENGTH: 43
<212> TYPE: PRT
<213> ORGANISM: Artificial sequence
<220> FEATURE:
<223> OTHER INFORMATION: Synthetic sequence

<400> SEQUENCE: 34

Ala Cys Cys Ile Asp Ser Val Cys Val Ile Gly Gly Asp Leu Ser Lys
1               5                   10                  15

Gln Met Glu Glu Glu Ala Val Arg Leu Phe Ile Glu Trp Leu Lys Asn
            20                  25                  30

Gly Gly Pro Ser Ser Gly Ala Pro Pro Pro Ser
        35                  40

<210> SEQ ID NO 35
<211> LENGTH: 43
<212> TYPE: PRT
<213> ORGANISM: Artificial sequence
<220> FEATURE:
<223> OTHER INFORMATION: Synthetic sequence

<400> SEQUENCE: 35

Ala Cys Ser Tyr Met Ile Asp Cys Val Leu Gly Gly Asp Leu Ser Lys
1               5                   10                  15

Gln Met Glu Glu Glu Ala Val Arg Leu Phe Ile Glu Trp Leu Lys Asn
            20                  25                  30

Gly Gly Pro Ser Ser Gly Ala Pro Pro Pro Ser
        35                  40

<210> SEQ ID NO 36
<211> LENGTH: 40
<212> TYPE: PRT
<213> ORGANISM: Artificial sequence
<220> FEATURE:
<223> OTHER INFORMATION: Synthetic sequence

<400> SEQUENCE: 36

Glu Leu Val Asp Asn Ala Val Gly Gly Asp Leu Ser Lys Gln Met Glu
1               5                   10                  15

Glu Glu Ala Val Arg Leu Phe Ile Glu Trp Leu Lys Asn Gly Gly Pro
            20                  25                  30

Ser Ser Gly Ala Pro Pro Pro Ser
        35                  40

<210> SEQ ID NO 37
<211> LENGTH: 43
<212> TYPE: PRT
<213> ORGANISM: Artificial sequence
<220> FEATURE:
<223> OTHER INFORMATION: Synthetic sequence

<400> SEQUENCE: 37

Ala Cys Gly Trp Cys Gly Glu Cys Thr Val Gly Gly Asp Leu Ser Lys
1               5                   10                  15

Gln Met Glu Glu Glu Ala Val Arg Leu Phe Ile Glu Trp Leu Lys Asn
            20                  25                  30

Gly Gly Pro Ser Ser Gly Ala Pro Pro Pro Ser
        35                  40

<210> SEQ ID NO 38

<211> LENGTH: 22
<212> TYPE: PRT
<213> ORGANISM: Homo sapiens

<400> SEQUENCE: 38

Asp Leu Ser Lys Gln Met Glu Glu Ala Val Arg Leu Phe Ile Glu
1               5                   10                  15

Trp Leu Lys Asn Gly Gly
            20

<210> SEQ ID NO 39
<211> LENGTH: 23
<212> TYPE: PRT
<213> ORGANISM: Homo sapiens

<400> SEQUENCE: 39

Asp Val Ser Ser Tyr Leu Glu Gly Gln Ala Ala Lys Glu Phe Ile Ala
1               5                   10                  15

Trp Leu Val Lys Gly Arg Gly
            20

<210> SEQ ID NO 40
<211> LENGTH: 39
<212> TYPE: PRT
<213> ORGANISM: Homo sapiens

<400> SEQUENCE: 40

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 41
<211> LENGTH: 10
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (3)..(7)
<223> OTHER INFORMATION: X is any amino acid residue
<220> FEATURE:
<221> NAME/KEY: MISC_FEATURE
<222> LOCATION: (9)..(10)
<223> OTHER INFORMATION: X is any amino acid residue

<400> SEQUENCE: 41

Ala Cys Xaa Xaa Xaa Xaa Xaa Cys Xaa Xaa
1               5                   10

<210> SEQ ID NO 42
<211> LENGTH: 10
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (3)..(6)
<223> OTHER INFORMATION: X is any amino acid residue.
<220> FEATURE:
<221> NAME/KEY: MISC_FEATURE
<222> LOCATION: (8)..(10)
<223> OTHER INFORMATION: X is any amino acid residue.

```
<400> SEQUENCE: 42

Ala Cys Xaa Xaa Xaa Cys Xaa Xaa Xaa
1               5                   10

<210> SEQ ID NO 43
<211> LENGTH: 5
<212> TYPE: PRT
<213> ORGANISM: Artificial sequence
<220> FEATURE:
<223> OTHER INFORMATION: Synthetic sequence

<400> SEQUENCE: 43

Gly Gly Gly Gly Ser
1               5

<210> SEQ ID NO 44
<211> LENGTH: 20
<212> TYPE: PRT
<213> ORGANISM: Homo sapiens

<400> SEQUENCE: 44

Met Tyr Arg Met Gln Leu Leu Ser Cys Ile Ala Leu Ser Leu Ala Leu
1               5                   10                  15

Val Thr Asn Ser
            20

<210> SEQ ID NO 45
<211> LENGTH: 274
<212> TYPE: PRT
<213> ORGANISM: Artificial sequence
<220> FEATURE:
<223> OTHER INFORMATION: Synthetic sequence

<400> SEQUENCE: 45

Glu Leu Val Asp Asn Ala Val Gly Gly Asp Leu Ser Lys Gln Met Glu
1               5                   10                  15

Glu Glu Ala Val Arg Leu Phe Ile Glu Trp Leu Lys Asn Gly Gly Pro
                20                  25                  30

Ser Ser Gly Ala Pro Pro Ser Ala Ser Glu Pro Lys Ser Cys Asp
            35                  40                  45

Lys Thr His Thr Cys Pro Pro Cys Pro Ala Pro Glu Leu Leu Gly Gly
        50                  55                  60

Pro Ser Val Phe Leu Phe Pro Pro Lys Pro Lys Asp Thr Leu Met Ile
65                  70                  75                  80

Ser Arg Thr Pro Glu Val Thr Cys Val Val Val Asp Val Ser His Glu
                85                  90                  95

Asp Pro Glu Val Lys Phe Asn Trp Tyr Val Asp Gly Val Glu Val His
                100                 105                 110

Asn Ala Lys Thr Lys Pro Arg Glu Glu Gln Tyr Asn Ser Thr Tyr Arg
            115                 120                 125

Val Val Ser Val Leu Thr Val Leu His Gln Asp Trp Leu Asn Gly Lys
        130                 135                 140

Glu Tyr Lys Cys Lys Val Ser Asn Lys Ala Leu Pro Ala Pro Ile Glu
145                 150                 155                 160

Lys Thr Ile Ser Lys Ala Lys Gly Gln Pro Arg Glu Pro Gln Val Tyr
                165                 170                 175

Thr Leu Pro Pro Ser Arg Asp Glu Leu Thr Lys Asn Gln Val Ser Leu
                180                 185                 190
```

```
Thr Cys Leu Val Lys Gly Phe Tyr Pro Ser Asp Ile Ala Val Glu Trp
        195                 200                 205

Glu Ser Asn Gly Gln Pro Glu Asn Asn Tyr Lys Thr Thr Pro Pro Val
    210                 215                 220

Leu Asp Ser Asp Gly Ser Phe Phe Leu Tyr Ser Lys Leu Thr Val Asp
225                 230                 235                 240

Lys Ser Arg Trp Gln Gln Gly Asn Val Phe Ser Cys Ser Val Met His
                245                 250                 255

Glu Ala Leu His Asn His Tyr Thr Gln Lys Ser Leu Ser Leu Ser Pro
            260                 265                 270

Gly Lys
```